(12) United States Patent
Maginot

(10) Patent No.: US 7,008,412 B2
(45) Date of Patent: Mar. 7, 2006

(54) SUBCUTANEOUS PORT CATHETER SYSTEM AND ASSOCIATED METHOD

(75) Inventor: Thomas J. Maginot, Crown Point, IN (US)

(73) Assignee: CathLogic, Inc., Crown Point, IN (US)

( * ) Notice: Subject to any disclaimer, the term of this patent is extended or adjusted under 35 U.S.C. 154(b) by 136 days.

(21) Appl. No.: 10/007,679

(22) Filed: Dec. 4, 2001

(65) Prior Publication Data

US 2002/0107475 A1 Aug. 8, 2002

Related U.S. Application Data

(63) Continuation-in-part of application No. 09/716,814, filed on Nov. 20, 2000, which is a continuation-in-part of application No. 09/443,877, filed on Nov. 19, 1999, now Pat. No. 6,156,016, which is a continuation-in-part of application No. 09/078,834, filed on May 14, 1998, now Pat. No. 5,989,213.

(60) Provisional application No. 60/070,583, filed on Jan. 6, 1998.

(51) Int. Cl.
*A61M 25/00* (2006.01)

(52) U.S. Cl. .................. 604/523; 604/264; 604/533

(58) Field of Classification Search .............. 604/6–16, 604/28, 29, 43, 891.1, 93.01, 94.01, 500, 604/506, 508, 510, 158, 523, 164.01–164.02, 604/164.08, 164.09, 165.01–165.02, 167.01–167.06, 604/171, 174, 175, 198, 264, 265, 266, 269, 604/890.1, 533–535

See application file for complete search history.

(56) References Cited

U.S. PATENT DOCUMENTS

| | | | |
|---|---|---|---|
| 2,448,232 A | 8/1948 | Muse | |
| 3,894,540 A | 7/1975 | Bonner, Jr. | |
| 4,014,333 A | 3/1977 | McIntyre | |
| 4,023,559 A | 5/1977 | Gaskell | |

(Continued)

FOREIGN PATENT DOCUMENTS

FR 2612784 A1 * 9/1988

OTHER PUBLICATIONS

Pages 366–367 of *Interventional Radiology*, vol. one, Second Edition.

Marketing brochure from Cook Critical Care, A division of Cook, Incorporated.

Marketing brochure from Micro Therapeutics, Inc.

Marketing brochure entitled "Bard Access Systems Hickman: ® Hemodialysis/Plasmapheresis Catheter", Bard Access Systems, Hickman, Groshong, Designs for Life™, 5425 West Amelia Earhart Drive, Salt Lake City, Utah 84116. Published at least as early as May 13, 1998.

(Continued)

*Primary Examiner*—Nicholas D. Lucchesi
*Assistant Examiner*—Michael M. Thompson
(74) *Attorney, Agent, or Firm*—Paul J. Maginot

(57) ABSTRACT

A subcutaneous port catheter system includes a reservoir defining a chamber therein. The catheter system also includes a guide catheter attached to the reservoir. The guide catheter has a guide lumen and a distal guide orifice. The catheter system further includes an inner catheter attached to the reservoir. The inner catheter is positioned within the guide lumen and extends through the distal guide orifice. A method of advancing fluid into a blood vessel of a body of a patient is also disclosed.

22 Claims, 46 Drawing Sheets

U.S. PATENT DOCUMENTS

| | | | |
|---|---|---|---|
| 4,157,709 A | 6/1979 | Schuster et al. | |
| 4,266,999 A | 5/1981 | Baier | |
| 4,324,262 A | 4/1982 | Hall | |
| 4,392,855 A | 7/1983 | Oreopoulos et al. | |
| 4,406,656 A | 9/1983 | Hattler et al. | |
| 4,431,426 A | 2/1984 | Groshong et al. | |
| 4,437,857 A | 3/1984 | Goldstein et al. | |
| 4,457,313 A | 7/1984 | Alter | |
| 4,468,216 A | 8/1984 | Muto | |
| 4,493,696 A | 1/1985 | Uldall | |
| 4,583,968 A | 4/1986 | Mahurkar | |
| 4,626,240 A | 12/1986 | Edelman et al. | |
| 4,665,925 A | 5/1987 | Millar | |
| 4,738,667 A | 4/1988 | Galloway | |
| 4,900,202 A | 2/1990 | Weinhold | |
| 4,936,826 A | 6/1990 | Amarasinghe | |
| 5,013,194 A | 5/1991 | Weinhold | |
| 5,053,023 A | 10/1991 | Martin | |
| 5,156,592 A | 10/1992 | Martin et al. | |
| 5,190,529 A | 3/1993 | McCrory et al. | |
| 5,213,567 A | 5/1993 | Masaki | |
| 5,215,530 A | 6/1993 | Hogan | |
| 5,236,424 A | 8/1993 | Imran | |
| 5,250,034 A | 10/1993 | Appling et al. | |
| 5,261,416 A | 11/1993 | Taussig | |
| 5,273,527 A | 12/1993 | Schatz et al. | |
| 5,279,590 A | 1/1994 | Sinko et al. | |
| 5,370,613 A | 12/1994 | Helmy | |
| 5,405,320 A | 4/1995 | Twardowski et al. | |
| 5,405,323 A | 4/1995 | Rogers et al. | |
| 5,417,669 A | 5/1995 | Castaneda et al. | |
| 5,470,180 A | 11/1995 | Jore | |
| 5,498,240 A | 3/1996 | Bagaoisan et al. | |
| 5,514,112 A | 5/1996 | Chu et al. | |
| 5,531,684 A * | 7/1996 | Ensminger et al. | 604/288.03 |
| 5,569,182 A | 10/1996 | Twardowski et al. | |
| 5,569,204 A | 10/1996 | Cramer | |
| 5,591,138 A | 1/1997 | Vaillancourt | |
| 5,599,317 A | 2/1997 | Hauser | |
| 5,616,131 A | 4/1997 | Sauer et al. | |
| 5,624,396 A | 4/1997 | McNamara et al. | |
| 5,681,336 A | 10/1997 | Clement et al. | |
| 5,779,404 A | 7/1998 | Jore | |
| 5,971,958 A | 10/1999 | Zhang | |
| 6,007,522 A | 12/1999 | Agro et al. | |
| 6,080,170 A | 6/2000 | Nash et al. | |
| 6,099,508 A | 8/2000 | Bousquet | |
| 6,156,016 A | 12/2000 | Maginot | |
| 6,190,353 B1 | 2/2001 | Makower et al. | |
| 6,190,371 B1 | 2/2001 | Maginot et al. | |
| 6,241,744 B1 | 6/2001 | Imran et al. | |
| 6,261,257 B1 | 7/2001 | Uflacker et al. | |
| 6,283,951 B1 | 9/2001 | Flaherty et al. | |

OTHER PUBLICATIONS

Crain M: Management of fibrin sheaths I: Percutaneous fibrin sheath stripping. Seminars in Dialysis 1998;11(6):336–341.

Lund GB: Management of fibrin sheaths II: Thrombolytic therapy. Seminars in Dialysis 1998;11(6):342–346.

Xiang DZ, Verbeken EK, Van Lommel ATL, et al: Composition and formation of the sleeve enveloping a central venous catheter. J Vasc Surg 1998;28:260–271.

Merport M. Murphy TP, Egglin TK, et al,: Fibrin sheath stripping versus catheter exchange for the treatment of failed tunneled homodialysis catheters: Randomized clinical trial. JVIR 2000;11:1115–1120.

Savader SJ, Haikal LC, Ehrman KO, et al; Hemodialysis catheter–associated fibrin sheaths: Treatment with a Low-dose rt–PA infusion. JVIR 2000;11:1131–1136.

Gray RJ, Levitin A. Buck D, et al: Percutaneous fibrin sheath stripping versus transcatheter urokinase infusion for malfunctioning well–positioned tunneled central venous dialysis catheters: A prospective randomized trial. JVIR 2000:11:1121–1129.

Marketing brochure for Cook Inc., Bunchman Coaxial Double Lumen Hemodialysis/Hemofiltration Catheter Set, © 1995.

* cited by examiner

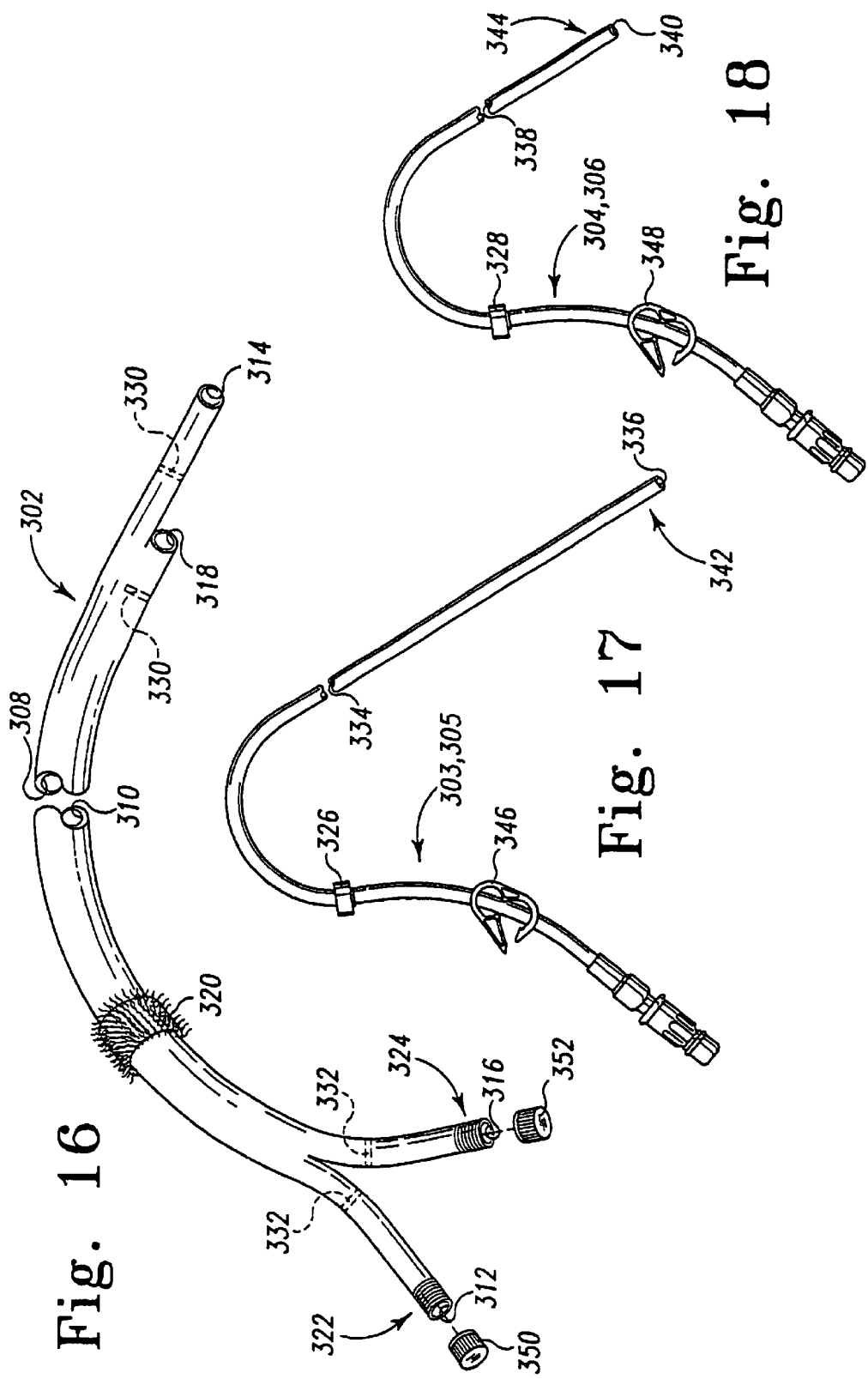

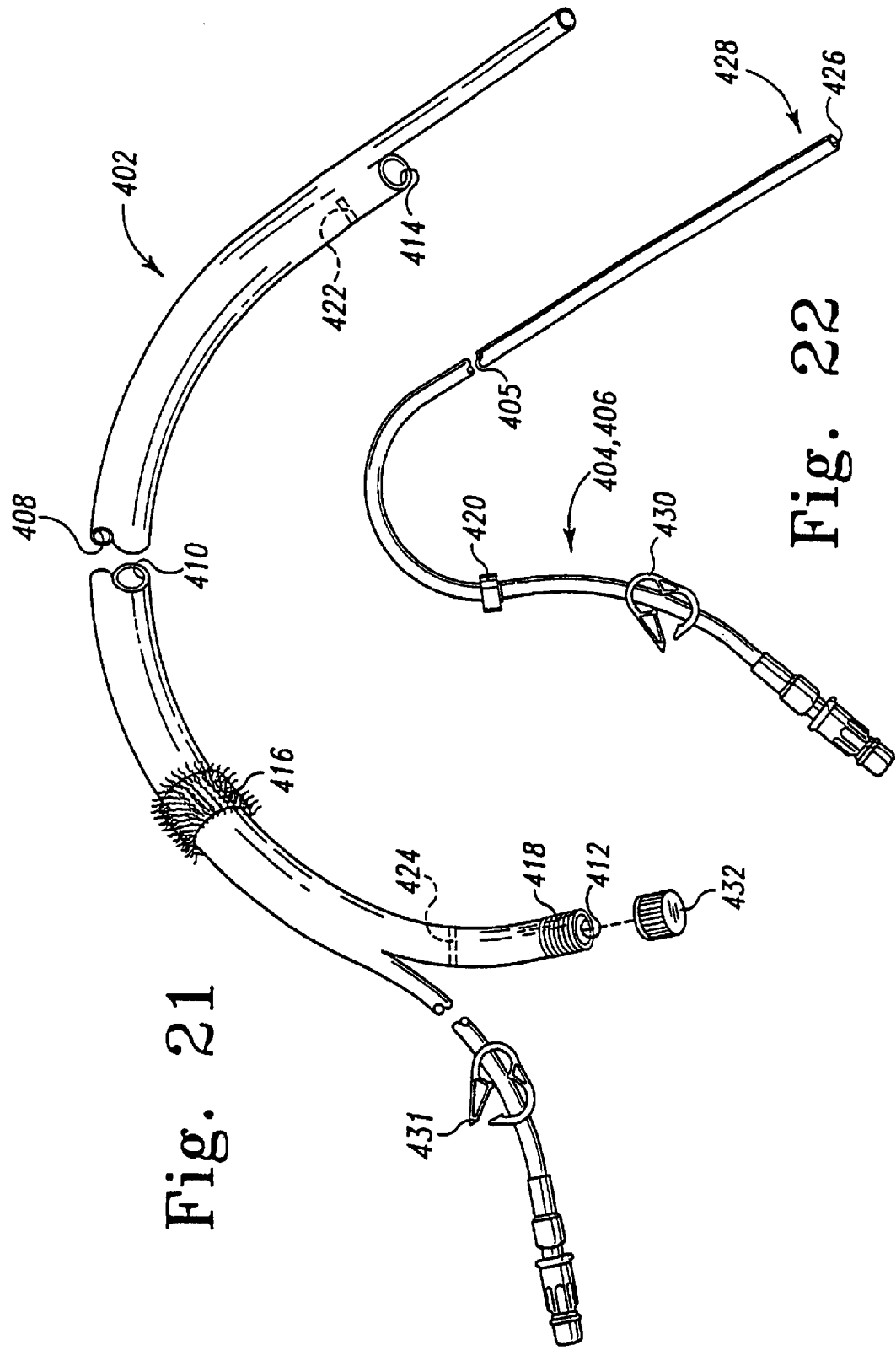

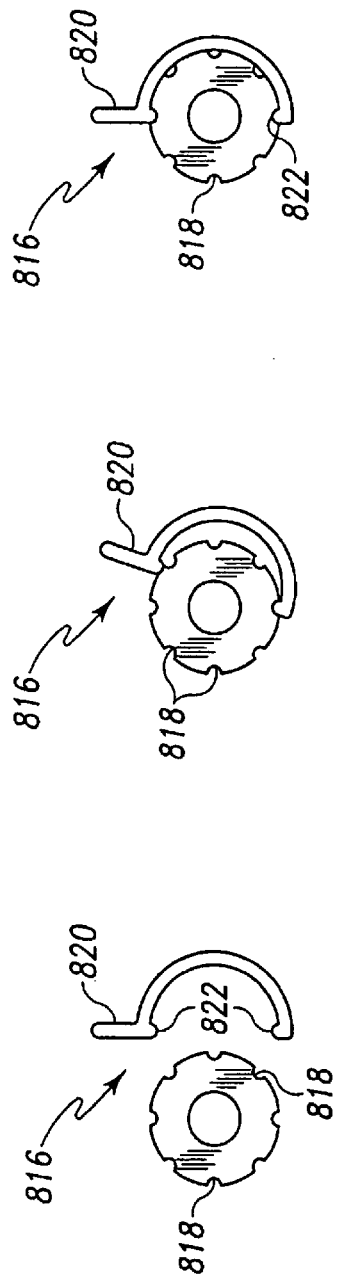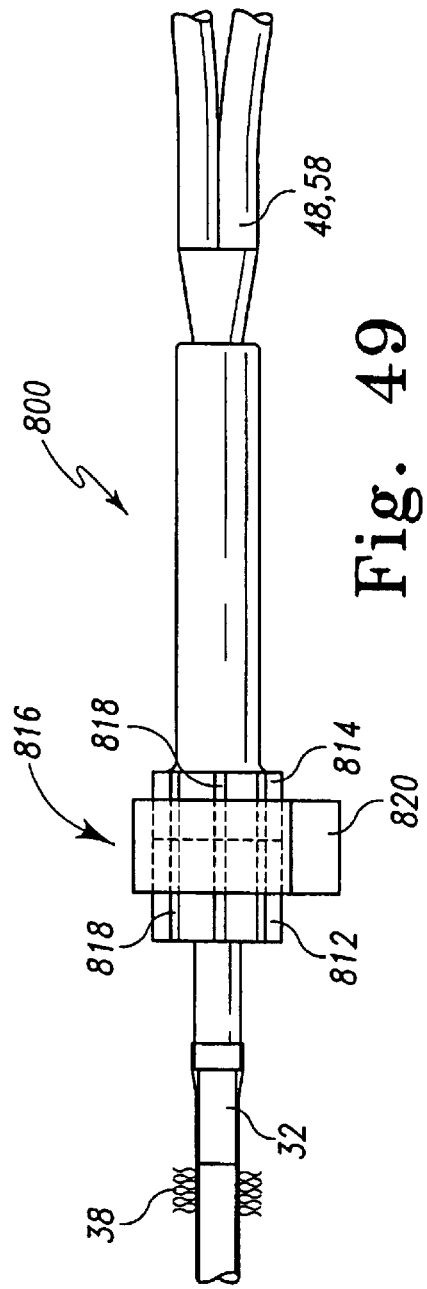
Fig. 49A  Fig. 49B  Fig. 49C
Fig. 49

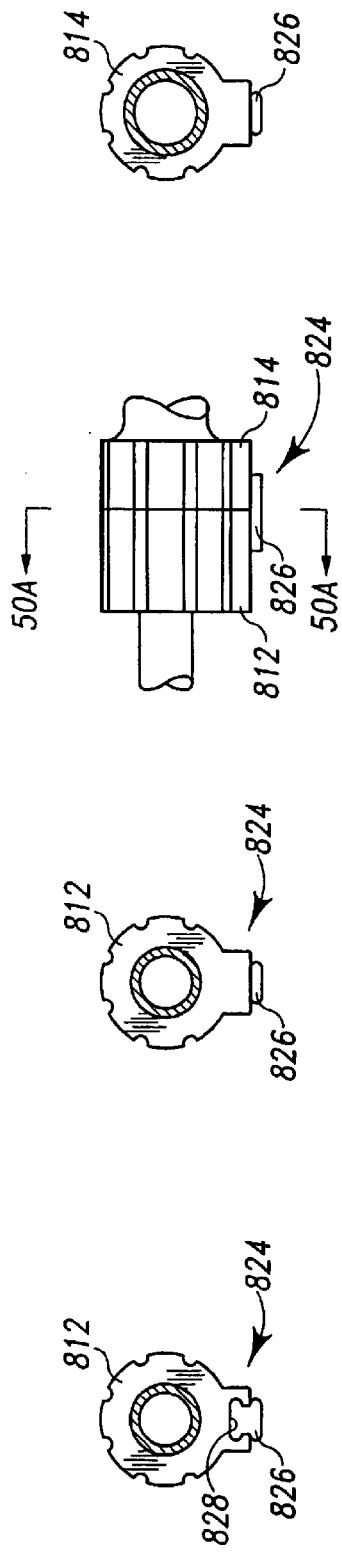
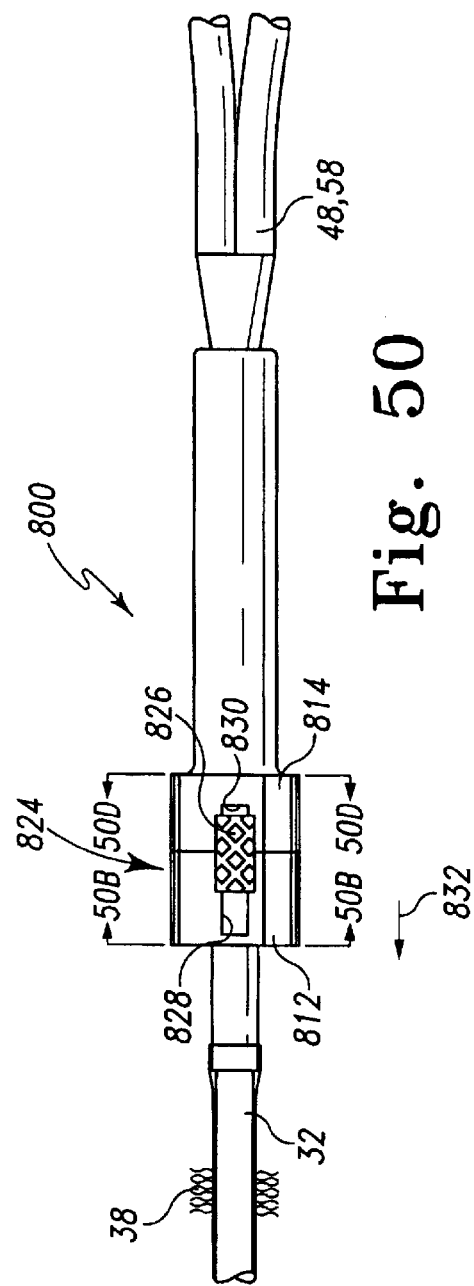

SUBCUTANEOUS PORT CATHETER SYSTEM AND ASSOCIATED METHOD

This application is a continuation-in-part of co-pending application Ser. No. 09/716,814, filed on Nov. 20, 2000, which in turn is a continuation-in-part of co-pending application Ser. No. 09/443,877, filed on Nov. 19, 1999, now U.S. Pat. No. 6,156,016, which in turn is a continuation-in-part of co-pending application Ser. No. 09/078,834, filed on May 14, 1998, now U.S. Pat. No. 5,989,213, which in turn claims the benefit of U.S. Provisional Application Ser. No. 60/070,583, filed on Jan. 6, 1998. The disclosures of each of the above-identified patent applications and patents being hereby totally incorporated by reference in their entirety.

CROSS REFERENCE

Cross reference is made to co-pending U.S. patent application Ser. No. 10/005,277, entitled "Medical Procedure Using Catheter System having Removability Feature" by Thomas J. Maginot and Paul J. Maginot filed on the same date herewith, and co-pending U.S. patent application Ser. No. 10/006,799, entitled "Retractable Catheter Systems and Associated Methods" by Paul J. Maginot and Thomas J. Maginot filed on the same date herewith, and co-pending U.S. patent application Ser. No. 09/716,308, entitled "Retractable Catheter Systems" by Paul J. Maginot and Thomas J. Maginot filed Nov. 20, 2000, and co-pending U.S. patent application Ser. No. 09/716,815, entitled "Method of Performing Medical Procedures Using Retractable Catheter Systems" by Paul J. Maginot and Thomas J. Maginot also filed on Nov. 20, 2000, and co-pending U.S. patent application Ser. No. 09/443,876, entitled "Retractable Catheter Systems and Associated Methods" by Paul J. Maginot and Thomas J. Maginot filed on Nov. 19, 1999, and also U.S. Pat. No. 6,190,371 issued to Maginot et al. on Feb. 20, 2001, the disclosures of each of the above-identified patent applications and patent being hereby totally incorporated by reference in their entirety.

BACKGROUND OF THE INVENTION

The present invention relates generally to catheters, and more particularly to long-term catheter systems, such as long-term dialysis catheter systems and associated methods of maintaining blood flow in catheter systems.

Various medical procedures require that a patient be catheterized. For example, catheterization may be required when a patient undergoes hemodialysis or has a clot aspirated from a blood vessel. Generally, the length of time the patient will be catheterized dictates whether a physician will utilize a "temporary catheterization technique" (i.e. a technique in which the catheter is left in a blood vessel for a relatively short period of time such as a few minutes, hours, days, or weeks) or a "permanent catheterization technique" (i.e. a technique in which the catheter is left in a blood vessel for a relatively long period of time such as several months or indefinitely).

For example, a procedure in which a clot is aspirated from a blood vessel typically includes placing the catheter in the blood vessel for a relatively short period of time such as a few minutes to a few hours and then withdrawing the catheter once the clot has been removed. Therefore, when performing such an aspiration procedure, it is common for a physician to use the temporary catheterization technique to place the catheter in the blood vessel of the patient.

On the other hand, when a procedure is performed to effect hemodialysis, a physician may place a catheter in the blood vessel for a relatively long period of time. In particular, a patient suffering from kidney failure who is involved in a hemodialysis regimen typically requires a dialysis session three days per week for an indefinite period of time whereby extra fluid, chemicals, and wastes are removed from his/her body. A patient who is involved in such a hemodialysis regimen may need a catheter placed in his/her blood vessel for a relatively long period of time in order to provide a ready means for vascular access into his/her bloodstream over such relatively long period of time. This long term placement of the catheter for dialysis purposes may be desirable for a number of reasons.

Firstly, a patient may have experienced progressive loss of other conventional long term vascular access possibilities such as surgically created arteriovenous fistulas. Accordingly, the long term placement of the catheter in the patient's blood vessel may be the best alternative for the patient as he/she proceeds with the hemodialysis regimen.

Additionally, the long term placement of the catheter in the patient's blood vessel may be desirable after initial creation of an arteriovenous fistula in the patient's body. In particular, it is desirable to provide a ready means for vascular access into the patient's bloodstream during a maturation period of the arteriovenous fistula. The maturation period allows the arteriovenous fistula to develop sufficiently so that it will function as a ready means for vascular access into the patient's bloodstream which may be safely punctured multiple times per week for hemodialysis. The length of time of this maturation period is typically on the order of several weeks (e.g. three weeks) to many months (e.g. six months).

Therefore, when performing a hemodialysis procedure, it is common for a physician to use the permanent catheterization technique to place the catheter in the blood vessel of the patient.

These two catheterization techniques are significantly different with respect to their complexity and degree of invasiveness. For example, in the case of the temporary catheterization technique, it is common to insert a temporary catheter into a patient's blood vessel using a "direct puncture technique." This technique entails creating a small incision in a patient's skin with a scalpel directly over the blood vessel to be catheterized. A needle is then advanced through the skin incision and subcutaneous tissue and into the blood vessel. Thereafter, a guidewire is advanced through the needle into the blood vessel and the needle is subsequently removed over the guidewire. Then, one or more tubular vessel dilators are used to widen the opening defined in the skin and subcutaneous tissue, and further to widen the opening defined in the blood vessel wall to a caliber similar to that of the temporary catheter. The temporary catheter is then advanced over the guidewire and into the blood vessel. Thereafter, the guidewire is removed.

When the temporary catheterization technique is used during a clot aspiration procedure, two catheters are usually placed in the blood vessel of a patient. In particular, an outer catheter is usually placed within the blood vessel using the above described direct puncture technique so that its distal opening is located near the clot. Thereafter, an inner catheter having a smaller caliber relative to the outer catheter is advanced through a lumen of the outer catheter. While the inner catheter is positioned within the outer catheter, an aspiration vacuum is applied to the inner catheter with a syringe. If the size of the clot (or fragments thereof) are smaller than the inner diameter of the inner catheter, then the clot or clot fragments are drawn into and through the inner catheter thereby removing the clot from the blood vessel. If the size of the clot or clot fragments are larger than the inner diameter of the inner catheter, then the clot or clot fragments are drawn to a location adjacent to the distal orifice of the inner catheter. Subsequently, while the aspiration vacuum is still being applied, the inner catheter is withdrawn from the outer catheter thereby additionally withdrawing the clot or clot fragments from the outer catheter and the patient's blood vessel. Thereafter, the outer catheter remains temporarily in place within the blood vessel of the patient for subsequent injections of radiographic contrast for imaging purposes to determine the extent of clot remaining in the blood vessel as well as to determine if clot has migrated to another location within the blood vessel. The outer catheter, which remains temporarily in place in the blood vessel, provides a conduit for the inner catheter to be advanced back into the patient's blood vessel for additional aspiration attempts which are usually required for complete removal of the clot from the blood vessel.

If an outer catheter needs to be replaced during a clot aspiration procedure because of catheter malfunction, such replacement can be accomplished by advancing a guidewire through the lumen of the outer catheter and into the blood vessel. The existing outer catheter can then be removed over the guidewire to a location outside of the patient's body. Thereafter, a new outer catheter is placed in the patient's blood vessel by advancing the new outer catheter over the guidewire as discussed above.

In contrast to the temporary catheterization technique, the permanent catheterization technique typically entails inserting a permanent catheter into a patient's blood vessel using a "tunneled catheter technique." The tunneled catheter technique includes (i) creating a first opening by making a small incision in a patient's skin with a scalpel directly over the blood vessel to be catheterized, (ii) puncturing the blood vessel at a location directly below the first opening by advancing a needle through the skin incision and subcutaneous tissue and into the blood vessel, (iii) advancing a guidewire through the needle into the blood vessel, (iv) removing the needle over the guidewire, (v) passing one or more tubular vessel dilators over the guidewire to widen the opening defined in the skin and subcutaneous tissue, and further to widen the opening defined in the blood vessel wall to a caliber similar to that of the tubular guide, (vi) advancing the tubular guide over the guidewire and into the blood vessel, (vii) thereafter, creating a second opening in the patient's skin spaced apart at least several centimeters from the first opening, (viii) advancing a tunneling instrument from the second opening to the first opening so as to create a passageway within the subcutaneous tissue under the skin between the first opening and the second opening, (ix) advancing a permanent catheter having a tissue ingrowth member attached to an outer surface thereof into the second opening and through the passageway such that a distal end of the permanent catheter is located adjacent the first opening, (x) inserting the distal end of the permanent catheter through the tubular guide member and into the blood vessel to be catheterized whereby the tissue ingrowth member is positioned in the subcutaneous tissue, (xi) removing the tubular guide member, and (xii) closing the first opening with suture whereby the permanent catheter (a) is no longer exposed through the first opening, (b) extends for at least several centimeters under the patient's skin between second opening and the location where the permanent catheter enters the blood vessel, and (c) extends out of the second opening so that a proximal end of the permanent catheter is located outside of the patient's body.

In contrast to the direct puncture catheter technique, the tunneled catheter technique results in the placement of a catheter in a patient's body in a manner which allows the catheter to remain safely in the patient's body for a relatively long period of time. For example, a degree of safety is achieved by separating the following two openings by at least several centimeters: (i) the skin opening through which the catheter enters the patient's body, and (ii) the blood vessel opening through which the catheter enters the patient's vascular system. This safety feature decreases the likelihood that bacteria will migrate up the length of the catheter from the skin opening and cause an infection at the blood vessel opening.

In addition, another degree of safety is achieved by providing a tissue ingrowth member which is attached to and extends around an outer surface of the catheter. As the catheter is left in the patient's body over a period of time, the tissue ingrowth member becomes affixed to the subcutaneous tissue of the patient's body thereby providing a secure attachment of the catheter to the patient's body. Providing a secure attachment between the catheter and the patient's body reduces the likelihood that the catheter will be inadvertently removed or withdrawn from the patient's body. Moreover, since the subcutaneous tissue becomes attached to the tissue ingrowth member, a physical barrier is created between the following two openings: (i) the skin opening through which the catheter enters the patient's body, and (ii) the blood vessel opening through which the catheter enters the patient's vascular system. This physical barrier further decreases the likelihood that bacteria will migrate up the length of the catheter from the skin opening and cause an infection at the blood vessel opening.

While the tunneled catheter technique provides the significant advantage of allowing the catheter to remain safely in the patient's body for a relatively long period of time, significant disadvantages of the tunneled catheter technique exists. For example, when a catheter remains in a blood vessel for a long period of time, there is a tendency for blood clots including fibrin (e.g. in the form of a fibrin sheath) to attach to and build-up on the outer and inner surfaces of the portion of the catheter which is located within the blood vessel. The above described attachment and build-up tends to occlude the various distal openings defined in the catheter which enable fluid movement into and out of the catheter. For instance, attempts at withdrawing blood through the catheter may be unsuccessful due to blood clots creating a "ball-valve" effect which occlude the various distal openings of the catheter.

When occlusion of the various distal openings of the catheter occurs due to the above described blood clot attachment and build-up, a physician has several options for eliminating the occlusion thereby reestablishing access to the vascular system. One option is to remove the occluded catheter and replace it with a new catheter. However, in contrast to the ease of exchanging a catheter which was placed in the patient's body using the direct puncture technique, exchanging a catheter which was placed in the patient's body using the tunneled catheter technique is substantially more complicated and invasive. This is true since in order to remove the occluded catheter from the patient's body, the physician must surgically dissect the tissue ingrowth member which is secured to the outer surface of the catheter from the patient's subcutaneous tissue. Recall that the tissue ingrowth member becomes affixed to the subcutaneous tissue over a period of time. Thereafter, the physician would place a new catheter into the patient's body generally using the above described tunneled catheter technique. Thus, this option is undesirable since it requires additional surgery which further traumatizes the patient and increases the cost of the medical care.

Another option for eliminating the occlusion of the various distal openings of the catheter in order to reestablish access to the vascular system involves the performance of a medical procedure in which a blood clot-dissolving medication such as urokinase is infused into the catheter. However, this medication is not always successful in eliminating the occlusion of the various distal openings of the catheter. In addition, infusion of the medication into the catheter subjects the patient to potential bleeding complications due to the medication entering the vascular system and being circulated systemically. Further, this medication is expensive. Thus, this option has serious drawbacks as well.

An additional option for eliminating the occlusion of the various distal openings of the catheter in order to reestablish access to the vascular system involves the performance of a medical procedure in which an intravascular snare is introduced into the blood vessel in order to physically strip off any blood clots or fibrin sheath which has attached and built-up on the distal portion of the catheter. However, for catheters placed in veins, this medical procedure requires a venopuncture in the femoral or jugular vein which is invasive and can be uncomfortable for a patient. Furthermore, this option requires the use of (i) an intravascular snare, (ii) a physician experienced in catheter techniques, and (iii) an angiographic suite to provide fluoroscopic imaging. Use of each of items (i), (ii), and (iii) above causes this option to be relatively expensive. Consequently, this option also has significant disadvantages.

What is needed therefore is a method and apparatus for eliminating the occlusion of the various distal openings of a catheter which has been placed in a patient's body using the tunneled catheter technique which overcomes one or more of the above-mentioned drawbacks.

SUMMARY OF THE INVENTION

In accordance with one embodiment of the present invention, there is provided a subcutaneous port catheter system. The catheter system includes a reservoir defining a chamber therein. The catheter system further includes a guide catheter attached to the reservoir, the guide catheter having a guide lumen and a distal guide orifice. Moreover, the catheter system includes an inner catheter attached to the reservoir, the inner catheter being positioned within the guide lumen and extending through the distal guide orifice.

Pursuant to another embodiment of the present invention, there is provided a subcutaneous port catheter system which includes a reservoir having a septum and defining a chamber. The catheter system further includes an inner catheter that is in fluid communication with the chamber. Also, the catheter system includes a guide catheter having a guide lumen, the inner catheter being at least partially positioned within the guide lumen.

According to yet another embodiment of the present invention, there is provided a method of advancing fluid into a blood vessel of a body of a patient. The method includes implanting a port catheter system beneath the skin of the body so that a guide catheter and an original inner catheter of the port catheter system are both at least partially positioned within the blood vessel, the original inner catheter being located at least partially within the guide catheter. The method also includes advancing a needle through a septum of a reservoir of the port catheter system after the implanting step so as to position a distal end of the needle within a chamber of the reservoir. In addition, the method includes infusing fluid into or withdrawing fluid from the blood vessel through the needle, the reservoir, and the original inner catheter after the advancing step.

It is therefore an object of the present invention to provide a new and useful subcutaneous port catheter system and associated method for use in a body of a patient.

It is another object of the present invention to provide an improved subcutaneous catheter system and associated method for use in a body of a patient.

It is yet another object of the present invention to provide a new and useful long-term dialysis catheter system for use in a body of a patient.

It is another object of the present invention to provide an improved long-term dialysis catheter system for use in a body of a patient.

It is a further object of the present invention to provide a new and useful method of maintaining blood flow in a long-term dialysis catheter system.

It is still another object of the present invention to provide an improved method of maintaining blood flow in a long-term dialysis catheter system.

It is additionally another object of the present invention to provide a long-term dialysis catheter system and an associated method which is relatively less invasive in order to remove and replace an associated dialysis catheter.

It is further another object of the present invention to provide a long-term dialysis catheter system and an associated method which is relatively less expensive in order to remove and replace an associated dialysis catheter.

It is moreover another object of the present invention to provide a long-term dialysis catheter system and an associated method which is relatively safer in order to remove and replace an associated dialysis catheter.

It is yet another object of the present invention to provide a long-term dialysis catheter system and an associated method which is relatively less complicated in order to remove and replace an associated dialysis catheter.

It is further another object of the present invention to provide a long-term dialysis catheter system and an associated method which is relatively less traumatic in order to remove and replace an associated dialysis catheter.

It is still another object of the present invention to provide a long-term dialysis catheter system and an associated method which does not require the infusion of a clot-dissolving medication such as urokinase into the patent's body in order to reestablish an appropriate level of fluid flow in an associated dialysis catheter.

It is yet another object of the present invention to provide a long-term dialysis catheter system and an associated method which does not require the use of an intravascular snare in order to reestablish an appropriate level of fluid flow in an associated dialysis catheter.

It is additionally another object of the present invention to provide a long-term dialysis catheter system and an associated method which does not require blood clot to be stripped off of the catheter with an intravascular snare in order to reestablish an appropriate level of fluid flow in an associated dialysis catheter.

Other objects and benefits of the present invention can be discerned from the following description and accompanying drawings.

BRIEF DESCRIPTION OF THE DRAWINGS

FIG. 16 is a side elevational view of the guide catheter of the catheter system shown in FIG. 15;

FIG. 17 is a side elevational view of the first original catheter of the catheter system shown in FIG. 15;

FIG. 18 is a side elevational view of the second original catheter of the catheter system shown in FIG. 15;

FIG. 21 is a side elevational view of the guide catheter of the catheter system shown in FIG. 20;

FIG. 22 is a side elevational view of the original catheter of the catheter system shown in FIG. 20;

FIG. 49 is an enlarged fragmentary elevational view of the catheter system of FIG. 48 showing a supplemental locking system;

FIGS. 49A, 49B, and 49C are various views of the locking clip of the supplemental locking system of FIG. 49 being applied over the finger grips;

FIG. 50 is an enlarged fragmentary elevational view of the catheter system of FIG. 48 showing an alternative supplemental locking system; and FIG. 50A is an enlarged cross sectional view of the first finger grip and slider taken along the line 50A—50A of FIG. 50C as viewed in the direction of the arrows (Note that the dialysis catheter is shown removed for clarity of description);

FIG. 50B is an enlarged cross sectional view of the first finger grip and slider taken along the line 50B—50B of FIG. 50 as viewed in the direction of the arrows (Note that the dialysis catheter is shown removed for clarity of description);

FIG. 50C is enlarged fragmentary elevational view of the catheter system of FIG. 50 showing an alternative view of the first and second finger grips;

FIG. 50D is an enlarged cross sectional view of the second finger grip and slider taken along the line 50D—50D of FIG. 50 as viewed in the direction of the arrows (Note that only the second finger grip and slider is shown for clarity of description);

DESCRIPTION OF THE PREFERRED EMBODIMENTS

Figure 1:
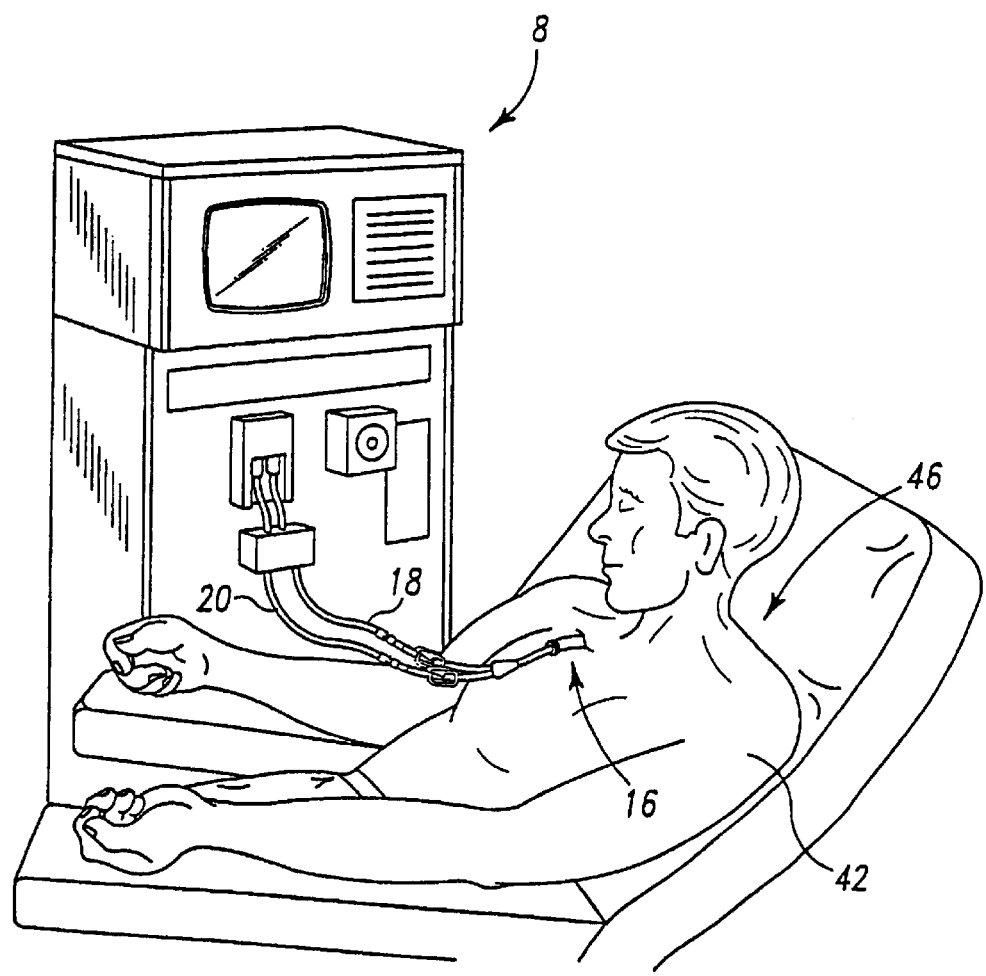
FIG. 1 is a perspective view of a patient undergoing a dialysis procedure utilizing the long-term dialysis catheter system of the present invention.

While the invention is susceptible to various modifications and alternative forms, specific embodiments thereof have been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

I. Catheter System 16

Referring now to FIG. 1, there is shown a hemodialysis machine 8 to which is attached a long-term dialysis catheter system 16 which incorporates the features of a first embodiment of the present invention therein. The catheter system 16 is inserted in a patient's body 46. The hemodialysis machine 8 includes an inlet line 18 and an outlet line 20 which are each in fluid communication with the catheter system 16. The body 46 includes skin, generally indicated by the reference numeral 42. The body 46 further includes subcutaneous tissue 44 positioned below the skin 42 (see FIG. 7).

Figure 2:
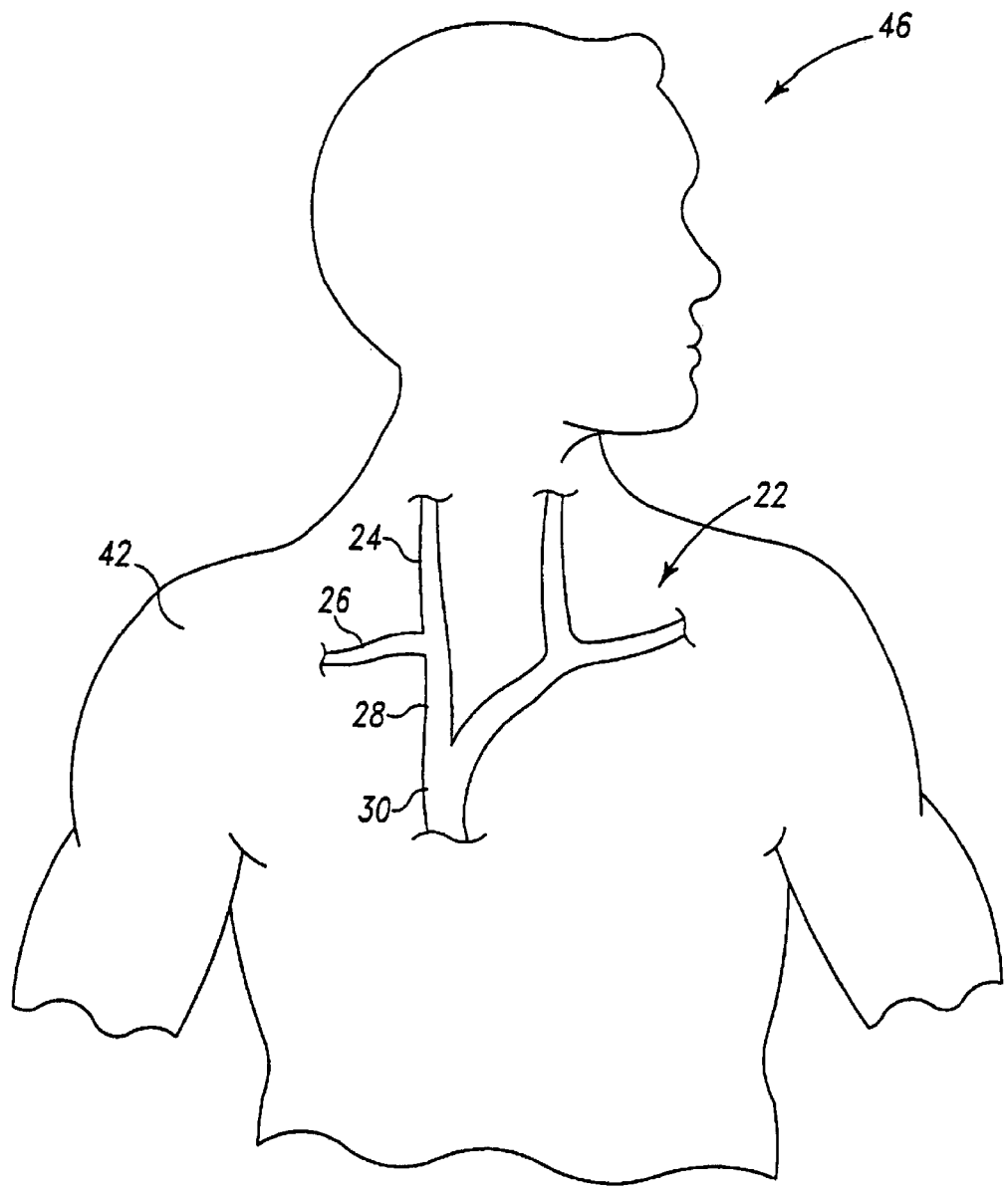
FIG. 2 is a schematic view of a portion of the vascular system of the patient of FIG. 1, showing the right internal jugular vein, the right subclavian vein, the right innominate vein, and the superior vena cava.

As shown in FIG. 2, the body 46 further includes a vascular system 22. The vascular system 22 includes a right internal jugular vein 24, a right subclavian vein 26, a right innominate vein 28, and a superior vena cava 30. Note that the vascular system 22 is positioned within the body 46 underneath the skin 42. However, the vascular system 22, including the right internal jugular vein 24, the right subclavian vein 26, the right innominate vein 28, and the superior vena cava 30, are depicted in FIGS. 2 and 7–10 (and also in FIGS. 11, 30, 34 and 38) with solid lines for clarity of description.

Figure 3:
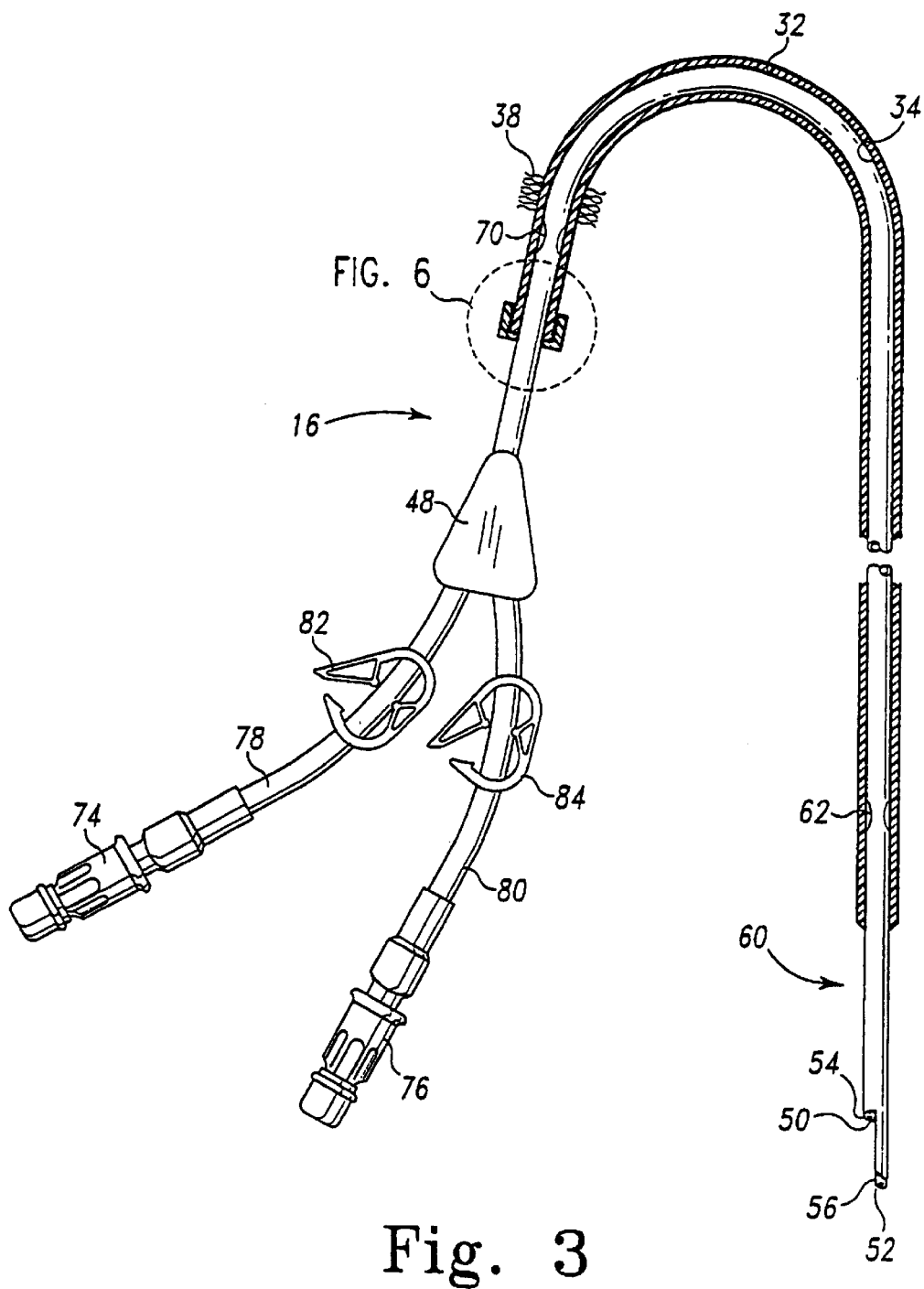
FIG. 3 is an enlarged side elevational view of the long-term dialysis catheter system of FIG. 1, showing the original dialysis catheter positioned within the guide lumen of the guide catheter.

The catheter system 16 is shown in more detail in FIG. 3. In particular, the catheter system includes a guide catheter 32 having a guide lumen 34 which extends the entire length thereof (see also FIGS. 4A–4D). The guide lumen 34 defines a proximal guide orifice 35 and a distal guide orifice 36.

Figure 4A:
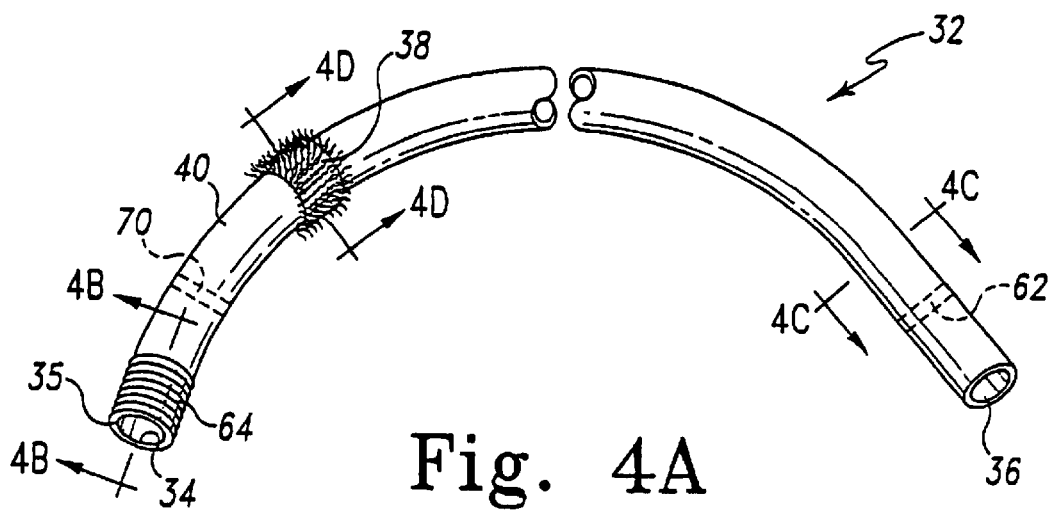
FIG. 4A is an enlarged side elevational view of the guide catheter of the long-term dialysis catheter system shown in FIG. 1.
Figure 4B:
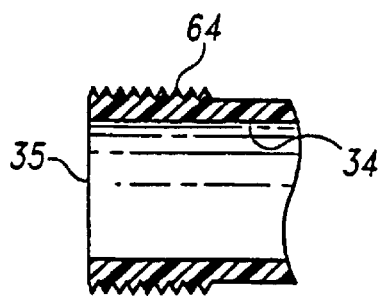
FIG. 4B is an enlarged fragmentary cross sectional view of the guide catheter taken along the line 4B—4B of FIG. 4A as viewed in the direction of the arrows.
Figure 4C:
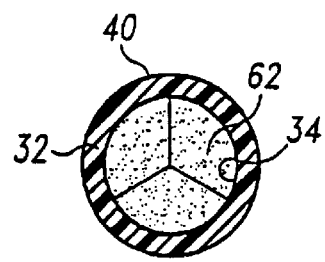
FIG. 4C is an enlarged cross sectional view of the guide catheter taken along the line 4C—4C of FIG. 4A as viewed in the direction of the arrows.
Figure 4D:
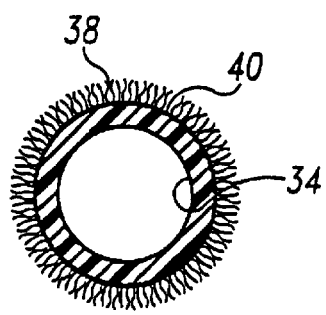
FIG. 4D is an enlarged cross sectional view of the guide catheter taken along the line 4D—4D of FIG. 4A as viewed in the direction of the arrows.

The catheter system 16 further includes a dialysis catheter 48 which is able to be positioned within the guide lumen 34 of the guide catheter 32 (see FIG. 4A). In addition, the catheter system 16 includes a dialysis catheter 58 which is also able to be positioned within the guide lumen 34 of the guide catheter 32 (see FIG. 10). In particular, according to one preferred manner of using the catheter system 16 during a dialysis session, the dialysis catheter 48 is positioned within the guide lumen 34 of the guide catheter 32 for a period of time during which blood is infused and withdrawn therethrough. After the period of time, the blood flow through the lumens of the dialysis catheter 48 may become partially or even totally inhibited due to blood clot build-up. In order to remedy this problem, the dialysis catheter 48 is withdrawn from the guide lumen 34 of the guide catheter 32, and thereafter, the dialysis catheter 58 is positioned within the guide lumen 34 of the guide catheter 32 for a subsequent period of time during which blood is infused and withdrawn therethrough. Since the dialysis catheter 48 is originally used in the catheter system 16 and thereafter replaced with the dialysis catheter 58, the dialysis catheter 48 may be characterized as an "original catheter" and the dialysis catheter 58 may be characterized as a "replacement catheter".

Referring again to FIGS. 4A–4D, the guide catheter 32 also includes an outer surface 40 having a tissue ingrowth member 38 secured thereto. Tissue ingrowth member 38 is configured to facilitate fibrous tissue growth therein. More specifically, the subcutaneous tissue 44 of body 46 becomes affixed to the tissue ingrowth member 38 when the tissue ingrowth member 38 remains in contact with the subcutaneous tissue 44 over a period of time. One type of tissue ingrowth member which may be used as the tissue ingrowth member 38 is a DACRON cuff which is available from Bard Access Systems of Salt Lake City, Utah.

The guide catheter 32 further includes a first locking component 64 defined on a proximal end portion thereof. The first locking component 64 includes external threads which cooperate with an internally threaded cap 67 of dialysis catheter 48 to lock the dialysis catheter 48 to the guide catheter 32 as will be discussed in more detail below.

The guide catheter 32 further includes a distal blood flow valve 62 and a proximal blood flow valve 70 positioned within the guide lumen 34. The blood flow valves 62 and 70 are configured to prevent fluid communication between the proximal guide orifice 35 and the distal guide orifice 36 through the guide lumen 34 when neither the dialysis catheter 48 nor the dialysis catheter 58 are positioned within the guide lumen 34. In addition, when either the dialysis catheter 48 or the dialysis catheter 58 is positioned within the guide lumen 34, the blood flow valves 62 and 70 function to prevent blood and/or air leakage through a space defined between the outer surface of the dialysis catheter 48, 58 and the inner surface of the guide catheter 32.

One valve which may be used as either the distal blood flow valve 62 or the proximal blood flow valve 70 with some minor modifications is available from Micro Therapeutics, Inc. of San Clemente, Calif. under the trademark "Cragg MicroValve™".

Referring now to FIGS. 5A–5D, the dialysis catheter 48 includes an ingress lumen 50 and an egress lumen 52 defined therein. The ingress lumen 50 defines a distal ingress orifice 54. Similarly, the egress lumen 52 defines a distal egress orifice 56. The distal ingress orifice 54 and the distal egress orifice 56 are defined in a distal segment 60 of the dialysis catheter 48.

Figure 6:
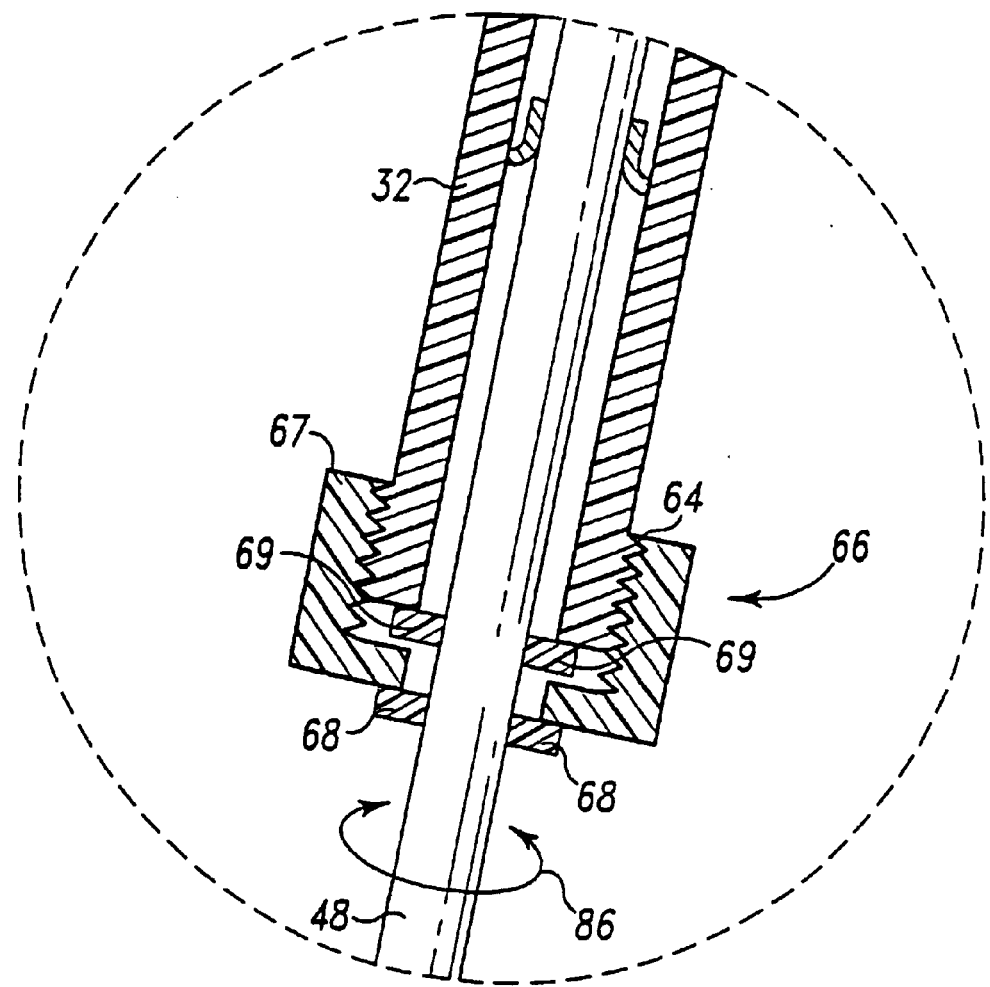
FIG. 6 is an enlarged view of a portion of FIG. 3 which is encircled and indicated as FIG. 6.

The dialysis catheter 48 also includes a second locking component 66 secured thereto. The second locking component 66 cooperates with the first locking component 64 to lock the dialysis catheter 48 to the guide catheter 32. In particular, the second locking component 66 includes the threaded cap 67 which has a hole extending therethrough as shown in FIG. 6. The dialysis catheter 48 may extend through the hole as also shown in FIG. 6. The second locking component 66 further includes an upper tab 68 and a lower tab 69 each which extends around and is secured to the outer surface of the dialysis catheter 48. The cap 67 is interposed between the upper tab 68 and the lower tab 69 so as to be retained therebetween. The threaded cap 67 is able to be rotated relative to the dialysis catheter in the directions indicated by arrow 86 in order to secure/release the dialysis catheter to/from the guide catheter.

While the first locking component 64 and the second locking component 66 have been described herein as functioning to lock the dialysis catheter 48 to the guide catheter 32 and has substantial benefits, numerous other arrangements may alternatively be incorporated into the dialysis system 16 to function to lock the dialysis catheter 48 to the guide catheter 32 and still achieve many of the advantages of the present invention.

For example, another locking arrangement which may be used to lock the dialysis catheter 48 to the guide catheter 32 is a detent and groove type locking arrangement (not shown). In particular, such a locking mechanism would include a circumferential groove which is defined in an outer surface of the dialysis catheter 48 (the sidewall of the dialysis catheter may need to possess an increased thickness in order to define such groove therein). A detent (e.g. a ball), supported by the guide catheter 32, may be spring biased into the groove so as to lock the dialysis catheter 48 in relation to the guide catheter 32. When desired, the detent may be allowed to advance out of the groove. Thereafter, when the detent is positioned out of the groove, the dialysis catheter may be withdrawn from the guide lumen 34 of the guide catheter 32. Examples of detent and groove type locking arrangements which may be used with some modifications to lock the dialysis catheter 48 to the guide catheter 32 are disclosed in U.S. Pat. Nos. 4,900,202 and 5,013,194 each issued to Wienhold, and U.S. Pat. Nos. 5,470,180 and 5,779,404 each issued to Jore, the disclosures of each of these four U.S. Patents being hereby incorporated by reference.

Yet another example of a locking arrangement which may be used to lock the dialysis catheter 48 to the guide catheter 32 is a leg and guide channel type locking arrangement (not shown). In particular, such a locking arrangement would include a short leg extending from an outer surface of the dialysis catheter 48. The leg would be fixed in relation to the dialysis catheter 48. The locking arrangement would further include a guide channel defined in a sidewall of the guide catheter 32. The guide channel would extend longitudinally for a short distance (e.g. a few centimeters) along the length of the guide catheter 32. At the distal end of the guide channel, there would exist a narrowed distal channel portion of reduced width. In operation, the leg would be positioned in the guide channel. If it would be desirable to lock the dialysis catheter 48 in relation to the guide catheter 32, the dialysis catheter 48 could be advanced distally in relation to the guide catheter 32 until the leg became wedged within the narrowed distal channel portion. A secondary safety latch may be employed to retain the leg in the narrowed distal channel portion.

The dialysis catheter 48 further includes an egress line 78 and an ingress line 80. The egress line 78 is in fluid communication with the egress lumen 52, while the ingress line 80 is in fluid communication with the ingress lumen 50. The egress line 78 has an adapter or injection cap 74 attached thereto, and the ingress line 80 has an adapter or injection cap 76 attached thereto.

Figure 5A:
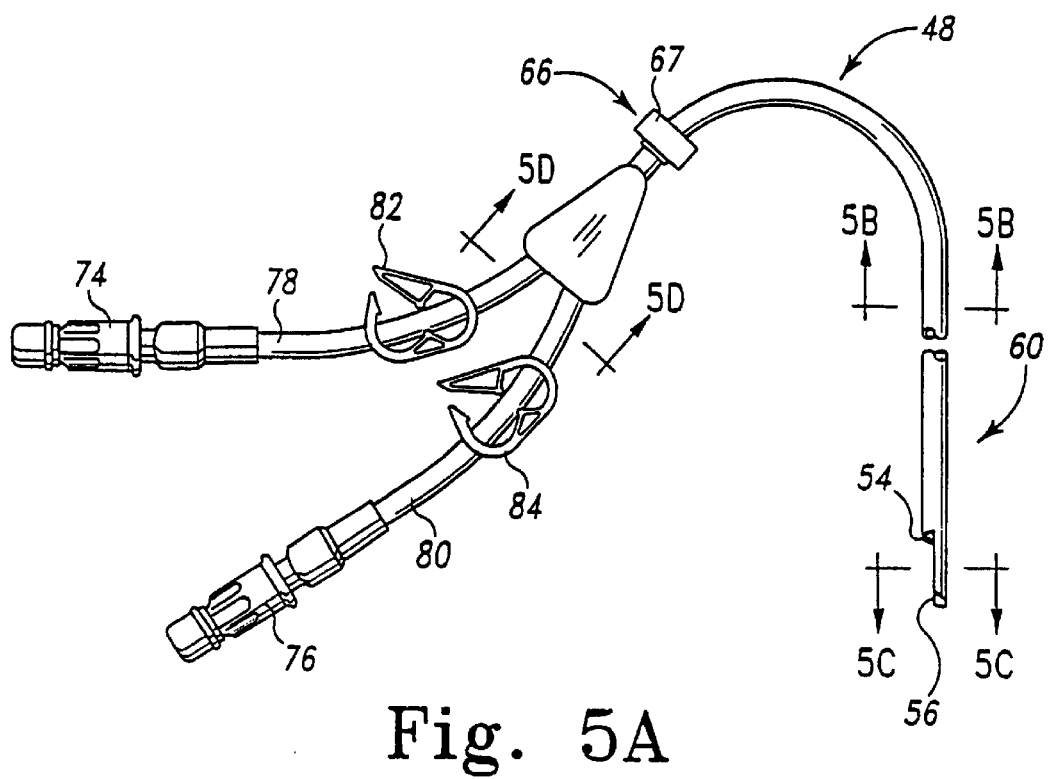
FIG. 5A is an enlarged side elevational view of the original dialysis catheter of the long-term dialysis catheter system shown in FIG. 1.
Figure 5B:
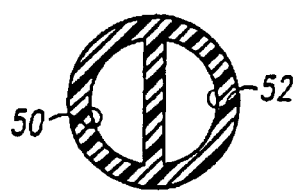
FIG. 5B is an enlarged cross sectional view of the original dialysis catheter taken along the line 5B—5B of FIG. 5A as viewed in the direction of the arrows.
Figure 5C:
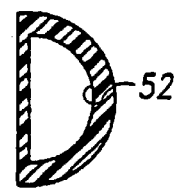
FIG. 5C is an enlarged cross sectional view of the original dialysis catheter taken along the line 5C—5C of FIG. 5A as viewed in the direction of the arrows.
Figure 5D:
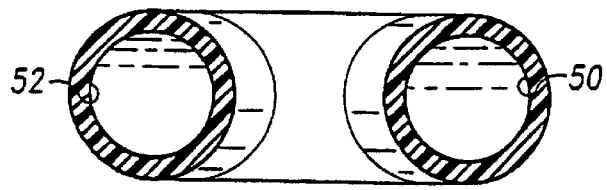
FIG. 5D is an enlarged cross sectional view of the original dialysis catheter taken along the line 5D—5D of FIG. 5A as viewed in the direction of the arrows.

In addition, a clamp 82 is positioned on the egress line 78, while a clamp 84 is positioned on the ingress line 80 as shown in FIG. 5A. It should be understood that closure of the clamp 82 causes fluid communication between adapter 74 and original distal egress orifice 56 to be prevented. Similarly, closure of the clamp 84 prevents fluid communication between the adapter 76 and the distal ingress orifice 54.

The dialysis catheter 48 may be positioned within the guide lumen 34 of the guide catheter 32 as shown in FIG. 3. When the dialysis catheter 48 is positioned within the guide lumen 34 as shown in FIG. 3, the dialysis catheter is said to be positioned in an "inserted position." When the dialysis catheter 48 is entirely removed from the guide lumen 34, the dialysis catheter is said to be positioned in a "removed position."

When the dialysis catheter 48 is positioned in the inserted position, the distal segment 60 of the dialysis catheter 48 extends out of the distal guide orifice 36 of the guide catheter 32. Accordingly, the distal ingress orifice 54 and the distal egress orifice 56 are each positioned outside of guide lumen 34 when the dialysis catheter 48 is located in the inserted position. Moreover, when the dialysis catheter 48 is located in the inserted position, the threaded cap 67 is positioned adjacent to the first locking component 64 such that the threaded cap 67 can be rotated relative to guide catheter 32 so as to lock the second locking component 66 to the first locking component 64. Note that locking the second locking component 66 to the first locking component 64 in the above described manner locks the dialysis catheter 48 to the guide catheter 32.

Figure 8:
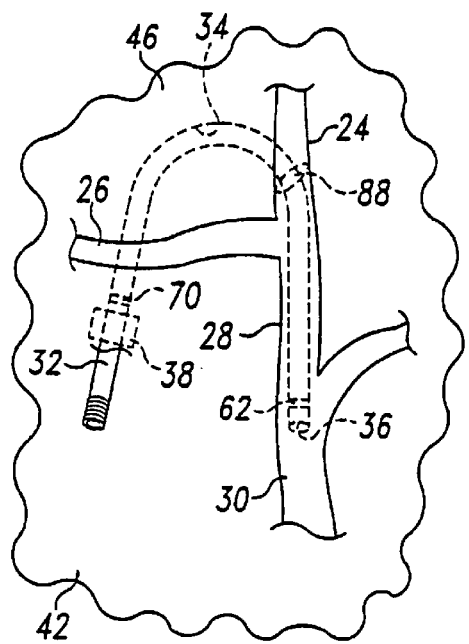
FIG. 8 is a reduced view which is similar to FIG. 7, but showing the original dialysis catheter removed from the guide lumen of the guide catheter.
Figure 9:
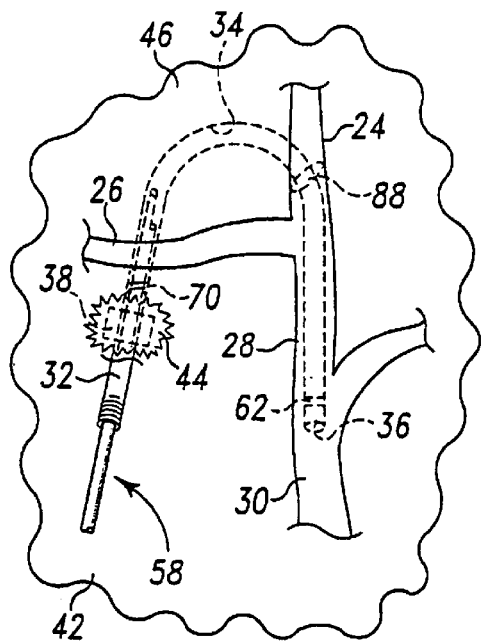
FIG. 9 is a view similar to FIG. 8, but showing a replacement dialysis catheter partially inserted into the guide lumen of the guide catheter.
Figure 10:
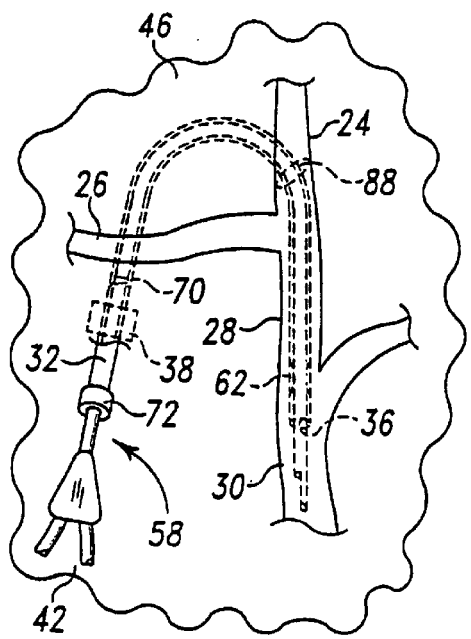
FIG. 10 is a view similar to FIG. 9, but showing the replacement dialysis catheter fully inserted into the guide lumen of the guide catheter.

Referring now to FIGS. 8–10, the structure and use of the dialysis catheter 58 will be described. The dialysis catheter 58 is substantially similar to the dialysis catheter 48. In particular, the dialysis catheter 58 includes an ingress lumen and an egress lumen defined therein. The ingress lumen defines a distal ingress orifice. Similarly, the egress lumen defines a distal egress orifice. The distal ingress orifice and the distal egress orifice are defined in a distal segment of the dialysis catheter 58.

The dialysis catheter 58 also includes a third locking component 72 secured thereto (see FIG. 10). The third locking component 72 cooperates with the first locking component 64 to lock the dialysis catheter 58 to the guide catheter 32. In particular, the third locking component 72 includes a threaded cap which has a hole extending therethrough. The dialysis catheter 58 may extend through the hole as also shown in FIG. 10. The third locking component 72 further includes an upper tab and a lower tab each which extends around and is secured to the outer surface of the dialysis catheter 58. The threaded cap is interposed between the upper tab and the lower tab so as to be retained therebetween. The threaded cap is able to be rotated relative to the dialysis catheter in order to secure/release the dialysis catheter 58 to/from the guide catheter 32.

The dialysis catheter 58 further includes an egress line and an ingress line. The egress line is in fluid communication with the egress lumen, while the ingress line is in fluid communication with the ingress lumen. The egress line has an adapter attached thereto, and the ingress line has another adapter attached thereto. In addition, a clamp may be positioned on the egress line, while another clamp may positioned on the ingress line. It should be understood that closure of the above-identified clamps cause fluid communication between the above adapters and the above distal egress orifice and distal ingress orifice to be prevented.

The dialysis catheter 58 may be positioned within the guide lumen 34 of the guide catheter 32 as shown in FIG. 10. When the dialysis catheter 58 is positioned within the guide lumen 34 as shown in FIG. 10, the dialysis catheter is said to be positioned in an "inserted position." When the dialysis catheter 58 is entirely removed from the guide lumen 34, the dialysis catheter 58 is said to be positioned in a "removed position."

When the dialysis catheter 58 is positioned in the inserted position, a distal segment of the dialysis catheter 58 extends out of the distal guide orifice 36 of the guide catheter 32. Accordingly, the distal ingress orifice and the distal egress orifice of the dialysis catheter 58 are each positioned outside of guide lumen 34 when the dialysis catheter 58 is located in the inserted position. Moreover, when the dialysis catheter 58 is located in the inserted position, the threaded cap is positioned adjacent to the first locking component 64 such that the threaded cap can be rotated relative to guide catheter 32 so as to lock the third locking component 72 to the first locking component 64. Note that locking the third locking component 72 to the first locking component 64 in the above described manner locks the dialysis catheter 58 to the guide catheter 32.

The guide catheter 32 is placed within the body 46 using the tunneled catheter technique. In particular, a first opening is created by making a small incision in the skin 42 with a scalpel directly over the right internal jugular vein 24. Thereafter, the right internal jugular vein 24 is punctured to create a venotomy 88 at a location directly below the first opening by advancing a needle through the skin incision and the subcutaneous tissue 44 and into the right internal jugular vein 24. Thereafter, a guidewire is advanced through the needle into the right internal jugular vein 24 through the venotomy 88. The needle is then removed over the guidewire. One or more tubular vessel dilators is passed over the guidewire to widen the opening defined in the skin 42 and subcutaneous tissue 44, and further to widen the venotomy 88 defined in the wall of the right internal jugular vein 24 to a caliber similar to that of the tubular guide. Thereafter, the tubular guide is advanced over the guidewire and into the right internal jugular vein 24. Then, a second opening is created in the skin 42 which is spaced apart at least several centimeters from the first opening. A tunneling instrument is advanced from the second opening to the first opening so as to create a passageway within the subcutaneous tissue 44 under the skin 42 between the first opening and the second opening. The guide catheter 32 is then advanced into the second opening and through the passageway such that a distal end of the guide catheter 32 is located adjacent the first opening. The distal end of the guide catheter 32 is then inserted through the tubular guide member and into the right internal jugular vein 24 so that the tissue ingrowth member 38 is positioned in the subcutaneous tissue 44. Thereafter, the tubular guide member is removed. The first opening is then closed with suture whereby the guide catheter 32: (a) is no longer exposed through the first opening, (b) extends for at least several centimeters under the skin 42 between the second opening and the venotomy 88, and (c) extends out of the second opening so that the proximal end of the guide catheter 32 is located outside of the body 46.

Figure 7:
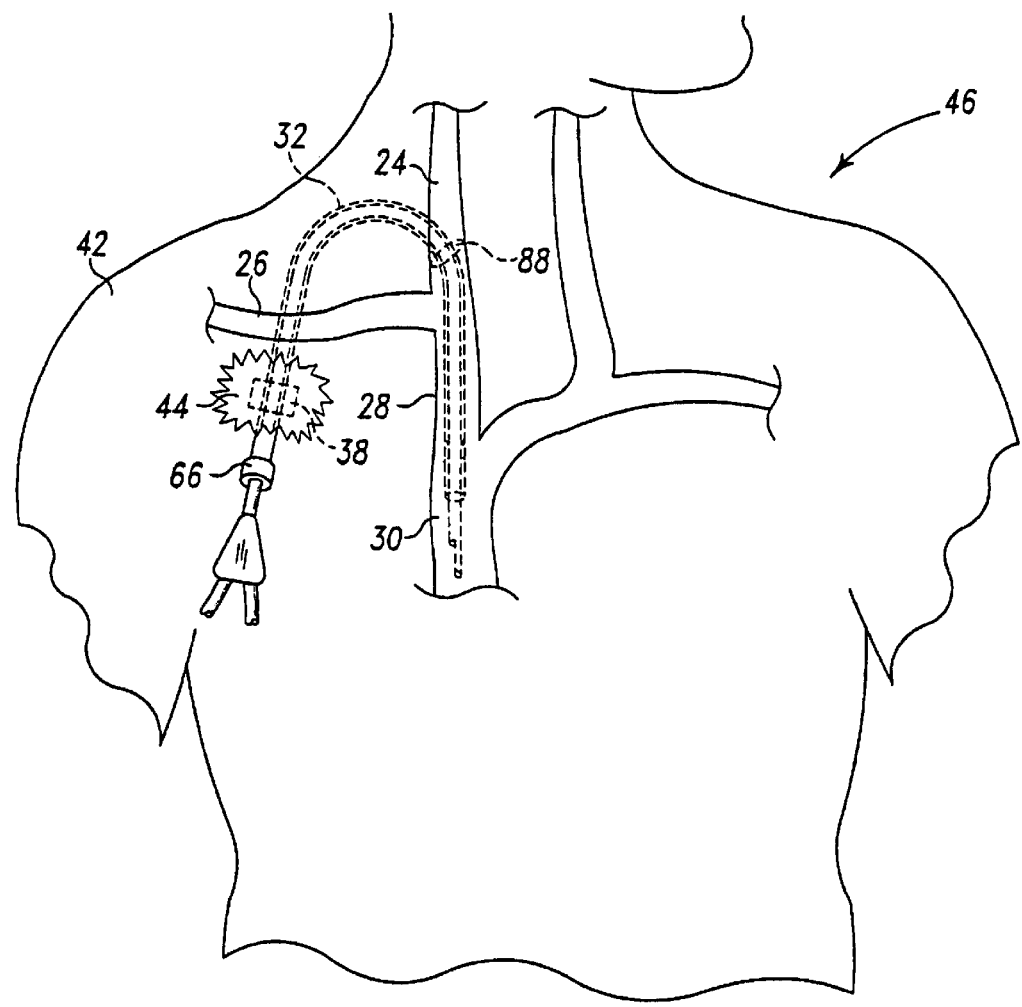
FIG. 7 is an enlarged view which is similar to FIG. 2, but showing the long-term dialysis catheter system of FIG. 3 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Note that after the guide catheter 32 is placed in the vascular system 22 as described above, the guide catheter 32 is positioned in the right internal jugular vein 24, the right innominate vein 28, and the superior vena cava 30 as shown in FIG. 7. Moreover, note that as the tissue ingrowth member 38 remains in contact with the subcutaneous tissue 44 over a period of time, the subcutaneous tissue 44 becomes affixed to the tissue ingrowth member 38 thereby securing the guide catheter 32 to the body 46. As discussed above, affixation of the tissue ingrowth member 38 to the subcutaneous tissue 44 in the above described manner helps prevent bacterial migration up the guide catheter 32 from the second opening to the venotomy 88 thereby preventing serious infection.

Once the guide catheter 32 is placed in the body 46 as described above, the dialysis catheter 48 is advanced through the guide lumen 34 of the guide catheter 32 so that the distal ingress orifice 54 and the distal egress orifice 56 are advanced out of the distal guide orifice 36 and positioned within the superior vena cava 30 as shown in FIG. 7. (In other words, the dialysis catheter 48 is advanced to its inserted position.) The dialysis catheter 48 is then locked to guide catheter 32 utilizing the first locking component 64 and the second locking component 66 in the above described manner.

I(a). First Manner of Using Catheter System 16

According to a first preferred manner of using the catheter system 16 (see FIG. 3), the original dialysis catheter 48 is replaced only after the dialysis catheter 48 becomes substantially inoperative due to partial or total occlusion of either or both of its lumens 50, 52 due to blood clot build-up.

In particular, when a patient desires to be dialyzed (i.e. engage in a dialysis session), egress line 78 and ingress line 80 are respectively connected to the inlet line 18 and the outlet line 20 of the hemodialysis machine 8 as shown in FIG. 1. A dialysis procedure is then performed on the patient's body 46 in a well known manner. Upon completion of the dialysis procedure, the egress line 78 and ingress line 80 are respectively disconnected from the inlet line 18 and the outlet line 20, and the patient is able to carry on about his/her business. Thereafter, when a patient desires to be dialyzed again, the above procedure is repeated. After a number of dialysis sessions, the lumens of the dialysis catheter 48 may become partially or even totally occluded due to blood clot build-up. In order to remedy this problem prior to continuing the dialysis sessions, the dialysis catheter 48 may be replaced with the dialysis catheter 58. In particular, the dialysis catheter 48 is unlocked from the guide catheter 32 and withdrawn from the guide lumen 34. Then, the dialysis catheter 58 is positioned within the guide lumen 34 of the guide catheter 32, and locked to the guide catheter 32. Thereafter, the dialysis sessions may be continued.

It should be understood that the blood flow valves 62 and 70 prevent blood from escaping through guide lumen 34 after the dialysis catheter 48 has been removed from the guide catheter 32 and before the dialysis catheter 58 is inserted into the guide catheter. Note also that the blood flow valves 62 and 70 also prevent air from entering the vascular system 22 through the guide lumen 34 after the dialysis catheter 48 has been removed from the guide catheter 32 and before the dialysis catheter 58 is inserted into the guide catheter.

It should further be appreciated that during a dialysis session when either the dialysis catheter 48 or the dialysis catheter 58 is positioned within the guide catheter 32, the blood flow valves 62 and 70 function to prevent blood and/or air leakage through a space defined between the outer surface of the dialysis catheter 48, 58 and the inner surface of the guide catheter 32.

I(b). Second Manner of Using Catheter System 16

An alternative manner of using the catheter system 16 will be described. In particular, according to a second preferred manner of using the catheter system 16, the original dialysis catheter 48 is a "single use" catheter. In other words, the original dialysis catheter 48 is only used for a single dialysis session, and thereafter discarded. Hence, the dialysis catheter 48 would typically never be left in the vascular system 22 long enough to become substantially inoperative due to partial or total occlusion of either or both of its lumens 50, 52 due to blood clot build-up.

Figure 11:
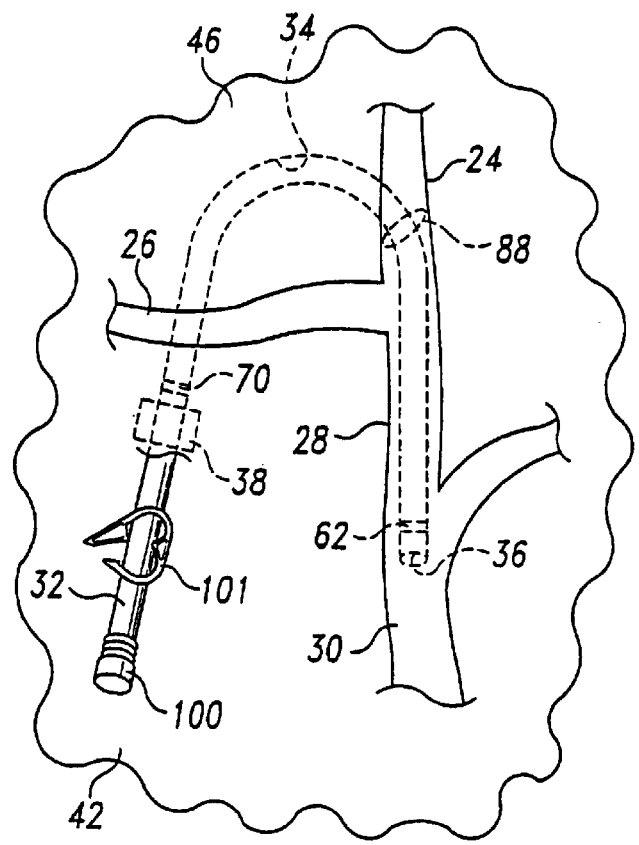
FIG. 11 is a view similar to FIG. 8, but showing neither the original dialysis catheter nor the replacement dialysis catheter inserted into the guide lumen of the guide catheter, but rather showing a closure member secured to the guide catheter so as to cover its proximal guide orifice.
Figure 12:
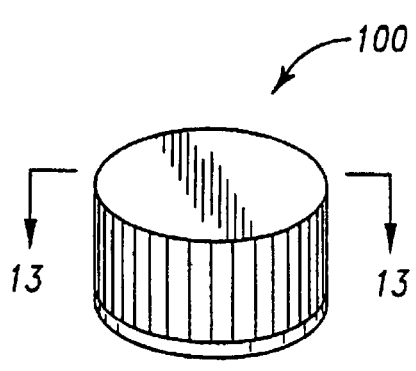
FIG. 12 is an enlarged perspective view of the closure member of FIG. 11.
Figure 13:
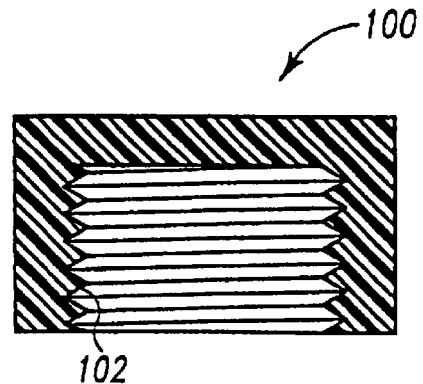
FIG. 13 is an enlarged cross sectional view of the closure member of FIG. 12 taken along the line 13—13 of FIG. 12 as viewed in the direction of the arrows.

To facilitate use of the catheter system 16 according the second preferred manner, the catheter system 16 further includes a closure member 100, such as a cap, which is able to be secured to the guide catheter 32 so as to cover its proximal guide orifice 35 (see FIG. 11-13). The closure member 100 includes internal threads 102 which cooperates with the first locking component 64 so as to lock the closure member 100 to the guide catheter 32 as shown in FIG. 11. The closure member 100 remains locked to the guide catheter 32 in the above-described manner between dialysis sessions in order to prevent contaminants from advancing into the vascular system 22 via the guide lumen 34. The closure member 100 also prevents blood from escaping through guide lumen 34, as well as, air from entering the vascular system 22 through guide lumen 34. Note that the blood flow valves 62 and 70 also function for similar preventative purposes. Optionally, a clamp 101 may also be positioned on the proximal end portion of the guide catheter 32 as shown in FIG. 11 for similar preventative purposes. The clamp 101 is substantially identical in construction and function to the clamps 82, 84 discussed hereinabove.

While cooperation between the internal threads 102 of the closure member 100 and the external threads of the first locking component 64 function to lock the closure member 100 to the guide catheter 32 and has substantial benefits, numerous other types of locking arrangements may alternatively be incorporated into the dialysis system 16 to function to lock the closure member 100 to the guide catheter 32. For example, a detent and groove type locking arrangement which is somewhat similar to the detent and groove type locking arrangement described above with respect to locking the dialysis catheter 48 to the guide catheter 32 may be used. Moreover, for example, a leg and guide channel type locking arrangement which is somewhat similar to the leg and guide channel type locking arrangement described above with respect to locking the dialysis catheter 48 to the guide catheter 32 may also be used.

Thus, according to this alternative manner of using the catheter system 16, when a patient desires to be dialyzed (i.e. engage in a dialysis session), the guide catheter 32 is prepped in a sterile manner such as by applying an antibacterial solution thereto. Thereafter, the closure member 100 is unlocked from the guide catheter 32. In particular, the closure member 100 is rotated in relation to the guide catheter 32 until the closure member becomes separated from the guide catheter. Thereafter, the dialysis catheter 48 is advanced through the guide lumen 34 of the guide catheter 32 so that the distal ingress orifice 54 and the distal egress orifice 56 are advanced out of the distal guide orifice 36 and positioned within the superior vena cava 30 as shown in FIG. 7. (In other words, the dialysis catheter 48 is advanced to its inserted position.) The dialysis catheter 48 is then locked to guide catheter 32 utilizing the first locking component 64 and the second locking component 66 in the above described manner.

Then, the egress line 78 and ingress line 80 are respectively connected to the inlet line 18 and the outlet line 20 of the hemodialysis machine 8 as shown in FIG. 1. A dialysis procedure is then performed on the patient's body 46 in a well known manner. Upon completion of the dialysis procedure, the egress line 78 and ingress line 80 are respectively disconnected from the inlet line 18 and the outlet line 20. Thereafter, the dialysis catheter 48 is withdrawn from the guide lumen 34 of the guide catheter 32 and then discarded. After such withdrawal, the closure member 100 is secured to the guide catheter 32 in the manner described above so as to cover its proximal guide orifice 35, and the patient is thereafter able to carry on about his/her business.

Then, when the patient desires to be dialyzed again (i.e. engage in a dialysis session), the guide catheter 32 is prepped in a sterile manner such as by applying an antibacterial solution thereto. Thereafter, the closure member 100 is unlocked from the guide catheter 32. Then, the dialysis catheter 58 is advanced through the guide lumen 34 of the guide catheter 32 so that its distal ingress orifice and its distal egress orifice are advanced out of its distal guide orifice and positioned within the superior vena cava 30 as shown in FIG. 10. The dialysis catheter 58 is then locked to guide catheter 32 utilizing its first locking component and the second locking component 64 in the above described manner. Subsequently, its egress line and its ingress line are respectively connected to the inlet line 18 and the outlet line 20 of the hemodialysis machine 8 as shown in FIG. 1. Another dialysis procedure is then performed on the patient's body 46 in a well known manner. Upon completion of the dialysis procedure, its egress line and its ingress line are respectively disconnected from the inlet line 18 and the outlet line 20. Thereafter, the dialysis catheter 58 is withdrawn from the guide lumen 34 of the guide catheter 32 and then discarded. After such withdrawal, the closure member 100 (or a new closure member similar to closure member 100) is secured to the guide catheter 32 in the manner described above so as to cover its proximal guide orifice 35, and the patient is again able to carry on about his/her business.

Please note that according to the second manner of using the catheter system 16, the dialysis catheters 48, 58 are only a "single use" catheter. Thus, the dialysis catheter is used during only a single dialysis session whereby the dialysis catheters 48, 58 contact the blood located in the vascular system 22 for only a relatively short period of time (e.g. four hours) during its useful life. Accordingly, the physical structure of the dialysis catheters 48, 58 may be substantially the same or similar to the physical structure of a conventional short-term catheter. For example, the thickness of the sidewalls of the dialysis catheters 48, 58 which define the ingress lumen (e.g. lumen 50) and the egress lumen (e.g. lumen 52) may be made to be substantially thinner than the thickness of the sidewalls which define the corresponding lumens of a conventional long-term dialysis catheter. This may help reduce the necessary magnitude of the outer diameter of the guide catheter 32 in which the dialysis catheter 48 is positionable.

I(c). Third Manner of Using Catheter System 16

Another alternative manner of using the catheter system 16 will be described. In particular, according to a third preferred manner of using the catheter system 16, the original dialysis catheter 48 is replaced with the replacement dialysis catheter 58, as described above, after an experimentally determined number of dialysis sessions is performed. For example, if experimental studies show that most dialysis catheters are operative after four dialysis sessions but become inoperative during or before a fifth dialysis session, then the original dialysis catheter 48 is replaced with the replacement dialysis catheter 58, as described above, after every fourth dialysis session is performed on a particular patient.

Or, if a certain patient has a history which indicates that his/her dialysis catheter will remain operative after three dialysis sessions but will become inoperative during or before a fourth dialysis session, then this particular patient would have his/her original dialysis catheter 48 replaced with a replacement dialysis catheter 58, as described above, after every three dialysis sessions are performed.

Obviously, whatever criteria is used, the original dialysis catheter 48 may be replaced with the replacement dialysis catheter 58, as described above, after any predetermined number of dialysis sessions are performed.

II. Catheter System 200

Figure 14:
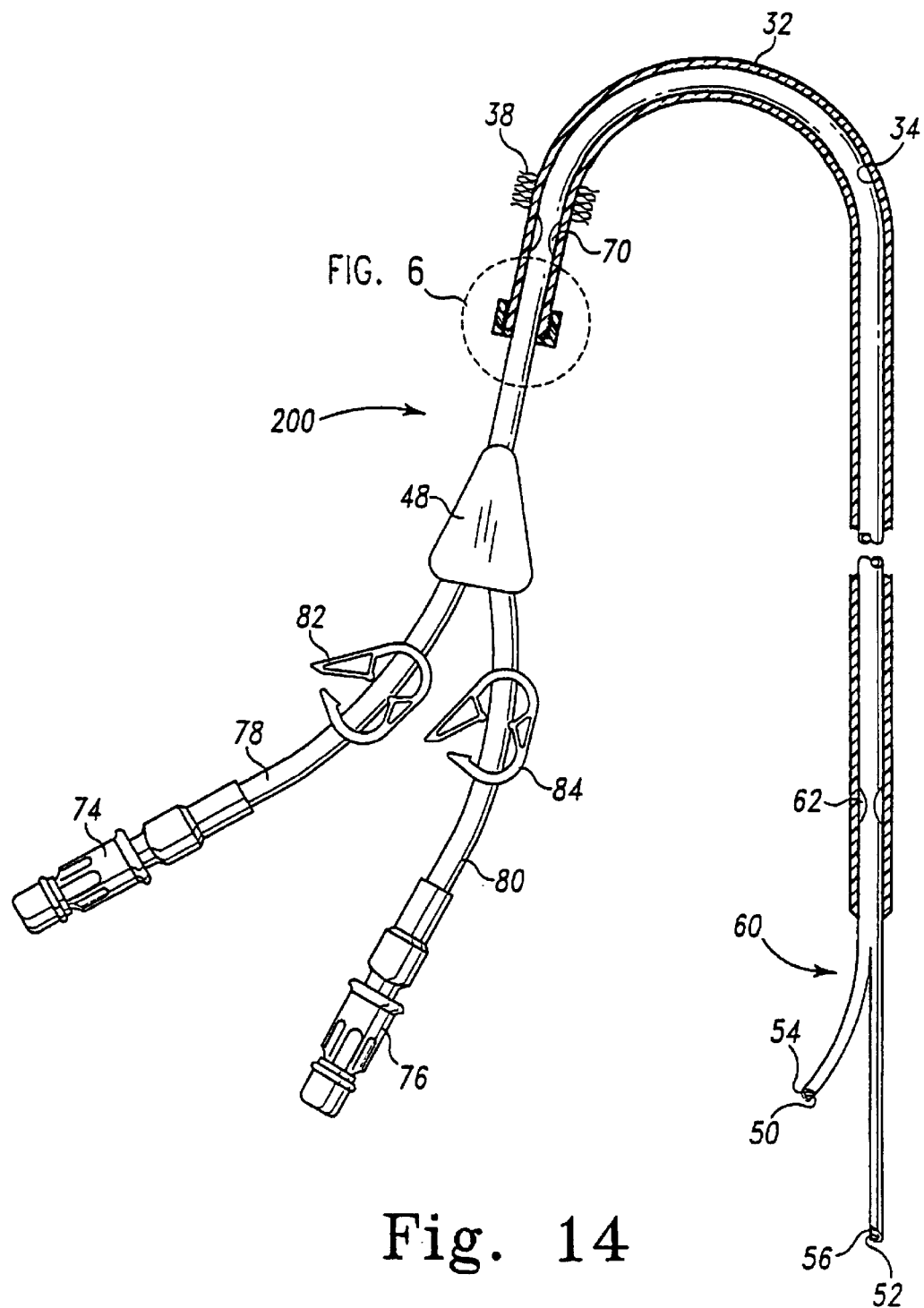
FIG. 14 is a view similar to FIG. 3, but showing another catheter system which incorporates the features of the present invention therein.

FIG. 14 shows a catheter system 200 which also incorporates the features of the present invention therein. The catheter system 200 is somewhat similar to the catheter system 16. Thus, the same reference numerals are used in FIG. 14 to designate common components which were previously discussed with regard to FIGS. 1–13. Moreover, the description of the components of the catheter system 200 which are common to the catheter system 16 will not be undertaken since they are designated with common reference numerals and such components have been previously described hereinabove. In addition, the guide catheter 32 of the catheter system 200 is placed within the body 46 in substantially the same manner as was described hereinabove with respect to the placement of the guide catheter 32 of the catheter system 16 within the body 46 (i.e. by the tunneled catheter technique).

However, the catheter system 200 differs from the catheter system 16 in that a portion of the distal segment 60 of the original dialysis catheter 48 which extends out of the distal guide orifice 36 of the guide catheter 32 is arranged in a bifurcated configuration as shown in FIG. 14. In particular, a distal portion of the ingress lumen 50 is arranged so as to gradually extend away from a distal portion of the egress lumen 52 as shown in FIG. 14. The catheter system 200 would also include a replacement dialysis catheter 58 which possesses the same physical construction and configuration as the original dialysis catheter 48 shown in FIG. 14.

The original dialysis catheter 48, shown in FIG. 14, possesses a distal portion configured somewhat similar to the distal portion of a dialysis catheter disclosed in an article entitled "Management of Hemodialysis Catheters" which was published in the July, 1999 edition of the periodical entitled "Applied Radiology" at pages 14–24 (authored by Haskel et al.), the disclosure of which is hereby incorporated by reference. Catheters having a distal portion configured in the above-described manner are sometimes referred to in the relevant medical art as "split-tip" catheters. For example, on page 20 of the Haskel article, a "split-tip" catheter is shown in FIG. 8.

II(a). First Manner of Using Catheter System 200

According to a first preferred manner of using the catheter system 200 (see FIG. 14), the original dialysis catheter 48 is replaced only after it becomes substantially inoperative due to partial or total occlusion of either or both of its lumens 50, 52 due to blood clot build-up. Such a manner of using the catheter system 200 would be substantially similar to the manner of using the catheter system 16 which was discussed herein in section 1(a) entitled "First Manner of Using Catheter System 16".

II(b). Second Manner of Using Catheter System 200

In accordance with a second preferred manner of using the catheter system 200, the original dialysis catheter 48 is a "single use" catheter. In other words, the original dialysis catheter 48 of catheter system 200 is only used for a single dialysis session, and thereafter discarded. Hence, the original dialysis catheter 48 would typically never be left in the vascular system 22 long enough to become substantially inoperative due to partial or total occlusion of either or both of its lumens 50, 52 due to blood clot build-up. Such a manner of using the catheter system 200 would be substantially similar to the manner of using the catheter system 16 which was discussed herein in section 1(b) entitled "Second Manner of Using Catheter System 16".

Also, please note that according to the second manner of using the catheter system 200, the original catheter 48 and the replacement catheter 58 are only a "single use" catheter. Accordingly, the physical structure of the catheters 48, 58 of the catheter system 200 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

II(c). Third Manner of Using Catheter System 200

According to a third preferred manner of using the catheter system 200, the original dialysis catheter 48 is replaced with the replacement dialysis catheter 58, as described above, after any predetermined number of dialysis sessions are performed. For example, such predetermined number may be (i) determined from experimental studies, (ii) determined based on patient history, or (iii) determined based on other criteria. Such a manner of using the catheter system 200 would be substantially similar to the manner of using the catheter system 16 which was discussed herein in section 1(c) entitled "Third Manner of Using Catheter System 16".

III. Catheter System 300

Figure 15:
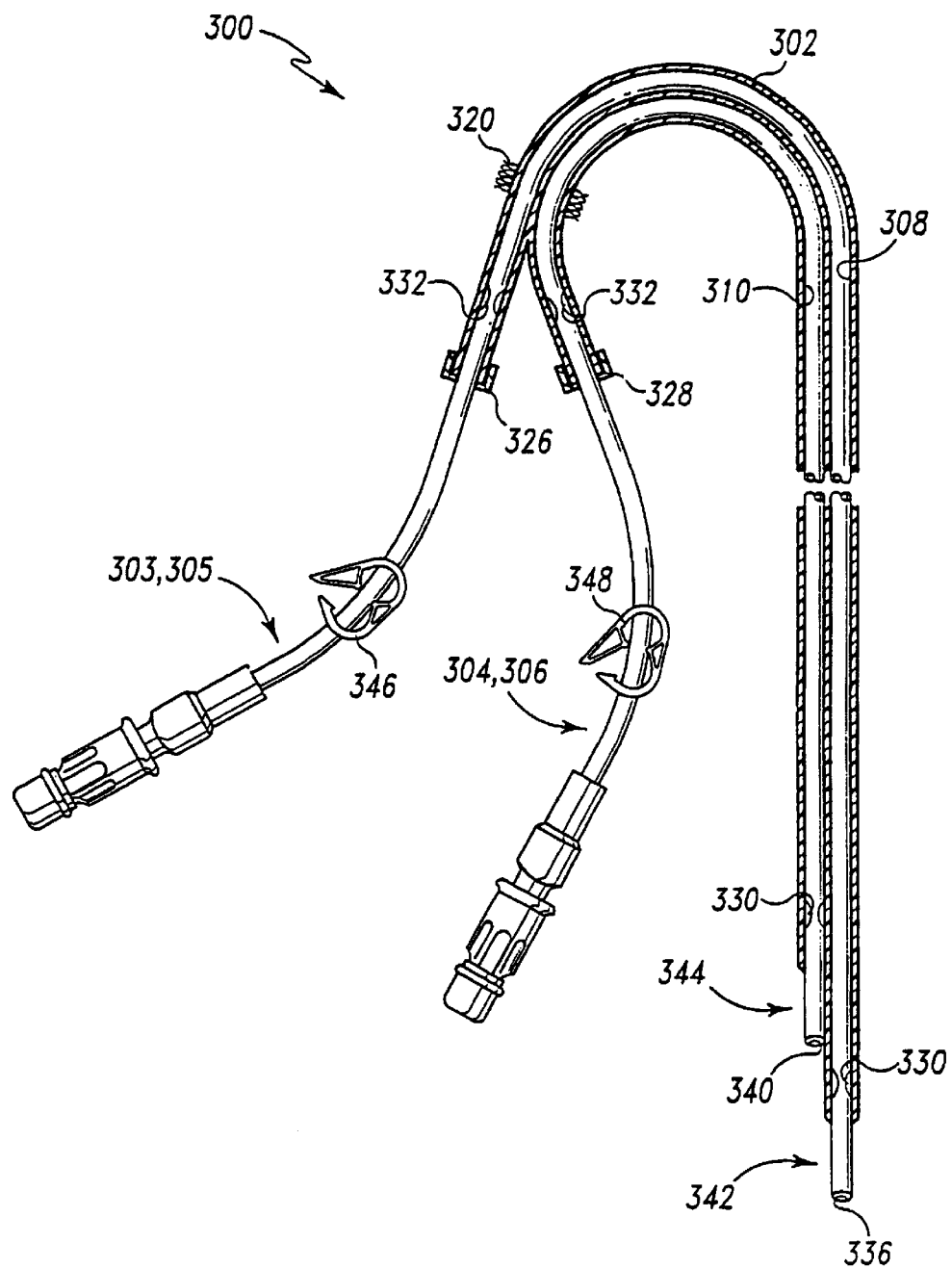
FIG. 15 is a view similar to FIG. 3, but showing yet another catheter system which incorporates the features of the present invention therein.

FIGS. 15–16 shows a catheter system 300 which also incorporates the features of the present invention therein. The catheter system 300 includes a guide catheter 302, a first original single lumen catheter 303, and a second original single lumen catheter 304. The catheter system 300 further includes a first replacement single lumen catheter 305, and a second replacement single lumen catheter 306 as will be discussed below.

The guide catheter 302 has a first guide lumen 308 and a second guide lumen 310 each which extends along the length of the guide catheter 302 as shown in FIG. 15. The first guide lumen 308 defines a first proximal guide orifice 312 and a first distal guide orifice 314, while the second guide lumen 310 defines a second proximal guide orifice 316 and a second distal guide orifice 318.

The first original catheter 303 is able to be positioned within the guide lumen 308 of the guide catheter 302, while the second original catheter 304 is able to be positioned within the guide lumen 310 of the guide catheter 302 as shown in FIG. 15. Similarly, the first replacement catheter 305 is also able to be positioned within the guide lumen 308 of the guide catheter 302, while the second replacement catheter 306 is also able to be positioned within the guide lumen 310 of the guide catheter 302 as shown in FIG. 15.

Note that the first original catheter 303 possesses the same physical construction and configuration as the first replacement catheter 305, and similarly the second original catheter 304 possesses the same physical construction and configuration as the second replacement catheter 306. Thus, for convenience of description, FIGS. 15 and 17 show reference numerals 303 and 305 identifying the same catheter. However, the first original catheter 303 will be located within the guide lumen 308 during a first period of time, while the first replacement catheter 305 will be located within the guide lumen 308 during a second period of time which is after the first period of time. Similarly, for convenience of description, FIGS. 15 and 18 show reference numerals 304 and 306 identifying the same catheter. However, the second original catheter 304 will be located within the guide lumen 310 during a first period of time, while the second replacement catheter 306 will be located within the guide lumen 310 during a second period of time which is after the first period of time.

In particular, according to one preferred manner of using the catheter system 300 during a medical procedure, such as a dialysis session, the first original catheter 303 and the second original catheter 304 are respectively positioned within the first guide lumen 308 and the second guide lumen 310 of the guide catheter 302 for a first period of time during which blood is infused and withdrawn therethrough. After the first period of time, the blood flow through the lumens of the first original catheter 303 and the second original catheter 304 may become partially or even totally inhibited due to blood clot build-up. In order to remedy this problem, the first original catheter 303 and the second original catheter 304 are respectively withdrawn from the first guide lumen 308 and the second guide lumen 310 of the guide catheter 302, and thereafter, the first replacement catheter 305 and the second replacement catheter 306 are respectively positioned within the first guide lumen 308 and the second guide lumen 310 of the guide catheter 302 for a subsequent second period of time during which blood is again infused and withdrawn therethrough.

Referring again to FIG. 15 as well as FIG. 16, the guide catheter 302 has a tissue ingrowth member 320 secured to an outer surface thereof. Tissue ingrowth member 320 is substantially identical to tissue ingrowth member 38 described hereinabove with regard to the catheter system 16.

As shown in FIG. 16, the guide catheter 302 includes (i) a first set of external threads 322 defined on an outer surface thereof near the first proximal guide orifice 312, and (ii) a second set of external threads 324 defined on an outer surface thereof near the second proximal guide orifice 316. The first set of external threads 322 cooperate with a first internally threaded cap 326 of the first original catheter 303 (and the first replacement catheter 305) to lock the first original catheter 303 (and the first replacement catheter 305) to the guide catheter 302 as shown in FIG. 15. Similarly, the second set of external threads 324 cooperate with a second internally threaded cap 328 of the second original catheter 304 (and the second replacement catheter 306) to lock the second original catheter 304 (and the second replacement catheter 306) to the guide catheter 302 as also shown in FIG. 15. The caps 326, 328 are substantially identical to the cap 67 which was described hereinabove with regard to catheter system 16. Moreover, each of the catheters 303, 304 (and 305, 306) are provided with an upper tab and a lower tab, similar to tabs 68, 69 of the catheter system 16 described above (see FIG. 6), to rotatably retain the caps 326, 328 in place.

While the original catheters 303, 304 and the replacement catheters 305, 306 are described as being locked to the guide catheter 302 using a locking arrangement which utilizes cooperating internal and external threads, and has substantial benefits thereby, numerous other arrangements may alternatively be incorporated into the dialysis system 300 to function to lock the original catheters 303, 304 and the replacement catheters 305, 306 to the guide catheter 302 and still achieve many of the advantages of the present invention. For example, the detent and groove type locking arrangement (not shown) or the leg and guide channel type locking arrangement (not shown) which were described above in regard to catheter system 16 may be utilized to lock the original catheters 303, 304 and the replacement catheters 305, 306 to the guide catheter 302.

The guide catheter 302 further includes a pair of distal blood flow valves 330 and a pair of proximal blood flow valves 332 positioned within the guide lumens 308, 310 as shown in FIGS. 15 and 16. The blood flow valves 330 and 332 are substantially identical to the blood flow valves 62 and 70 which were described hereinabove with regard to the catheter system 16.

Referring again to FIGS. 15, 17, and 18, the first original catheter 303 (and the first replacement catheter 305) includes a lumen 334. The lumen 334 defines a distal orifice 336. Similarly, the second original catheter 304 (and the second replacement catheter 306) includes a lumen 338. The lumen 338 defines a distal orifice 340. The distal orifice 336 is defined in a distal segment 342 of the first original catheter 303 (and the first replacement catheter 305). Similarly, the distal orifice 340 is defined in a distal segment 344 of the second original catheter 304 (and the second replacement catheter 306).

A clamp 346 is positioned on the first original catheter 303 (and the first replacement catheter 305), while another clamp 348 is positioned on the second original catheter 304 (and the second replacement catheter 306). The clamps 346, 348 are substantially identical in construction and function to the clamps 82, 84 discussed hereinabove with regard to the catheter system 16.

The first original catheter 303 (and the first replacement catheter 305) may be positioned within the first guide lumen 308 of the guide catheter 302, while the second original catheter 304 (and the second replacement catheter 306) may be positioned within the second guide lumen 310 of the guide catheter 302 as shown in FIG. 15. When the first original catheter 303 (or alternatively the first replacement catheter 305) is positioned within the first guide lumen 308 as shown in FIG. 15, the first original catheter 303 (or alternatively the first replacement catheter 305) is said to be positioned in an "inserted position." Similarly, when the second original catheter 304 (or alternatively the second replacement catheter 306) is positioned within the second guide lumen 310 as shown in FIG. 15, the second original catheter 304 (or alternatively the second replacement catheter 306) is also said to be positioned in an "inserted position." When the first original catheter 303 (or alternatively the first replacement catheter 305) is entirely removed from the first guide lumen 308, the first original catheter 303 (or alternatively the first replacement catheter 305) is said to be positioned in a "removed position." Similarly, when the second original catheter 304 (or alternatively the second replacement catheter 306) is entirely removed from the second guide lumen 310, the second original catheter 304 (or alternatively the second replacement catheter 306) is also said to be positioned in a "removed position."

When the first original catheter 303 (and the first replacement catheter 305) is positioned in the inserted position, the distal segment 342 of the first original catheter 303 (and the first replacement catheter 305) extends out of the distal guide orifice 314 of the guide catheter 302 as shown in FIG. 15. Similarly, when the second original catheter 304 (and the second replacement catheter 306) is positioned in the inserted position, the distal segment 344 of the second original catheter 304 (and the second replacement catheter 306) extends out of the distal guide orifice 318 of the guide catheter 302 as shown in FIG. 15. Accordingly, the distal orifices 336, 340 are each respectively positioned outside of the guide lumens 308, 310 when the first original catheter 303 (and the first replacement catheter 305) and the second original catheter 304 (and the second replacement catheter 306) are located in their inserted position.

Moreover, when the first original catheter 303 (and the first replacement catheter 305) is located in the inserted position, the threaded cap 326 is positioned adjacent to the first set of external threads 322 such that the threaded cap 326 can be rotated relative to the guide catheter 302 so as to lock the first original catheter 303 (and the first replacement catheter 305) to the guide catheter 302. Similarly, when the second original catheter 304 (and the second replacement catheter 306) is located in the inserted position, the threaded cap 328 is positioned adjacent to the second set of external threads 324 such that the threaded cap 328 can be rotated relative to the guide catheter 302 so as to lock the second original catheter 304 (and the second replacement catheter 306) to the guide catheter 302.

The guide catheter 302 is placed within the body 46 in substantially the same manner as was described hereinabove with respect to the placement of the guide catheter 32 of the catheter system 16 within the body 46 (i.e. by the tunneled catheter technique). Once the guide catheter 302 is placed in the body 46 as described above, the first original catheter 303 and the second original catheter 304 are respectively advanced through the guide lumens 308, 310 of the guide catheter 302 so that the distal orifices 336, 340 are respectively advanced out of the distal guide orifices 314, 318 and positioned within the superior vena cava 30 of the body 46. (In other words, the first original catheter 303 and the second original catheter 304 are respectively advanced to their inserted positions.) The first original catheter 303 and the second original catheter 304 are then respectively locked to the guide catheter 302 in the manner which has been previously described hereinabove.

Figure 19:
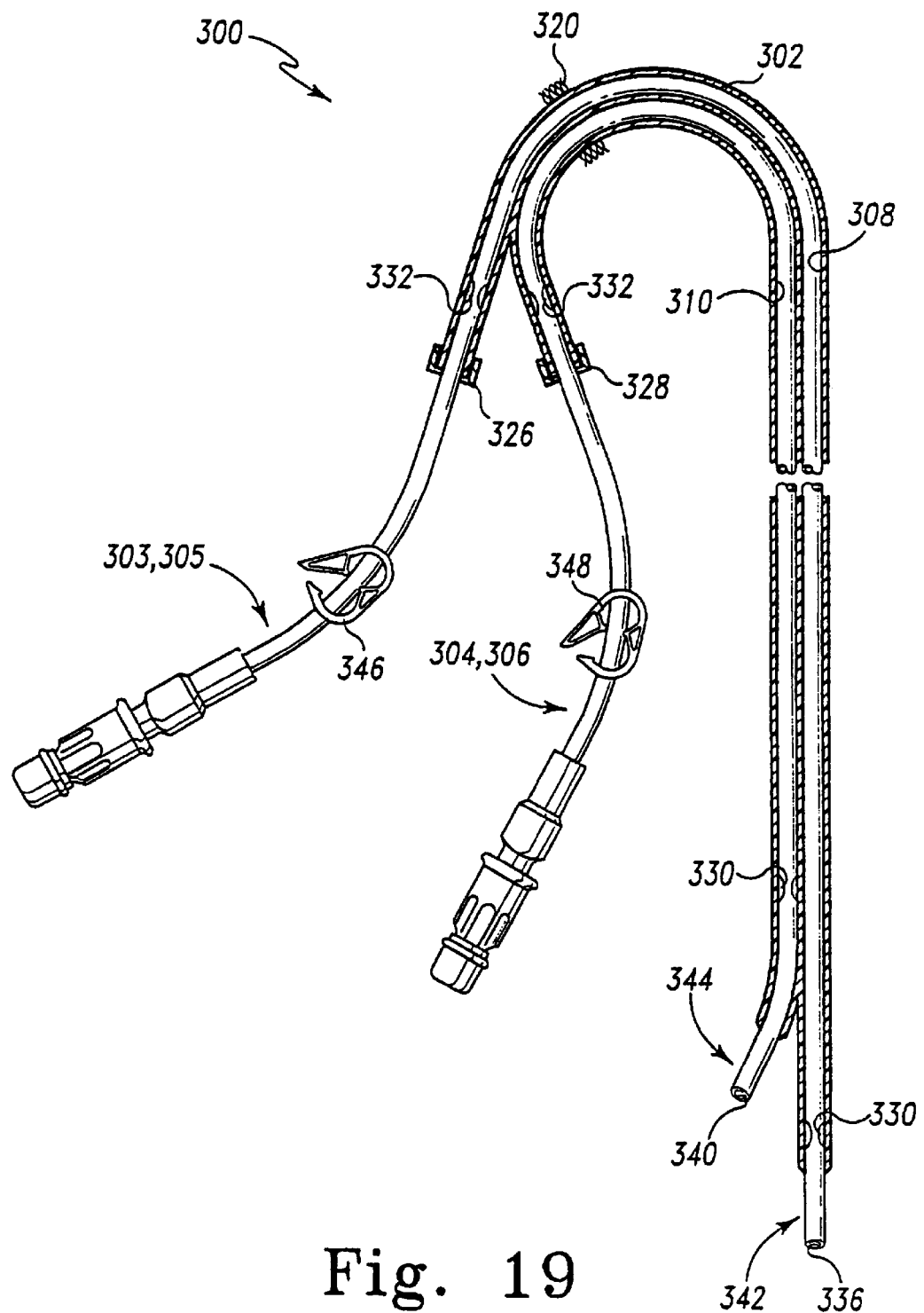
FIG. 19 is a view similar to FIG. 15, but showing another catheter system which incorporates the features of the present invention therein.

The catheter system 300 is shown in FIGS. 15 and 16 as having the distal segment of the guide lumen 310 located adjacent to the guide lumen 308. In the embodiment shown in FIGS. 15 and 16, the guide catheter 302 can be said to possess a side-by-side configuration. An alternative to providing the guide catheter 302 with a side-by-side configuration is shown in FIG. 19. In particular, a distal portion of the guide lumens 308, 310 of the catheter system 300 may be alternatively configured so that the distal portion of the guide catheter 302 is arranged in a bifurcated configuration as shown in FIG. 19. In such a configuration, the distal portion of the guide lumen 310 is arranged so as to gradually extend away from the distal portion of the guide lumen 308 as shown in FIG. 19. In the embodiment shown in FIG. 19, the guide catheter 302 can be said to possess a "split-tip" configuration.

III(a). First Manner of Using Catheter System 300

According to a first preferred manner of using the catheter system 300, the first original catheter 303 is replaced with the first replacement catheter 305 only after it becomes substantially inoperative due to partial or total occlusion of its lumen 334 due to, for example, blood clot build-up. Moreover, the second original catheter 304 is replaced with the second replacement catheter 306 only after it becomes substantially inoperative due to partial or total occlusion of its lumen 338 due to, for example, blood clot build-up. Such a manner of using the catheter system 300 would be substantially similar to the manner of using the catheter system 16 which was discussed herein in section 1(a) entitled "First Manner of Using Catheter System 16". However, it should be noted that it is possible, and may even be likely, that the first original catheter 303 (and the first replacement catheter 305) will be replaced due to blood clot build-up at a lower frequency in comparison to the replacement of the second original catheter 304 due to blood clot build-up. Such lower frequency of replacement may be attributable to the fact that during use of the catheter system 300, blood is advanced out of the first original catheter 303 (and the first replacement catheter 305) through the distal orifice 336. In contrast, during use of the catheter system 300, blood is advanced into the second original catheter 304 (and the second replacement catheter 306) through the distal orifice 340. Historically, occlusion problems occur more frequently during a dialysis procedure when attempting to withdraw blood from a patient's vascular system through a dialysis catheter in comparison to attempting to infuse blood back into a patient's vascular system through the dialysis catheter.

III(b). Second Manner of Using Catheter System 300

In accordance with a second preferred manner of using the catheter system 300, each of the first original catheter 303 and the second original catheter 304 is a "single use" catheter. In other words, both the first original catheter 303 and the second original catheter 304 of catheter system 300 are only used for a single dialysis session, and thereafter discarded. Hence, both the first original catheter 303 and the second original catheter 304 would typically never be left in the vascular system 22 long enough to become substantially inoperative due to partial or total occlusion of its respective lumens 334, 338 as a result of, for example, blood clot build-up. Such a manner of using the catheter system 300 would be substantially similar to the manner of using the catheter system 16 which was discussed herein in section 1(b) entitled "Second Manner of Using Catheter System 16".

Note that between dialysis sessions, when the first original catheter 303 (or the first replacement catheter 305) is not located within the guide lumen 308 of the guide catheter 302, a first closure member 350, such as a cap, is secured to the guide catheter 302 so as to cover the first proximal guide orifice 312. Optionally, a clamp (not shown) which is similar in construction and function to the clamp 101 of the catheter system 16 (see FIG. 11) may also be positioned on the branch of the guide catheter 302 near the first proximal guide orifice 312 between dialysis sessions. Also note that between dialysis sessions, when the second original catheter 304 (or the second replacement catheter 306) is not located within the guide lumen 310 of the guide catheter 302, a second closure member 352, such as another cap, is secured to the guide catheter 302 so as to cover the second proximal guide orifice 316. Optionally, another clamp (not shown) which is similar in construction and function to the clamp 101 of the catheter system 16 (see FIG. 11) may also be positioned on the branch of the guide catheter 302 near the second proximal guide orifice 316 between dialysis sessions. The closure members 350, 352 are substantially identical in construction and function to the closure member 100 of the catheter system 16 shown in FIGS. 11–13.

When the patient desires to be dialyzed again, the guide catheter 302 is prepped in a sterile manner such as by applying an anti-bacterial solution thereto. Thereafter, the closure members 350, 352 would be unlocked from the guide catheter 302, and thereafter the replacement catheters 305, 306 would be respectively inserted into the guide lumens 308, 310 and then locked to the guide catheter 302 as hereinabove described. Again, this manner of using the catheter system 300 would be substantially similar to the manner of using the catheter system 16 which was discussed herein in section 1(b) entitled "Second Manner of Using Catheter System 16".

Also, please note that according to the second manner of using the catheter system 300, the original catheters 303, 304 and the replacement catheters 305, 306 are only "single use" catheters. Accordingly, the physical structure of the original catheters 303, 304, 305, 306 of the catheter system 300 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

III(c). Third Manner of Using Catheter System 300

According to a third preferred manner of using the catheter system 300, the first original catheter 303 is replaced with the first replacement catheter 305 after any predetermined number of dialysis sessions is performed. Moreover, the second original catheter 304 is replaced with the second replacement catheter 306 after any predetermined number of dialysis sessions is performed. For example, such predetermined number may be (i) determined from experimental studies, (ii) determined based on patient history, or (iii) determined based on other criteria. Such a manner of using the catheter system 300 would be substantially similar to the manner of using the catheter system 16 which was discussed herein in section 1(c) entitled "Third Manner of Using Catheter System 16". In addition, the predetermined number of dialysis sessions after which the first original catheter 303 is replaced does not necessarily have to be equal to the predetermined number of dialysis sessions after which the second original catheter 304 is replaced. For example, the first original catheter 303 may be replaced with a first replacement catheter 305 after every four dialysis sessions, while the second original catheter 304 may be replaced with a second replacement catheter 306 after every three dialysis sessions.

IV. Catheter System 400

Figure 20:
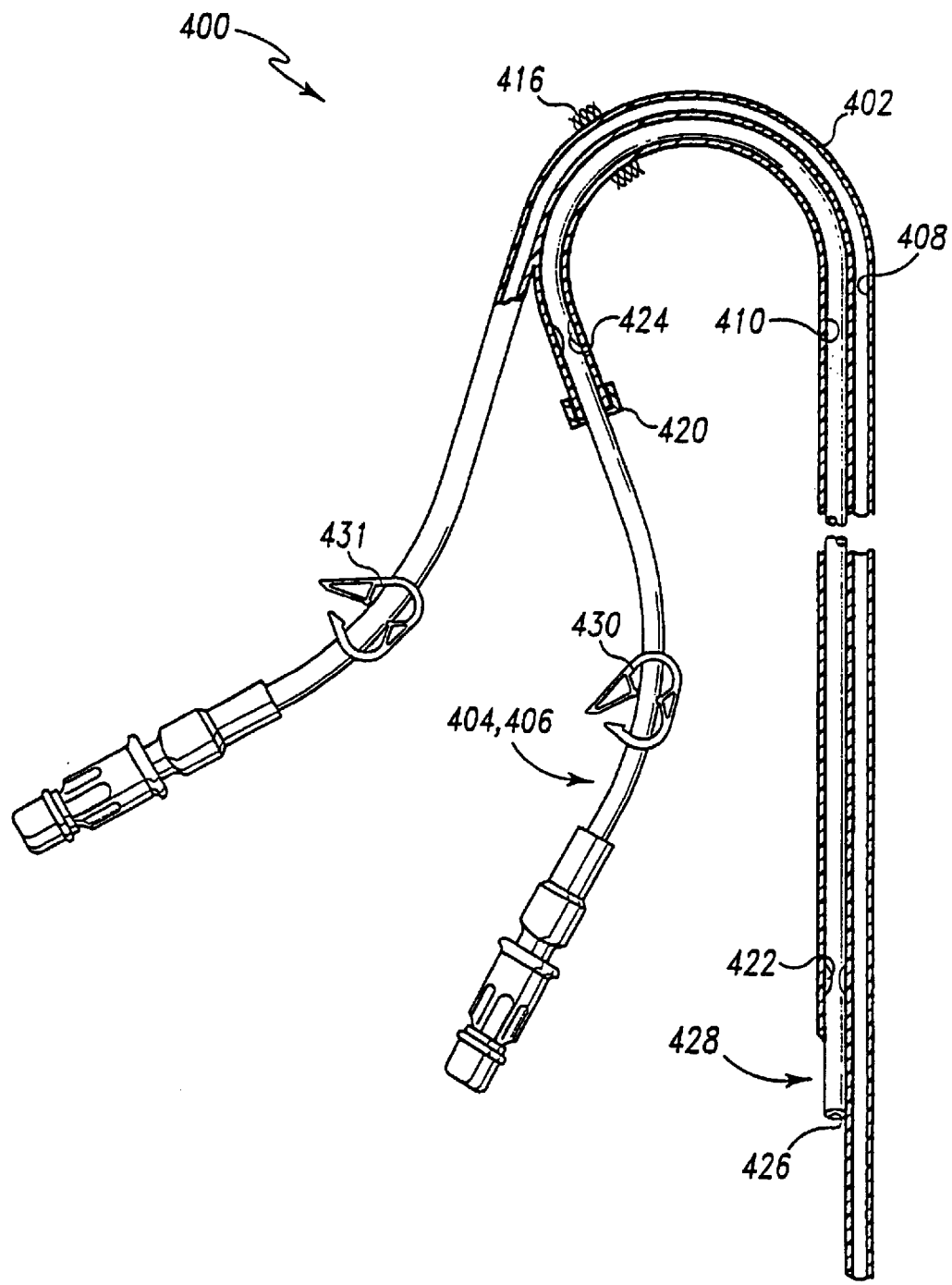
FIG. 20 is a view similar to FIG. 3, but showing another catheter system which incorporates the features of the present invention therein.

FIG. 20 shows a catheter system 400 which incorporates the features of the present invention therein. The catheter system 400 includes a guide catheter 402 and an original single lumen catheter 404. The original catheter 404 defines a lumen 405 through which blood may be advanced. The catheter system 400 further includes a replacement single lumen catheter 406 as will be discussed below. The guide catheter 402 has an active lumen 408 and a guide lumen 410 each which extends along the length of the guide catheter 402 as shown in FIG. 20. The guide lumen 410 defines a proximal guide orifice 412 and a distal guide orifice 414.

The original catheter 404 is able to be positioned within the guide lumen 410 of the guide catheter 402. Similarly, the replacement catheter 406 is also able to be positioned within the guide lumen 410 of the guide catheter 402. Note that the original catheter 404 possesses the same physical construction and configuration as the replacement catheter 406. Thus, for convenience of description, FIGS. 20–22 show reference numerals 404 and 406 identifying the same catheter. However, the original catheter 404 will be located within the guide lumen 410 during a first period of time, while the replacement catheter 406 will be located within the guide lumen 410 during a second period of time which is after the first period of time.

In particular, according to one preferred manner of using the catheter system 400 during a medical procedure, such as a dialysis session, the original catheter 404 is positioned within the guide lumen 410 for a first period of time during which blood is withdrawn from the vascular system 22 through its lumen 405. Also during the first period of time, blood is infused into the vascular system 22 through the active lumen 408 of the guide catheter 402. After the first period of time, the blood flow through the lumen 405 of the original catheter 404 may become partially or even totally inhibited due to, for example, blood clot build-up. In order to remedy this problem, the original catheter 404 is withdrawn from the guide lumen 410, and thereafter, the replacement catheter 406 is positioned within the guide lumen 410 of the guide catheter 402 for a subsequent second period of time during which blood is withdrawn from the vascular system 22 through the lumen 405 of the replacement catheter 406. Also during the second period of time, blood is infused into the vascular system 22 through the active lumen 408 of the guide catheter 402.

Referring again to FIGS. 20–21, the guide catheter 402 has a tissue ingrowth member 416 secured to an outer surface thereof. Tissue ingrowth member 416 is substantially identical to tissue ingrowth member 38 described hereinabove with regard to the catheter system 16.

As shown in FIGS. 20–21, the guide catheter 402 includes a set of external threads 418 defined on an outer surface thereof near the proximal guide orifice 412. The set of external threads 418 cooperates with an internally threaded cap 420 of the original catheter 404 (and the replacement catheter 406) to lock the original catheter 404 (and the replacement catheter 406) to the guide catheter 402 as shown in FIG. 20. The cap 420 is substantially identical to the cap 67 which was described hereinabove with regard to catheter system 16. Moreover, each of the catheters 404 and 406 is provided with an upper tab and a lower tab, similar to tabs 68, 69 of the catheter system 16 described above (see FIG. 6), to rotatably retain the cap 420 in place.

While the original catheter 404 and the replacement catheter 406 is described as being locked to the guide catheter 402 using a locking arrangement which utilizes cooperating internal and external threads, and has substantial benefits thereby, numerous other arrangements may alternatively be incorporated into the dialysis system 400 to function to lock the original catheter 404 and the replacement catheter 406 to the guide catheter 402 and still achieve many of the advantages of the present invention. For example, the detent and groove type locking arrangement (not shown) or the leg and guide channel type locking arrangement (not shown) which were described above in regard to catheter system 16 may be utilized to lock the original catheter 404 and the replacement catheter 406 to the guide catheter 402.

The guide catheter 402 further includes a distal blood flow valve 422 and a proximal blood flow valve 424 positioned within the guide lumen 410 as shown in FIGS. 20 and 21. The blood flow valves 422 and 424 are substantially identical to the blood flow valves 62 and 70 which were described hereinabove with regard to the catheter system 16. The guide catheter 402 may further include an additional distal blood flow valve (not shown) located in the distal portion of the active lumen 408 and an additional proximal blood flow valve (not shown) located in the proximal portion of the active lumen 408. These additional blood flow valves would also be substantially identical to the blood flow valves 62 and 70 which were described hereinabove with regard to the catheter system 16.

Referring again to FIGS. 20–21 and also to FIG. 22, the original catheter 404 (and the replacement catheter 406) defines the lumen 405 through which blood is advanced. The lumen 405 defines a distal orifice 426. The distal orifice 426 is defined in a distal segment 428 of the original catheter 404 (and the replacement catheter 406).

A clamp 430 is positioned on the original catheter 404 (and the replacement catheter 406). Another clamp 431 is positioned on the guide catheter 402 as shown in FIGS. 20 and 21. The clamps 430, 431 are substantially identical in construction and function to the clamps 82, 84 discussed hereinabove with regard to the catheter system 16.

The original catheter 404 (and the replacement catheter 406) may be positioned within the guide lumen 410 of the guide catheter 402 as shown in FIG. 20. When the original catheter 404 (or alternatively the replacement catheter 406) is positioned within the guide lumen 410 as shown in FIG. 20, the original catheter 404 (or alternatively the replacement catheter 406) is said to be positioned in an "inserted position." When the original catheter 404 (or alternatively the replacement catheter 406) is entirely removed from the guide lumen 410, the original catheter 404 (or alternatively the replacement catheter 406) is said to be positioned in a "removed position."

When the original catheter 404 (and the replacement catheter 406) is positioned in the inserted position, the distal segment 428 of the original catheter 404 (and the replacement catheter 406) extends out of the distal guide orifice 414 of the guide catheter 402 as shown in FIG. 20. Accordingly, the distal orifice 426 is positioned outside of the guide lumen 410 when the original catheter 404 (and the replacement catheter 406) is located in its inserted position.

Moreover, when the original catheter 404 (and the replacement catheter 406) is located in the inserted position, the threaded cap 420 is positioned adjacent to the set of external threads 418 such that the threaded cap 420 can be rotated relative to guide catheter 402 so as to lock the original catheter 404 (and the replacement catheter 406) to the guide catheter 402.

The guide catheter 402 is placed within the body 46 in substantially the same manner as was described hereinabove with respect to the placement of the guide catheter 32 of the catheter system 16 within the body 46 (i.e. by the tunneled catheter technique). Once the guide catheter 402 is placed in the body 46 as described above, the original catheter 404 is advanced through the guide lumen 410 of the guide catheter 402 so that the distal orifice 426 is advanced out of the distal guide orifice 414 and positioned within the superior vena cava 30 of the body 46. (In other words, the original catheter 404 is advanced to its inserted position.) The original catheter 404 is then respectively locked to the guide catheter 402 in the manner which has been previously described hereinabove.

Figure 23:
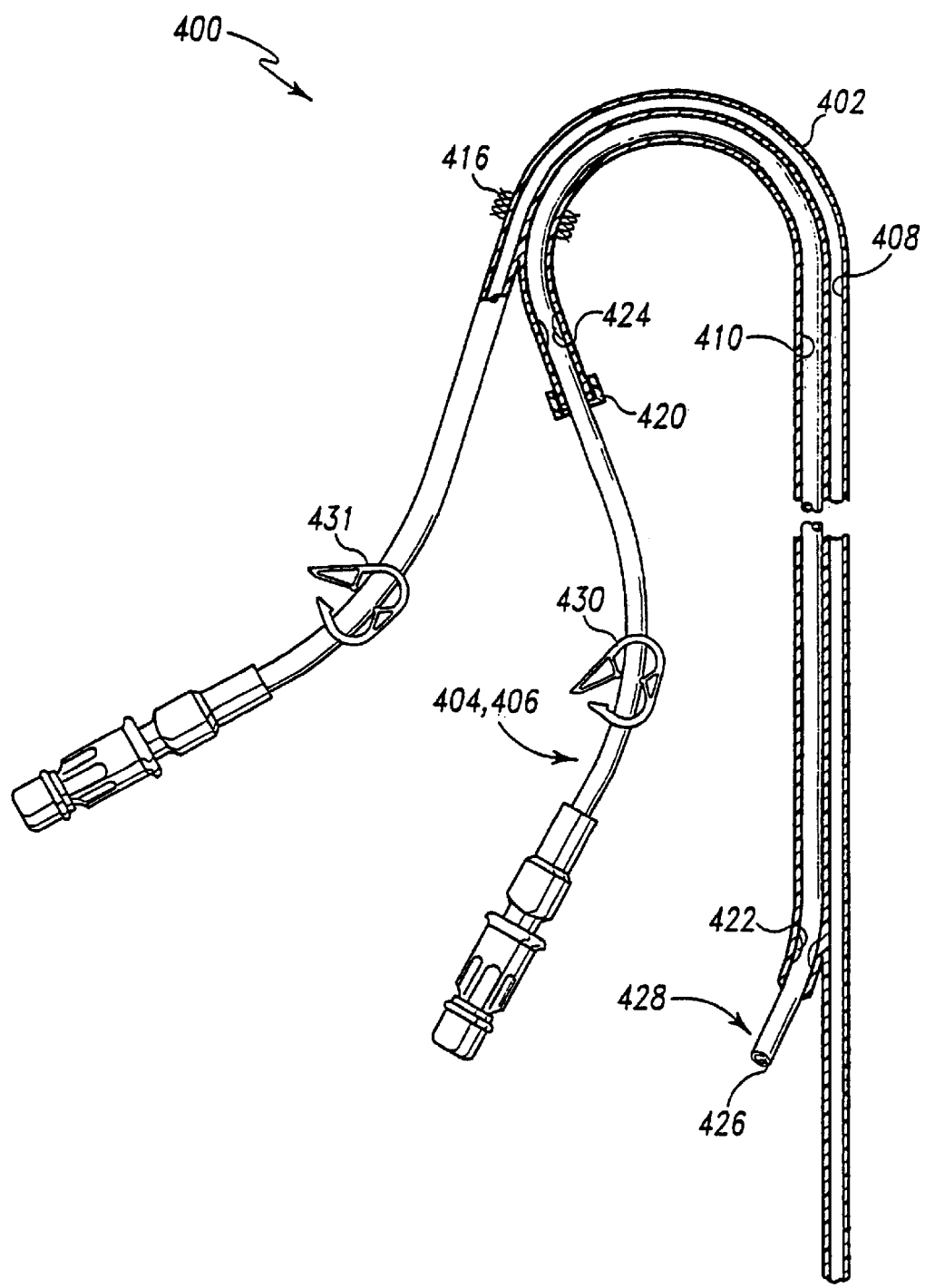
FIG. 23 is a view similar to FIG. 20, but showing another catheter system which incorporates the features of the present invention therein.

The catheter system 400 is shown in FIGS. 20 and 21 as having the distal segment of the guide lumen 410 located adjacent to the active lumen 408. In the embodiment shown in FIGS. 20 and 21, the guide catheter 402 can be said to possess a side-by-side configuration. An alternative to providing the guide catheter 402 with a side-by-side configuration is shown in FIG. 23. In particular, a distal portion of both the guide lumen 410 and the active lumen 408 of the catheter system 400 may be alternatively configured so that the distal portion of the guide catheter 402 is arranged in a bifurcated configuration as shown in FIG. 23. In such a configuration, the distal portion of the guide lumen 410 is arranged so as to gradually extend away from the distal portion of the active lumen 408 as shown in FIG. 23. In the embodiment shown in FIG. 23, the guide catheter 402 can be said to possess a "split-tip" configuration.

Figure 24:
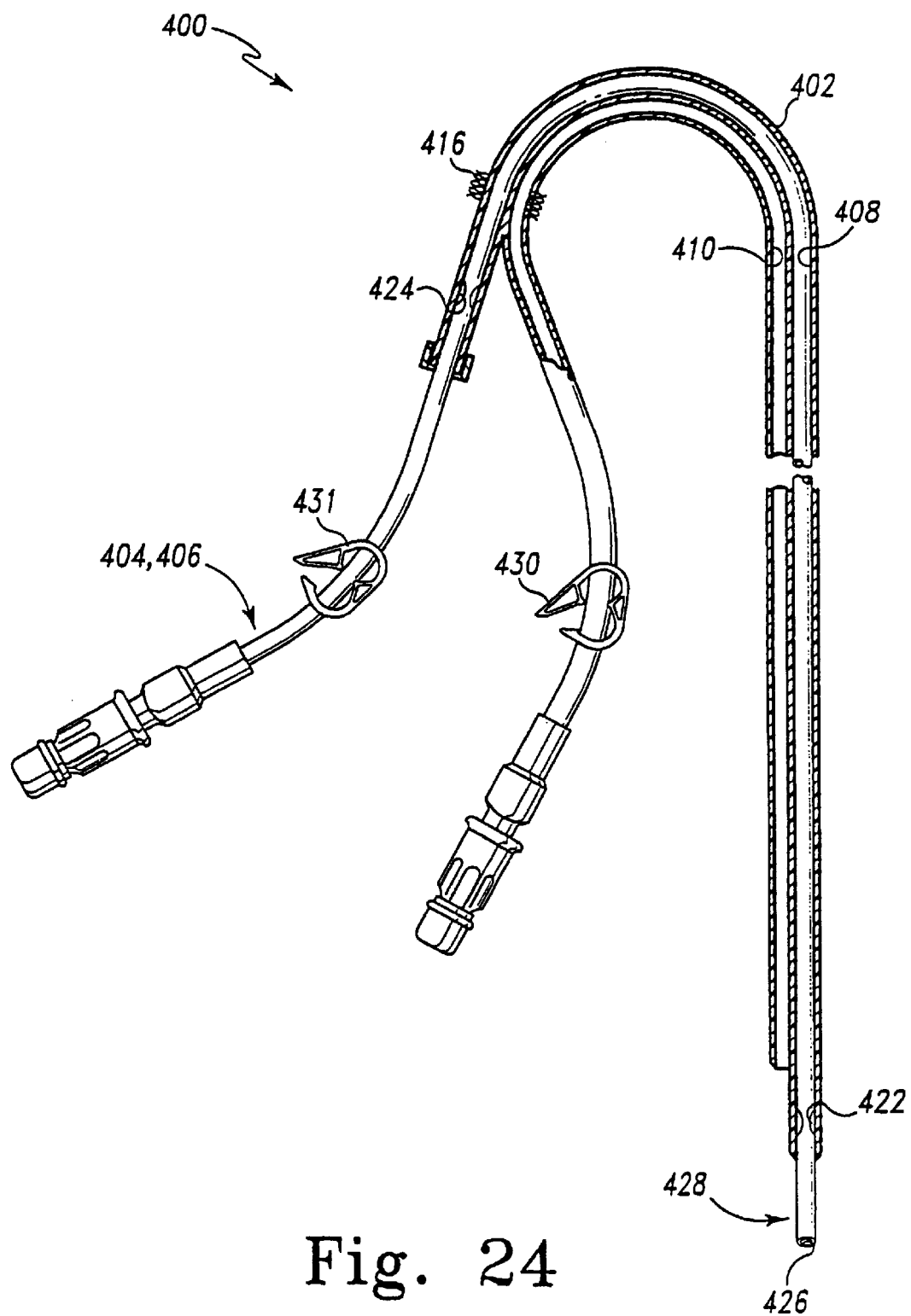
FIG. 24 is a view similar to FIG. 20, but showing still another catheter system which incorporates the features of the present invention therein.

In addition, the catheter system 400 is shown in FIGS. 20 and 21 as having the original catheter 404 (and the replacement catheter 406) positionable within the guide lumen 410 of the guide catheter 402 while the active lumen 408 does not receive any such catheter therein. In an alternative embodiment of the present invention which is shown in FIG. 24, the catheter system 400 may be modified such that the original catheter 404 (and the replacement catheter 406) would be positionable within the lumen 408 of the guide catheter 402 while the lumen 410 would not receive any such catheter therein. In such an embodiment, the lumen 410 would function to advance a fluid therethrough, such as blood.

IV(a). First Manner of Using Catheter System 400

According to a first preferred manner of using the catheter system 400, the original catheter 404 is replaced with the replacement catheter 406 only after it becomes substantially inoperative due to partial or total occlusion of its lumen 405 as a result of, for example, blood clot build-up. Such a manner of using the catheter system 400 would be substantially similar to the manner of using the catheter system 16 which was discussed herein in section 1(a) entitled "First Manner of Using Catheter System 16".

IV(b). Second Manner of Using Catheter System 400

In accordance with a second preferred manner of using the catheter system 400, the original catheter 404 is a "single use" catheter. In other words, the original catheter 404 of catheter system 400 is only used for a single dialysis session, and thereafter discarded. Hence, the original catheter 404 would typically never be left in the vascular system 22 long enough to become substantially inoperative due to partial or total occlusion of its lumen 405 as a result of, for example, blood clot build-up. Such a manner of using the catheter system 400 would be substantially similar to the manner of using the catheter system 16 which was discussed herein in section 1(b) entitled "Second Manner of Using Catheter System 16".

Note that between dialysis sessions, when the original catheter 404 (or the replacement catheter 406) is not located within the guide lumen 410 of the guide catheter 402, a closure member 432, such as a cap, is secured to the guide catheter 402 so as to cover the proximal guide orifice 412. The closure member 432 is substantially identical in construction and function to the closure member 100 of the catheter system 16 shown in FIGS. 11–13. Optionally, a clamp (not shown) which is similar in construction and function to the clamp 101 of the catheter system 16 (see FIG. 11) may also be positioned on the branch of the guide catheter 402 near the proximal guide orifice 412 between dialysis sessions.

Of course, when the patient desires to be dialyzed again, the guide catheter 402 is prepped in a sterile manner such as by applying an anti-bacterial solution thereto. Thereafter, the closure member 432 would be unlocked from the guide catheter 402, and thereafter the replacement catheter 406 would be inserted into the guide lumen 410 and then locked to the guide catheter 402 as hereinabove described. Again, this manner of using the catheter system 400 would be substantially similar to the manner of using the catheter system 16 which was discussed herein in section 1(b) entitled "Second Manner of Using Catheter System 16".

Also, please note that according to the second manner of using the catheter system 400, the original catheter 404 and the replacement catheter 406 are only a "single use" catheter. Accordingly, the physical structure of the catheters 404, 406 of the catheter system 400 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

IV(c). Third Manner of Using Catheter System 400

According to a third preferred manner of using the catheter system 400, the original catheter 404 is replaced with the replacement catheter 406 after any predetermined number of dialysis sessions is performed. For example, such predetermined number may be (i) determined from experimental studies, (ii) determined based on patient history, or (iii) determined based on other criteria. Such a manner of using the catheter system 400 would be substantially similar to the manner of using the catheter system 16 which was discussed herein in section 1(c) entitled "Third Manner of Using Catheter System 16".

V. Catheter System 500

Figure 25:
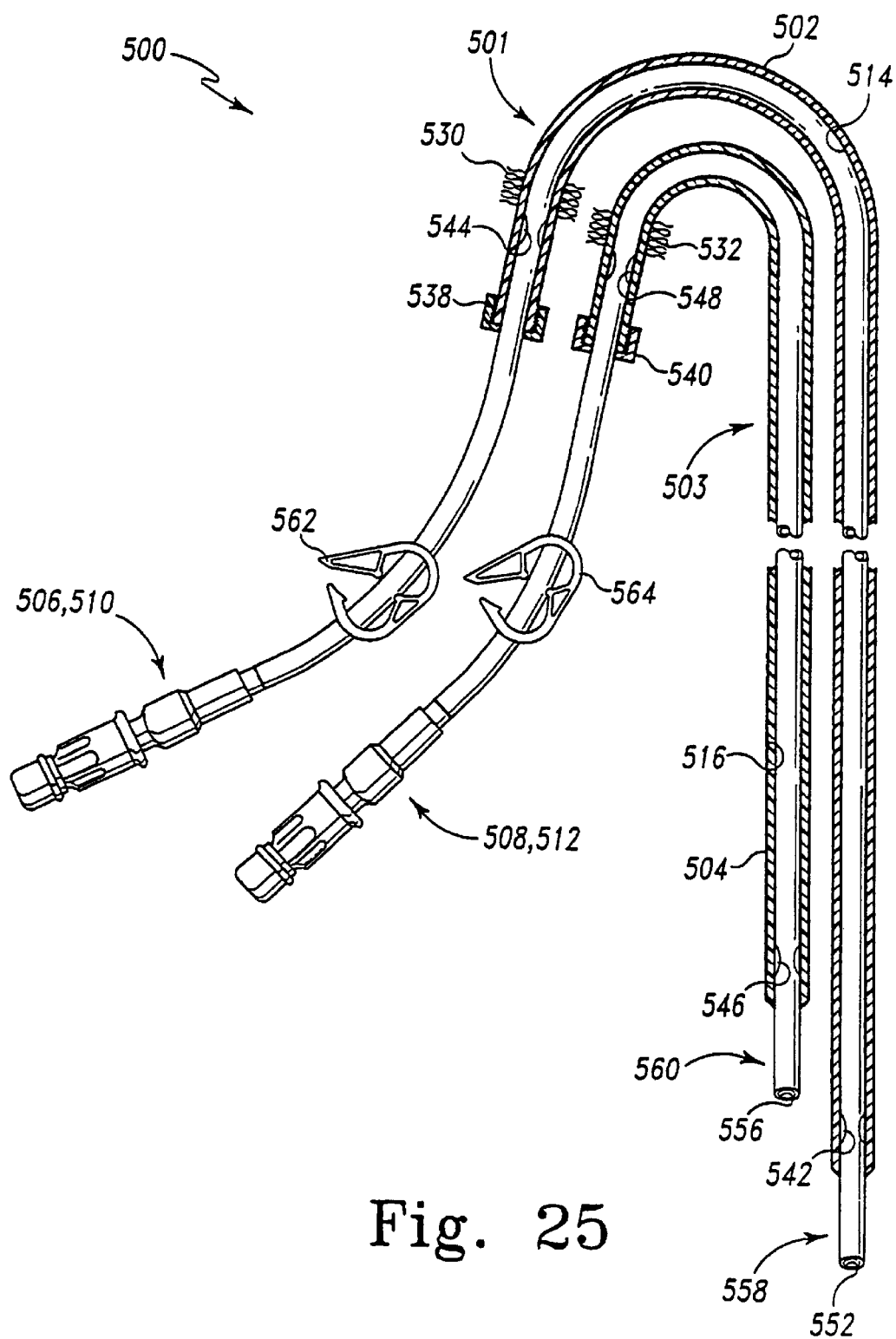
FIG. 25 is a view similar to FIG. 3, but showing yet another catheter system which incorporates the features of the present invention therein.

FIG. 25 shows a catheter system 500 which further incorporates the features of the present invention therein. The catheter system 500 includes a first catheter apparatus 501 and a second catheter apparatus 503. The first catheter apparatus 501 includes a first guide catheter 502 and a first original single lumen catheter 506, while the second catheter apparatus 503 includes a second guide catheter 504 and a second original single lumen catheter 508. The first catheter apparatus 501 further includes a first replacement single lumen catheter 510 as will be discussed below, and the second catheter apparatus further includes a second replacement single lumen catheter 512 as also will be described below.

Figure 26:
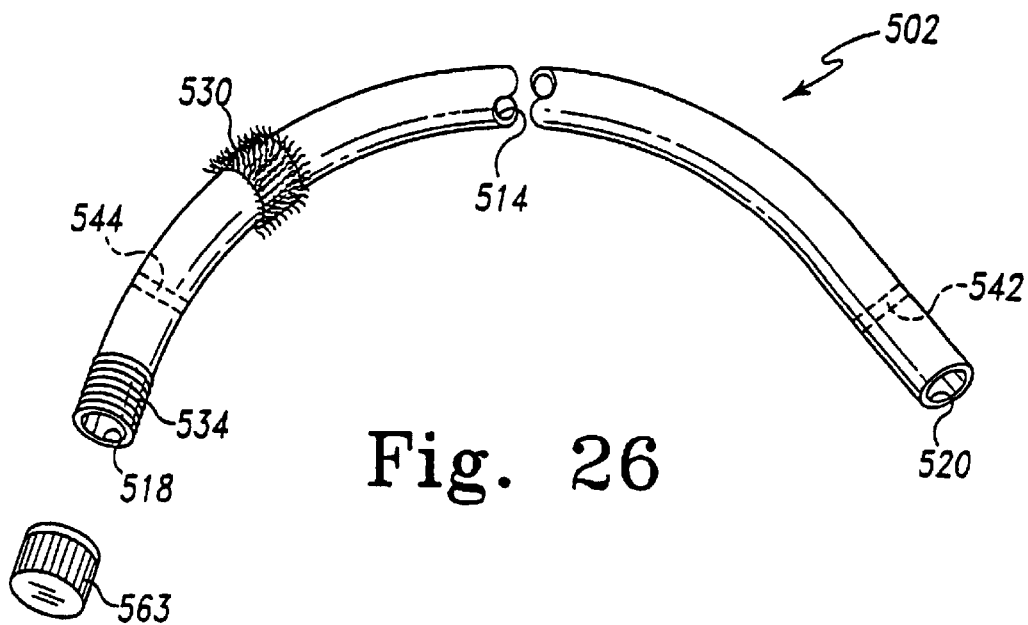
FIG. 26 is a side elevational view of the first guide catheter of the catheter system shown in FIG. 25.
Figure 27:
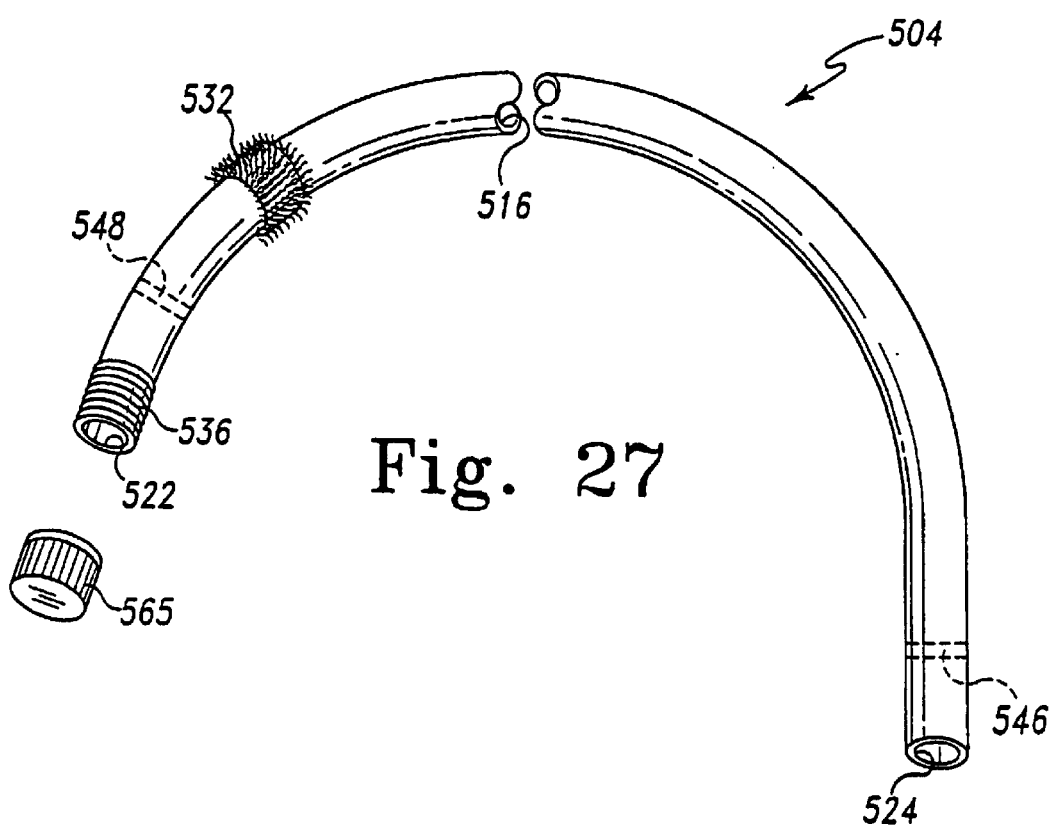
FIG. 27 is a side elevational view of the second guide catheter of the catheter system shown in FIG. 25.

The first guide catheter 502 has a first guide lumen 514 defined therein which extends along the length of the guide catheter 502 as shown in FIGS. 25 and 26. The second guide catheter 504 has a second guide lumen 516 defined therein which extends along the length of the guide catheter 504 as also shown in FIGS. 25 and 27. The first guide lumen 514 defines a first proximal guide orifice 518 and a first distal guide orifice 520, while the second guide lumen 516 defines a second proximal guide orifice 522 and a second distal guide orifice 524.

The first original catheter 506 is able to be positioned within the guide lumen 514 of the guide catheter 502, while the second original catheter 508 is able to be positioned within the guide lumen 516 of the guide catheter 504 as shown in FIG. 25. Similarly, the first replacement catheter 510 is also able to be positioned within the guide lumen 514 of the guide catheter 502, while the second replacement catheter 512 is also able to be positioned within the guide lumen 516 of the guide catheter 504 as shown in FIG. 25.

Figure 28:
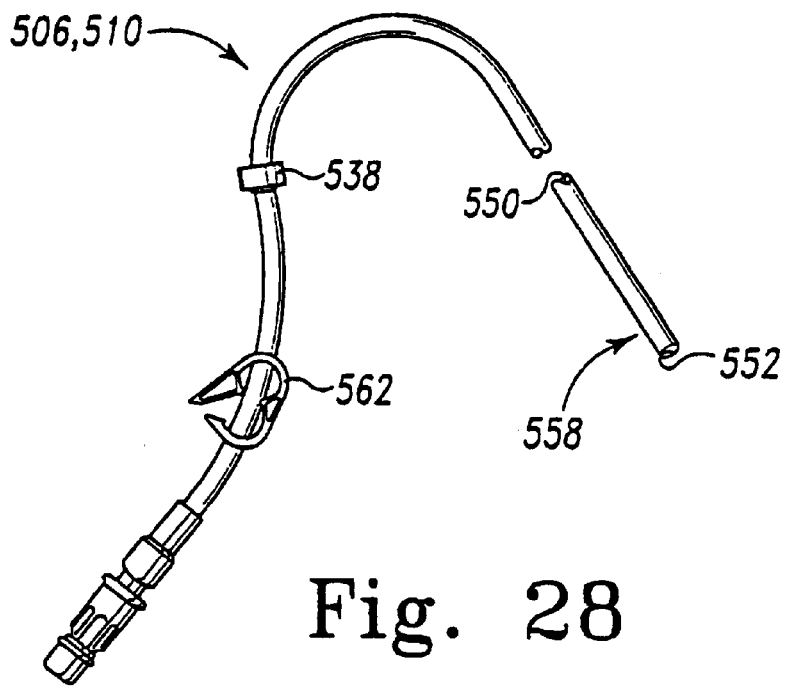
FIG. 28 is a side elevational view of the first original catheter of the catheter system shown in FIG. 25.
Figure 29:
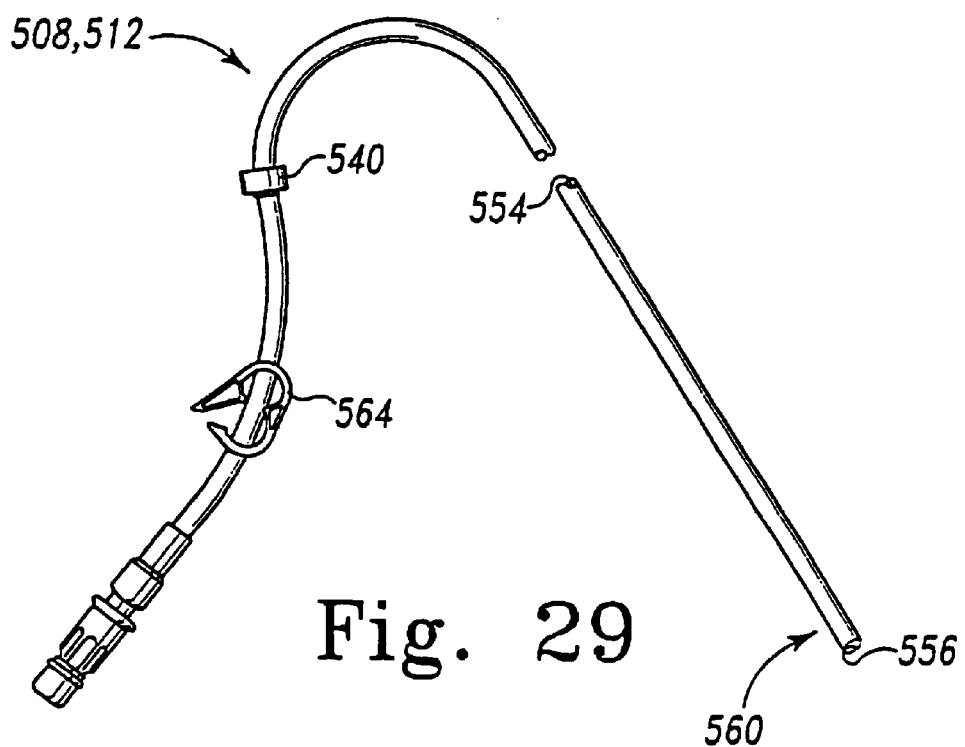
FIG. 29 is a side elevational view of the second original catheter of the catheter system shown in FIG. 25.

Note that the first original catheter 506 possesses the same physical construction and configuration as the first replacement catheter 510, and similarly the second original catheter 508 possesses the same physical construction and configuration as the second replacement catheter 512. Thus, for convenience of description, FIGS. 25, 28, and 29 show (i) reference numerals 506 and 510 identifying the same catheter, and (ii) reference numerals 508 and 512 identifying the same catheter. However, the first original catheter 506 will be located within the first guide lumen 514 during a first period of time, while the first replacement catheter 510 will be located within the first guide lumen 514 during a second period of time which is after the first period of time. Similarly, the second original catheter 508 will be located within the second guide lumen 516 during a first period of time, while the second replacement catheter 512 will be located within the second guide lumen 516 during a second period of time which is after the first period of time.

In particular, according to one preferred manner of using the catheter system 500 during a medical procedure, such as a dialysis session, the first original catheter 506 and the second original catheter 508 are respectively positioned within the first guide lumen 514 of the guide catheter 502 and the second guide lumen 516 of the guide catheter 504 for a first period of time during which blood is infused and withdrawn therethrough. After the first period of time, the blood flow through the lumens of the first original catheter 506 and the second original catheter 508 may become partially or even totally inhibited due to, for example, blood clot build-up. In order to remedy this problem, the first original catheter 506 and the second original catheter 508 are respectively withdrawn from the first guide lumen 514 and the second guide lumen 516, and thereafter, the first replacement catheter 510 and the second replacement catheter 512 are respectively positioned within the first guide lumen 514 and the second guide lumen 516 for a subsequent second period of time during which blood is again infused and withdrawn therethrough.

Referring again to FIGS. 25, 26, 27 and 30, the first guide catheter 502 has a tissue ingrowth member 530 secured to an outer surface thereof, while the second guide catheter 504 has a tissue ingrowth member 532 secured to an outer surface thereof. Tissue ingrowth members 530, 532 are substantially identical to tissue ingrowth member 38 described hereinabove with regard to the catheter system 16.

As shown in FIGS. 26 and 27, the first guide catheter 502 includes a first set of external threads 534 defined on an outer surface thereof near the first proximal guide orifice 518, while the second guide catheter 504 includes a second set of external threads 536 defined on an outer surface thereof near the second proximal guide orifice 522. The first set of external threads 534 cooperate with a first internally threaded cap 538 of the first original catheter 506 (and the first replacement catheter 510) to lock the first original catheter 506 (and the first replacement catheter 510) to the first guide catheter 502 as shown in FIG. 25. Similarly, the second set of external threads 536 cooperate with a second internally threaded cap 540 of the second original catheter 508 (and the second replacement catheter 512) to lock the second original catheter 508 (and the second replacement catheter 512) to the second guide catheter 504 as also shown in FIG. 25. The caps 538, 540 are substantially identical to the cap 67 which was described hereinabove with regard to catheter system 16. Moreover, each of the catheters 506, 508 (and 510, 512) are provided with an upper tab and a lower tab, similar to tabs 68, 69 of the catheter system 16 described above (see FIG. 6), to rotatably retain the caps 538, 540 in place.

While the original catheters 506, 508 and the replacement catheters 510, 512 are described as being respectively locked to the guide catheters 502, 504 using a locking arrangement which utilizes cooperating internal and external threads, and has substantial benefits thereby, numerous other arrangements may alternatively be incorporated into the dialysis system 500 to function to lock the original catheters 506, 508 and the replacement catheters 510, 512 to the guide catheters 502, 504 and still achieve many of the advantages of the present invention. For example, the detent and groove type locking arrangement (not shown) or the leg and guide channel type locking arrangement (not shown) which were described above in regard to catheter system 16 may be utilized to respectively lock the original catheters 506, 508 and the replacement catheters 510, 512 to the guide catheters 502, 504.

The first guide catheter 502 further includes a distal blood flow valve 542 and a proximal blood flow valve 544 positioned within the first guide lumen 514 as shown in FIGS. 25 and 26. The second guide catheter 504 further includes a distal blood flow valve 546 and a proximal blood flow valve 548 positioned within the second guide lumen 516 as also shown in FIGS. 25 and 26. The blood flow valves 542, 544, 546, and 548 are substantially identical to the blood flow valves 62 and 70 which were described hereinabove with regard to the catheter system 16.

Referring again to FIGS. 25, 28, 29, and 30, the first original catheter 506 (and the first replacement catheter 510) includes a lumen 550. The lumen 550 defines a distal orifice 552. Similarly, the second original catheter 508 (and the second replacement catheter 512) includes a lumen 554. The lumen 554 defines a distal orifice 556. The distal orifice 552 is defined in a distal segment 558 of the first original catheter 506 (and the first replacement catheter 510). Similarly, the distal orifice 556 is defined in a distal segment 560 of the second original catheter 508 (and the second replacement catheter 512).

A clamp 562 is positioned on the first original catheter 506 (and the first replacement catheter 510), while another clamp 564 is positioned on the second original catheter 508 (and the second replacement catheter 512). The clamps 562, 564 are substantially identical in construction and function to the clamps 82, 84 discussed hereinabove with regard to the catheter system 16.

The first original catheter 506 (and the first replacement catheter 510) may be positioned within the first guide lumen 514 of the guide catheter 502, while the second original catheter 508 (and the second replacement catheter 512) may be positioned within the second guide lumen 516 of the second guide catheter 504 as shown in FIG. 25. When the first original catheter 506 (or alternatively the first replacement catheter 510) is positioned within the first guide lumen 514 as shown in FIG. 25, the first original catheter 506 (or alternatively the first replacement catheter 510) is said to be positioned in an "inserted position." Similarly, when the second original catheter 508 (or alternatively the second replacement catheter 512) is positioned within the second guide lumen 516 as shown in FIG. 25, the second original catheter 508 (or alternatively the second replacement catheter 512) is also said to be positioned in an "inserted position." When the first original catheter 506 (or alternatively the first replacement catheter 510) is entirely removed from the first guide lumen 514, the first original catheter 506 (or alternatively the first replacement catheter 510) is said to be positioned in a "removed position." Similarly, when the second original catheter 508 (or alternatively the second replacement catheter 512) is entirely removed from the second guide lumen 516, the second original catheter 508 (or alternatively the second replacement catheter 512) is also said to be positioned in a "removed position."

When the first original catheter 506 (and the first replacement catheter 510) is positioned in the inserted position, the distal segment 558 of the first original catheter 506 (and the first replacement catheter 510) extends out of the first distal guide orifice 520 of the guide catheter 502 as shown in FIG. 25. Similarly, when the second original catheter 508 (and the second replacement catheter 512) is positioned in the inserted position, the distal segment 560 of the second original catheter 508 (and the second replacement catheter 512) extends out of the distal guide orifice 524 of the guide catheter 504 as shown in FIG. 25. Accordingly, the distal orifices 552, 556 are each respectively positioned outside of the guide lumens 514, 516 when the first original catheter 506 (and the first replacement catheter 510) and the second original catheter 508 (and the second replacement catheter 512) are located in their inserted position.

Moreover, when the first original catheter 506 (and the first replacement catheter 510) is located in the inserted position, the threaded cap 538 is positioned adjacent to the first set of external threads 534 such that the threaded cap 538 can be rotated relative to the first guide catheter 502 so as to lock the first original catheter 506 (and the first replacement catheter 510) to the first guide catheter 502. Similarly, when the second original catheter 508 (and the second replacement catheter 512) is located in the inserted position, the threaded cap 540 is positioned adjacent to the second set of external threads 536 such that the threaded cap 540 can be rotated relative to the second guide catheter 504 so as to lock the second original catheter 508 (and the second replacement catheter 512) to the second guide catheter 504.

The first guide catheter 502 is placed within the body 46 in substantially the same manner as was described hereinabove with respect to the placement of the guide catheter 32 of the catheter system 16 within the body 46 (i.e. by the tunneled catheter technique). Similarly, the second guide catheter 504 is placed within the body 46 in substantially the same manner as was described hereinabove with respect to the placement of the guide catheter 32 of the catheter system 16 within the body 46 (i.e. by the tunneled catheter technique). Once the first guide catheter 502 and the second guide catheter 504 are placed in the body 46 as described above, the first original catheter 506 and the second original catheter 508 are respectively advanced through the first guide lumen 514 of the guide catheter 502 and the second guide lumen 516 of the guide catheter 504 so that the distal orifices 552, 556 are respectively advanced out of the distal guide orifices 520, 524 and positioned within the superior vena cava 30 of the body 46. (In other words, the first original catheter 506 and the second original catheter 508 are respectively advanced to their inserted positions.) The first original catheter 506 and the second original catheter 508 are then respectively locked to the first guide catheter 502 and the second guide catheter 504 in the manner which has been previously described hereinabove.

Figure 30:
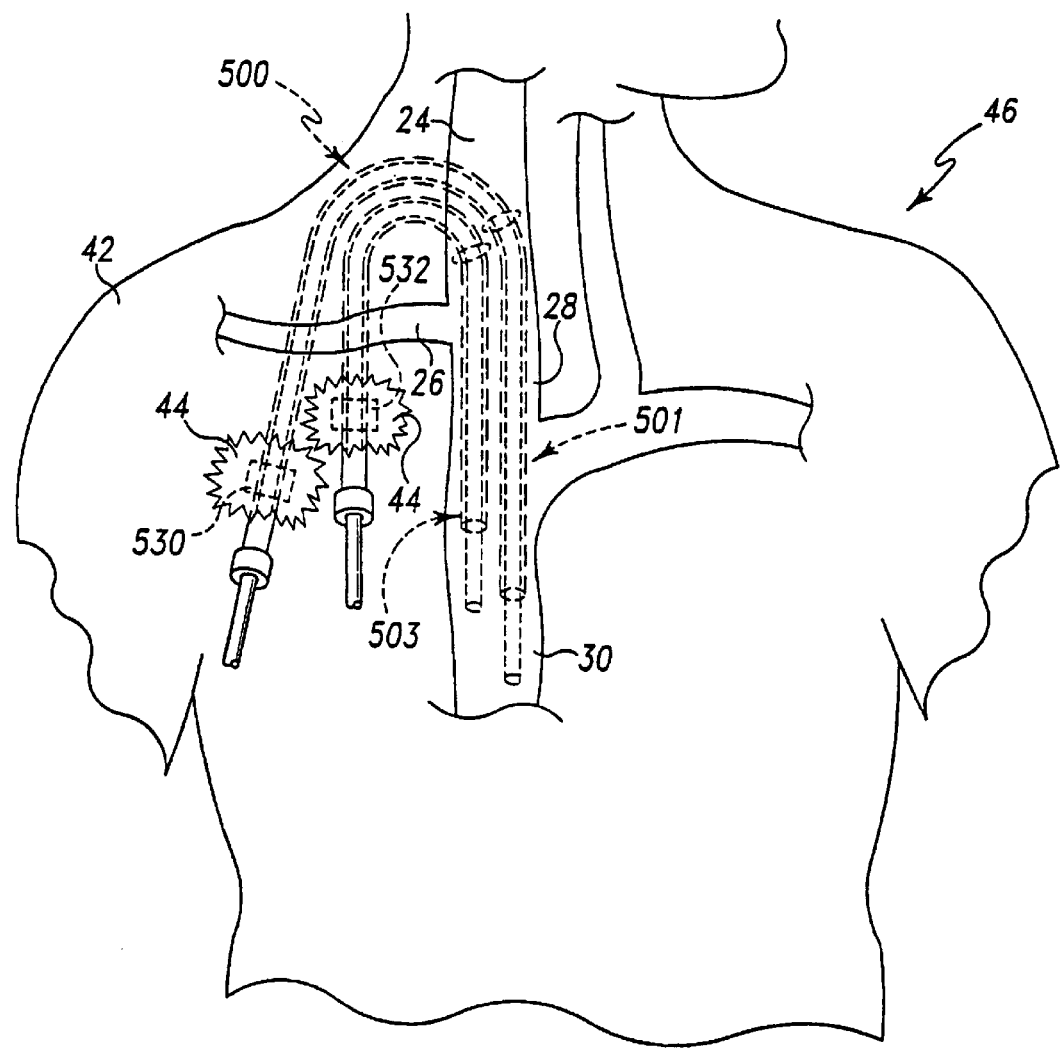
FIG. 30 is an enlarged view which is similar to FIG. 2, but showing the catheter system of FIG. 25 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

The catheter system 500 is shown in FIGS. 25–30 as being configured to allow removal and replacement of (i) the first original catheter 506 of the first catheter apparatus 501, as well as (ii) the second original catheter 508 of the second catheter apparatus 503. However, it should be appreciated that a first alternative arrangement (not shown) to the arrangement described in FIGS. 25–30 is to configure the second catheter apparatus 503 to be exactly the same as shown in FIGS. 25 and 30, but to configure the first catheter apparatus 501 to be similar to a conventional single lumen catheter (i.e. a catheter apparatus which does not possess a removable/replaceable inner conduit). It should be further appreciated that a second alternative arrangement (not shown) to the arrangement described in FIGS. 25–30 is to configure the first catheter apparatus 501 to be exactly the same as shown in FIGS. 25 and 30, but to configure the second catheter apparatus 503 to be similar to a conventional single lumen catheter (i.e. a catheter apparatus which does not possess a removable/replaceable inner conduit).

V(a). First Manner of Using Catheter System 500

According to a first preferred manner of using the catheter system 500, the first original catheter 506 is replaced with the first replacement catheter 510 only after it becomes substantially inoperative due to partial or total occlusion of its lumen 550 as a result of, for example, blood clot build-up. Moreover, the second original catheter 508 is replaced with the second replacement catheter 512 only after it becomes substantially inoperative due to partial or total occlusion of its lumen 554 as a result of, for example, blood clot build-up. Such a manner of using the catheter system 500 would be substantially similar to the manner of using the catheter system 16 which was discussed herein in section 1(a) entitled "First Manner of Using Catheter System 16". However, it should be noted that it is possible, and may even be likely, that the first original catheter 506 (and the first replacement catheter 510) will be replaced due to, for example, blood clot build-up at a lower frequency in comparison to the replacement of the second original catheter 508 (and the second replacement catheter 512) due to, for example, blood clot build-up. Such lower frequency of replacement may be due to the fact that during use of the catheter system 500, blood is infused into the vascular system 22 with the first original catheter 506 (and the first replacement catheter 510). In contrast, during use of the catheter system 500, blood is withdrawn from of the vascular system 22 with the second original catheter 508 (and the second replacement catheter 512). Again, historically, occlusion problems occur more frequently during a dialysis procedure when attempting to withdraw blood from a patient's vascular system through a dialysis catheter in comparison to attempting to infuse blood back into a patient's vascular system through the dialysis catheter.

V(b). Second Manner of Using Catheter System 500

In accordance with a second preferred manner of using the catheter system 500, each of the first original catheter 506 and the second original catheter 508 is a "single use" catheter. In other words, both the first original catheter 506 and the second original catheter 508 of catheter system 500 are only used for a single dialysis session, and thereafter discarded. Hence, both the first original catheter 506 and the second original catheter 508 would typically never be left in the vascular system 22 long enough to become substantially inoperative due to partial or total occlusion of its lumens 550, 554 as a result of, for example, blood clot build-up. Such a manner of using the catheter system 500 would be substantially similar to the manner of using the catheter system 16 which was discussed herein in section 1(b) entitled "Second Manner of Using Catheter System 16".

Note that between dialysis sessions, when the first original catheter 506 (or the first replacement catheter 510) is not located within the guide lumen 514 of the first guide catheter 502, a first closure member 563, such as a cap, is secured to the guide catheter 502 so as to cover the first proximal guide orifice 518. Optionally, a clamp (not shown) which is similar in construction and function to the clamp 101 of the catheter system 16 (see FIG. 11) may also be positioned on the guide catheter 502 near the first proximal guide orifice 518 between dialysis sessions. Also note that between dialysis sessions, when the second original catheter 508 (or the second replacement catheter 512) is not located within the second guide lumen 516 of the second guide catheter 504, a second closure member 565, such as another cap, is secured to the second guide catheter 504 so as to cover the second proximal guide orifice 522. Optionally, another clamp (not shown) which is similar in construction and function to the clamp 101 of the catheter system 16 (see FIG. 11) may also be positioned on the guide catheter 504 near the second proximal guide orifice 522 between dialysis sessions. The closure members 563, 565 are substantially identical in construction and function to the closure member 100 of the catheter system 16 shown in FIGS. 11–13.

Obviously, when the patient desires to be dialyzed again, the guide catheters 502, 504 are prepped in a sterile manner such as by applying an antibacterial solution thereto. Thereafter, the closure members 563, 565 would be respectively unlocked from the guide catheters 502, 504, and thereafter the replacement catheters 510, 512 would be respectively inserted into the guide lumens 514, 516 and then respectively locked to the guide catheters 502, 504 as hereinabove described. Again, this manner of using the catheter system 500 would be substantially similar to the manner of using the catheter system 16 which was discussed herein in section 1(b) entitled "Second Manner of Using Catheter System 16".

Also, please note that according to the second manner of using the catheter system 500, the original catheters 506, 508 and the replacement catheters 510, 512 are only a "single use" catheters. Accordingly, the physical structure of the catheters 506, 508, 510, 512 of the catheter system 500 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

V(c). Third Manner of Using Catheter System 500

According to a third preferred manner of using the catheter system 500, the first original catheter 506 is replaced with the first replacement catheter 510, as described above, after any predetermined number of dialysis sessions is performed. Moreover, the second original catheter 508 is replaced with the second replacement catheter 512, as described above, after any predetermined number of dialysis sessions is performed. For example, such predetermined number may be (i) determined from experimental studies, (ii) determined based on patient history, or (iii) determined based on other criteria. Such a manner of using the catheter system 500 would be substantially similar to the manner of using the catheter system 16 which was discussed herein in section 1(c) entitled "Third Manner of Using Catheter System 16". In addition, the predetermined number of dialysis sessions after which the first original catheter 506 is replaced does not necessarily have to be equal to the predetermined number of dialysis sessions after which the second original catheter 508 is replaced. For example, the first original catheter 506 may be replaced with a first replacement catheter 510 after every four dialysis sessions, while the second original catheter 508 may be replaced with a second replacement catheter 512 after every three dialysis sessions.

VI. Catheter System 600

FIGS. 31–34 shows a catheter system 600 which additionally incorporates the features of the present invention therein. The catheter system 600 may be used for the administration of total parenteral nutrition (hereinafter referred to as "TPN") to a patient. TPN generally refers to a nutritive solution which is fed intravenously via an indwelling central venous catheter in conditions where patients cannot eat by mouth or receive nutrition enterally (e.g. by gastric tube or small bowel tube). Some examples where prolonged administration of TPN to a patient are indicated include instances where a patient suffers from an insufficient small bowel absorptive area such as short gut syndrome or an instance where a patient suffers from prolonged intestinal ileus which may have resulted due to a severe burn injury or an abdominal surgery. Other examples where prolonged administration of TPN to a patient are indicated include instances where a patient has a condition requiring prolonged bowel rest such as where the patient suffers from pancreatitis or inflammatory bowel disease. Yet another example where prolonged administration of TPN to a patient is indicated is the situation where a patient refuses to eat such as would occur in the case of severe anorexia nervosa.

Figure 31:
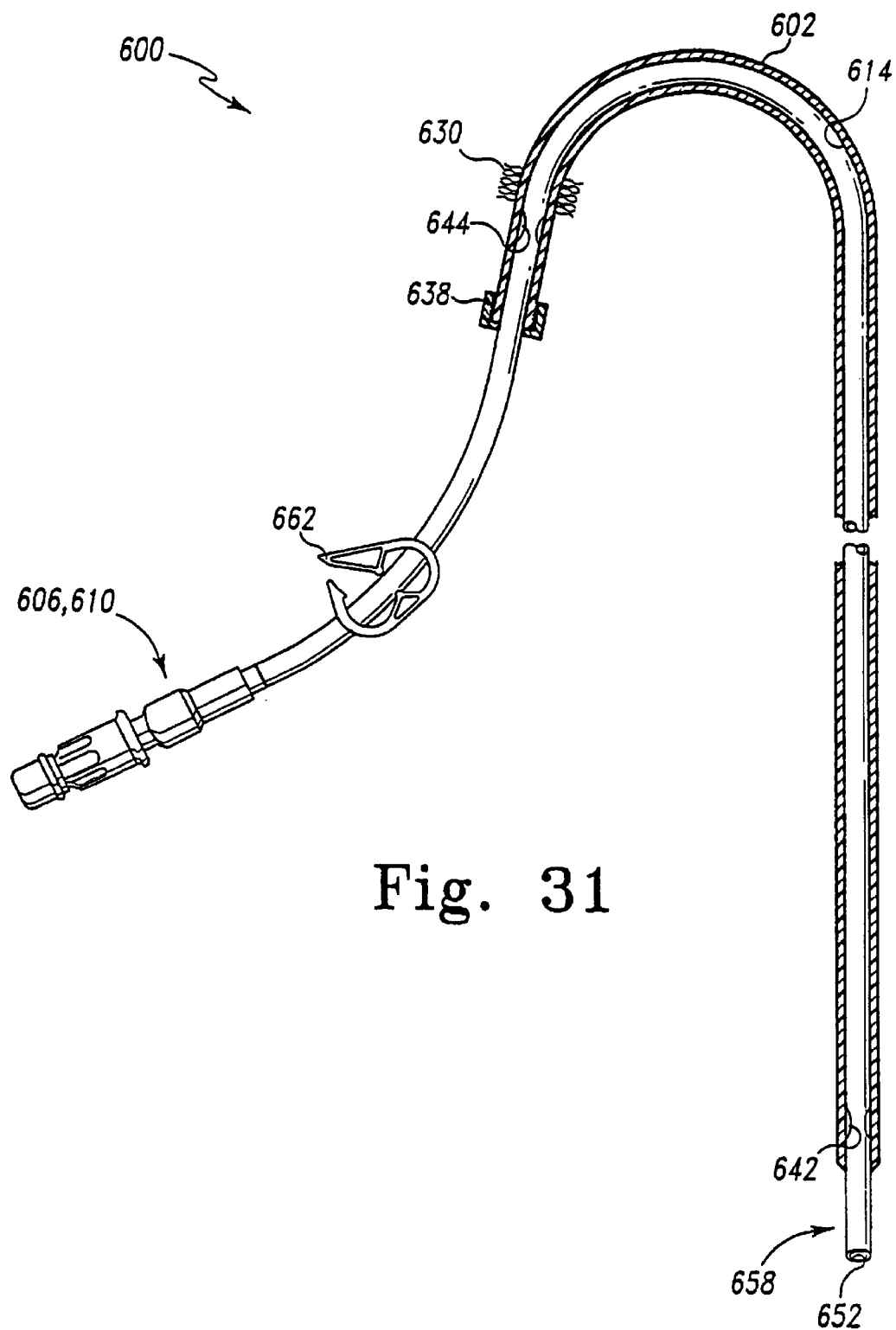
FIG. 31 is a view similar to FIG. 3, but showing still another catheter system which incorporates the features of the present invention therein.

Referring now in detail to FIGS. 31–34, the catheter system 600 includes a guide catheter 602 and an original single lumen catheter 606. The catheter system 600 further includes a replacement single lumen catheter 610 as will be discussed below. The guide catheter 602 has a guide lumen 614 which extends along the length of the guide catheter 602 as shown in FIG. 31. The guide lumen 614 defines a proximal guide orifice 618 and a distal guide orifice 620. The original catheter 606 is able to be positioned within the guide lumen 614 of the guide catheter 602 as shown in FIG. 31. Similarly, the replacement catheter 610 is also able to be positioned within the guide lumen 614 of the guide catheter 602 as shown in FIG. 31.

Figure 33:
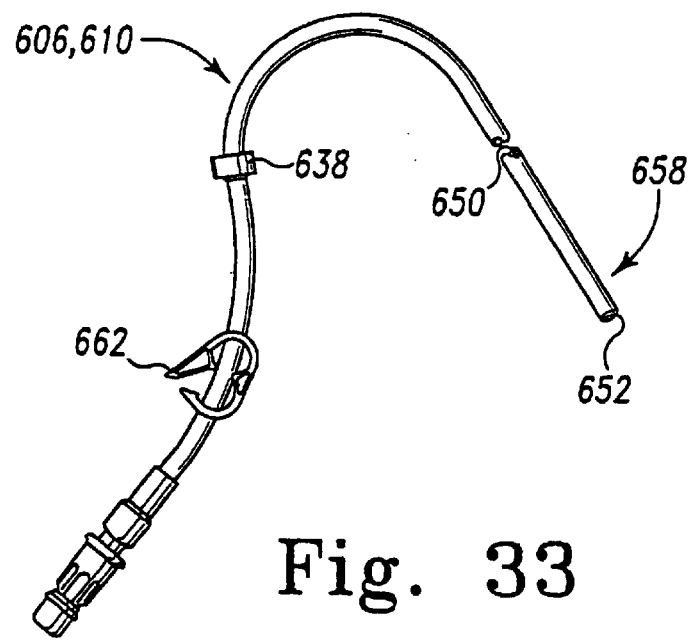
FIG. 33 is a side elevational view of the original catheter of the catheter system shown in FIG. 31.
Figure 34:
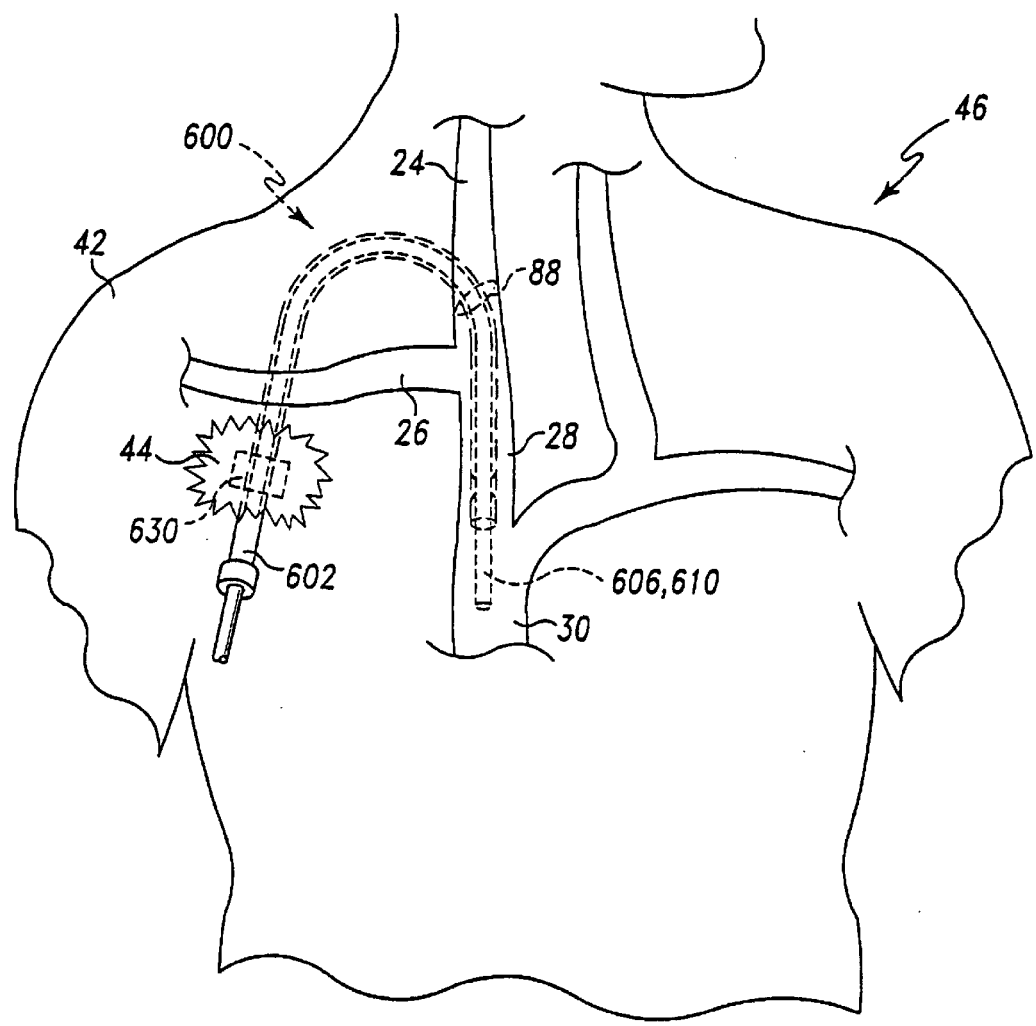
FIG. 34 is an enlarged view which is similar to FIG. 2, but showing the catheter system of FIG. 31 (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Note that the original catheter 606 possesses the same physical construction and configuration as the replacement catheter 610. Thus, for convenience of description, FIGS. 31, 33, and 34 show reference numerals 606 and 610 identifying the same catheter. However, the original catheter 606 will be located within the guide lumen 614 during a first period of time, while the first replacement catheter 610 will be located within the guide lumen 614 during a second period of time which is after the first period of time.

In particular, according to one preferred manner of using the catheter system 600 during a TPN administration session, the original catheter 606 is positioned within the guide lumen 614 of the guide catheter 602 for a first period of time during which TPN is infused therethrough. After the first period of time, the flow through the lumen of the original catheter 606 may become partially or even totally inhibited due to, for example, blood clot build-up. In order to remedy this problem, the original catheter 606 is withdrawn from the guide lumen 614, and thereafter, the replacement catheter 610 is positioned within the guide lumen 614 (and locked to the guide catheter 602) for a subsequent second period of time during which TPN is again infused therethrough.

Figure 32:
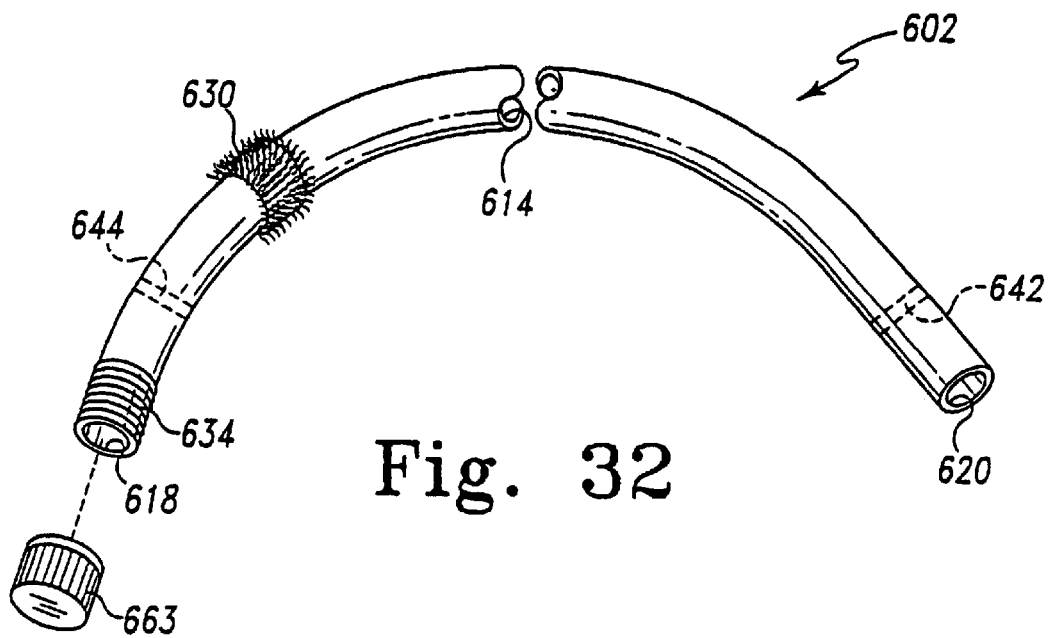
FIG. 32 is a side elevational view of the guide catheter of the catheter system shown in FIG. 31.

Referring to FIGS. 31, 32, and 34, the guide catheter 602 has a tissue ingrowth member 630 secured to an outer surface thereof. The tissue ingrowth member 630 is substantially identical to the tissue ingrowth member 38 described hereinabove with regard to the catheter system 16.

As shown in FIGS. 31 and 32, the guide catheter 602 includes a set of external threads 634 defined on an outer surface thereof near the first proximal guide orifice 618. The set of external threads 634 cooperate with an internally threaded cap 638 of the original catheter 606 (and the replacement catheter 610) to lock the original catheter 606 (and the replacement catheter 610) to the guide catheter 602 as shown in FIG. 31. The cap 638 is substantially identical to the cap 67 which was described hereinabove with regard to catheter system 16. Moreover, each of the catheters 606, 610 are provided with an upper tab and a lower tab, similar to tabs 68, 69 of the catheter system 16 described above (see FIG. 6), to rotatably retain the cap 638 in place.

While the original catheter 606 and the replacement catheter 610 are described as being respectively locked to the guide catheter 602 using a locking arrangement which utilizes cooperating internal and external threads, and has substantial benefits thereby, numerous other arrangements may alternatively be incorporated into the catheter system 600 to function to respectively lock the original catheter 606 and the replacement catheter 610 to the guide catheter 602 and still achieve many of the advantages of the present invention. For example, the detent and groove type locking arrangement (not shown) or the leg and guide channel type locking arrangement (not shown) which were described above in regard to catheter system 16 may be utilized to respectively lock the original catheter 606 and the replacement catheter 610 to the guide catheter 602.

The guide catheter 602 further includes a distal blood flow valve 642 and a proximal blood flow valve 644 positioned within the guide lumen 614 as shown in FIGS. 31 and 32. The blood flow valves 642, 644 are substantially identical to the blood flow valves 62 and 70 which were described hereinabove with regard to the catheter system 16.

Referring again to FIGS. 31, 33, and 34, the original catheter 606 (and the replacement catheter 610) includes a lumen 650. The lumen 650 defines a distal orifice 652. The distal orifice 652 is defined in a distal segment 658 of the original catheter 606 (and the replacement catheter 610).

A clamp 662 is positioned on the original catheter 606 (and the replacement catheter 610). The clamp 662 is substantially identical in construction and function to the clamps 82, 84 discussed hereinabove with regard to the catheter system 16.

The original catheter 606 (and the replacement catheter 610) may be positioned within the guide lumen 614 of the guide catheter 602 as shown in FIG. 31. When the original catheter 606 (or alternatively the replacement catheter 610) is positioned within the guide lumen 614 as shown in FIG. 31, the original catheter 606 (or alternatively the replacement catheter 610) is said to be positioned in an "inserted position." When the original catheter 606 (or alternatively the replacement catheter 610) is entirely removed from the guide lumen 614, the original catheter 606 (or alternatively the replacement catheter 610) is said to be positioned in a "removed position."

When the original catheter 606 (and the replacement catheter 610) is positioned in the inserted position, the distal segment 658 of the original catheter 606 (and the replacement catheter 610) extends out of the distal guide orifice 620 of the guide catheter 602 as shown in FIG. 31. Accordingly, the distal orifice 652 is positioned outside of the guide lumen 614 when the original catheter 606 (and the replacement catheter 610) is located in its inserted position.

Moreover, when the original catheter 606 (and the replacement catheter 610) is located in the inserted position, the threaded cap 638 is positioned adjacent to the set of external threads 634 such that the threaded cap 638 can be rotated relative to the guide catheter 602 so as to lock the original catheter 606 (and the replacement catheter 610) to the guide catheter 602.

The guide catheter 602 is placed within the body 46 in substantially the same manner as was described hereinabove with respect to the placement of the guide catheter 32 of the catheter system 16 within the body 46 (i.e. by the tunneled catheter technique). Once the guide catheter 602 is placed in the body 46 as described above, the original catheter 606 is advanced through the guide lumen 614 of the guide catheter 602 so that the distal orifice 652 is advanced out of the distal guide orifice 620 and positioned within the superior vena cava 30 of the body 46. (In other words, the original catheter 606 is advanced to its inserted position.) The original catheter 606 is then locked to the guide catheter 602 in the manner which has been previously described hereinabove.

Figure 35:
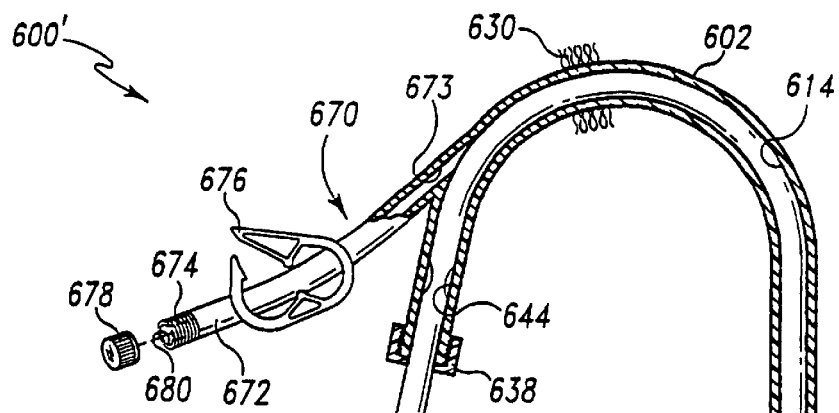
FIG. 35 is a view similar to FIG. 31, but showing another catheter system which incorporates the features of the present invention therein.
Figure 37:
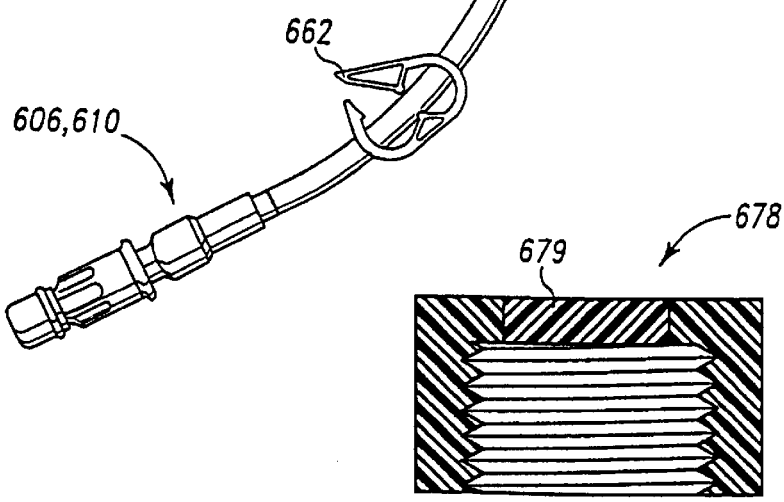
FIG. 37 is an enlarged cross sectional view of the closure member of FIG. 36 taken along the line 37—37 of FIG. 36 as viewed in the direction of the arrows.
Figure 36:
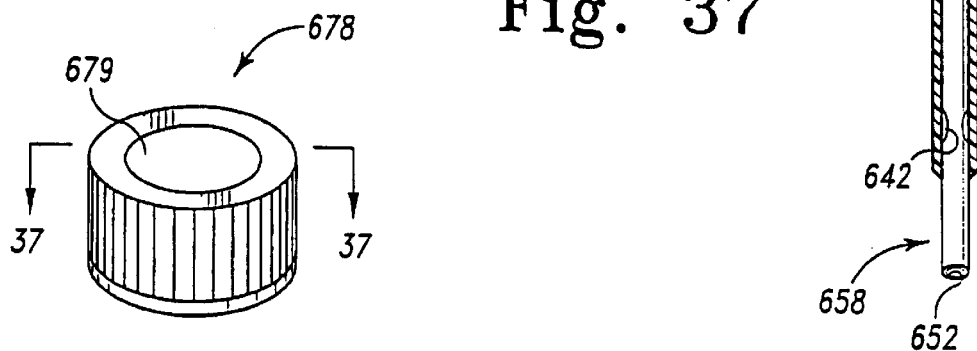
FIG. 36 is an enlarged perspective view of the closure member of FIG. 35.

An alternative configuration for the catheter system 600 is shown in FIG. 35. In particular, this alternative embodiment of the present invention shows a catheter system 600'. The catheter system 600' is used in substantially the same manner as herein described with respect to the catheter system 600. Moreover, the catheter system 600' is exactly the same in construction and configuration as the catheter system 600 shown in FIGS. 31–34, with the exception that the catheter system 600' includes a sideport 670 through which fluid may be withdrawn or advanced. In particular, the sideport 670 includes a conduit 672 having a set of external threads 674 defined on a proximal end thereof. A clamp 676 is positioned on the conduit 672. The clamp 662 is substantially identical in construction and function to the clamps 82, 84 discussed hereinabove with regard to the catheter system 16. The conduit 672 defines a sideport lumen 673 which is in fluid communication with the guide lumen 614. Accordingly, air can be aspirated out of the guide lumen 614 through the sideport 670 via the conduit 672. Alternatively, the guide lumen 614 may be flushed with a fluid such as a saline, heparin, or urokinase solution between uses of the catheter system 600' (e.g. administration of TPN to a patient). It should be noted that the guide lumen 614 may even be flushed with a saline, heparin, or urokinase solution while the original catheter 606 (or the replacement catheter 610) is located within the guide lumen 614. When not in use, the sideport 670 may be clamped shut with the clamp 676. Moreover, when not in use a closure member or cap 678 may be secured to the conduit 672 to cover a proximal sideport orifice 680 which is defined by the conduit 672. The cap 678 is provided with a set of internal threads which cooperate with the set of external threads 674 so as to lock the cap 678 to the guide catheter 602. Optionally, the cap 678 may be provided with a silicone membrane 679, as shown in FIGS. 36–37, which may be traversed with a needle whereby a saline, heparin, or urokinase solution may be advanced into the conduit 672 in order to flush the guide catheter 602.

It should be noted that any of the other embodiments of the present invention set forth herein (e.g. catheter systems 16, 200, 300, 400, and 500) may be modified to incorporate a sideport which is similar to sideport 670. In particular, any of the guide catheters of the catheter systems 16, 200, 300,400, and 500 may be modified to include a sideport which is similar in construction, configuration, and use to the construction, configuration and use of the sideport 670 described herein.

Figure 38:
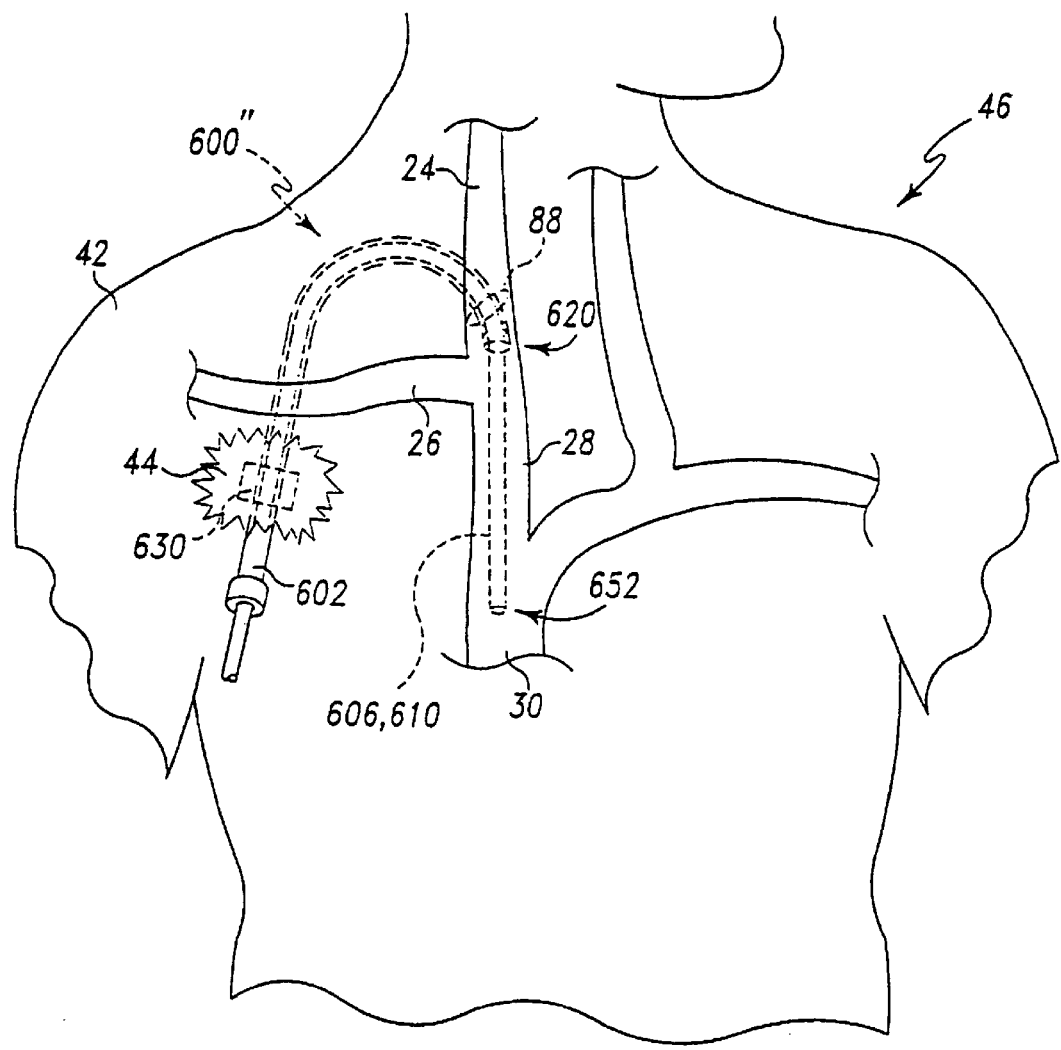
FIG. 38 is an enlarged view which is similar to FIG. 2, but showing still another catheter system which incorporates the features of the present invention therein (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.

Another alternative configuration for the catheter system 600 is shown in FIG. 38. In particular, FIG. 38 shows another catheter system 600" which also incorporates features of the present invention therein. The catheter system 600" is used in substantially the same manner as herein described with respect to the catheter system 600. Moreover, the catheter system 600" is exactly the same in construction and configuration as the catheter system 600 shown in FIGS. 31–34, with the exception that the guide catheter 602 of the catheter system 600" is much shorter in length than the guide catheter 602 of the catheter system 600, while the original catheter 606 (and replacement catheter 610) of the catheter system 600" is the same length as the original catheter 606 (and the replacement catheter 610) of the catheter system 600. (For example, compare FIG. 38 with FIG. 34). In particular, the length of the guide catheter 602 of the catheter system 600" is such that after it is placed in the body 46 as shown in FIG. 38, its distal guide orifice 620 is located in the right internal jugular vein 24 preferably approximately five centimeters distal to the venotomy 88. Moreover, in this embodiment of the present invention shown in FIG. 38, the distance between the distal orifice 652 of the original catheter 606 (and the replacement catheter 610) and the distal guide orifice 620 of the guide catheter 602 is preferably approximately fifteen centimeters. In contrast, in the embodiment shown in FIGS. 31–34, the distance between the distal orifice 652 of the original catheter 606 (and the replacement catheter 610) and the distal guide orifice 620 of the guide catheter 602 is preferably approximately three centimeters. The catheter system 600", which possesses such a relatively shorter guide catheter 602, is configured so as to eliminate the presence of a long-term intravascular catheter structure within the right innominate vein 28 and the superior vena cava 30. In particular, the only catheter structure of the catheter system 600" that remains in the vascular system 22 on a long-term basis is the distal portion of the relatively shorter guide catheter 602 which is shown in FIG. 38. This long-term intravascular catheter structure only extends within the right internal jugular vein 24 from the venotomy 88 to the distal guide orifice 620 as shown in FIG. 38. Note that the right internal jugular vein 24 is not part of a major venous return flow path for the right upper extremity of the patient's body as is the right innominate vein 28 and the superior vena cava 30. While the inner catheter 606 (or 610) does extend within the right innominate vein 28 and the superior vena cava 30 while a dialysis session is being conducted as shown in FIG. 38, such a dialysis session is typically conducted only approximately three times per week, and each session lasts for only approximately four hours. Thus, it should be appreciated that, if the inner catheter 606, 610 is removed after each dialysis session, even though the guide catheter 602 of the catheter system 600" is located within the body and the patient is not engaging in a dialysis session, there exists no intravascular catheter structure present in the right innominate vein 28 and the superior vena cava 30. Note that by eliminating the presence of a long-term intravascular catheter structure from the right innominate vein 28 and the superior vena cava 30, the development of central vein stenosis due to, for example, prolonged physical contact between the intravascular catheter structure and the internal sidewall of the right innominate vein 28 and/or the internal sidewall of the superior vena cava 30 may be prevented. It should be appreciated that the fluid path which includes the right subclavian vein 26, the right innominate vein 28 and the superior vena cava 30 represents a major venous return flow path, especially in the case where an arteriovenous fistula has been created or an arteriovenous dialysis graft has been implanted in the right upper extremity of the patient's body. Preventing central venous stenosis within such a major venous return flow path is quite beneficial to a patient, e.g. a dialysis patient.

Figure 38A:
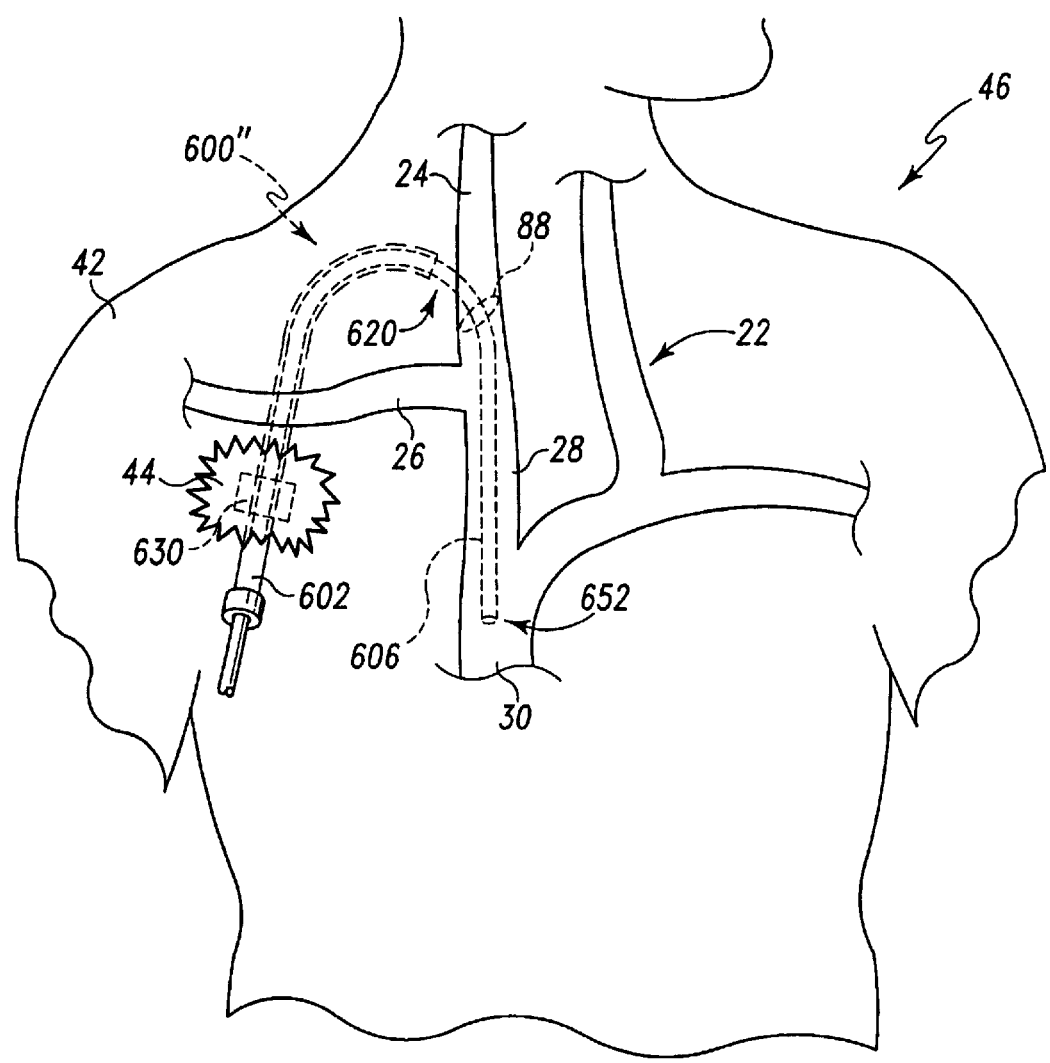
FIG. 38A is a view similar to FIG. 38, but showing yet another catheter system which incorporates the features of the present invention therein (i) extending from the right upper chest, (ii) tunneled under the skin within the subcutaneous tissue of the patient for a distance, (iii) entering a venotomy in the right internal jugular vein, and (iv) passing caudally in the right internal jugular vein, the right innominate vein and the superior vena cava.
Figure 38B:
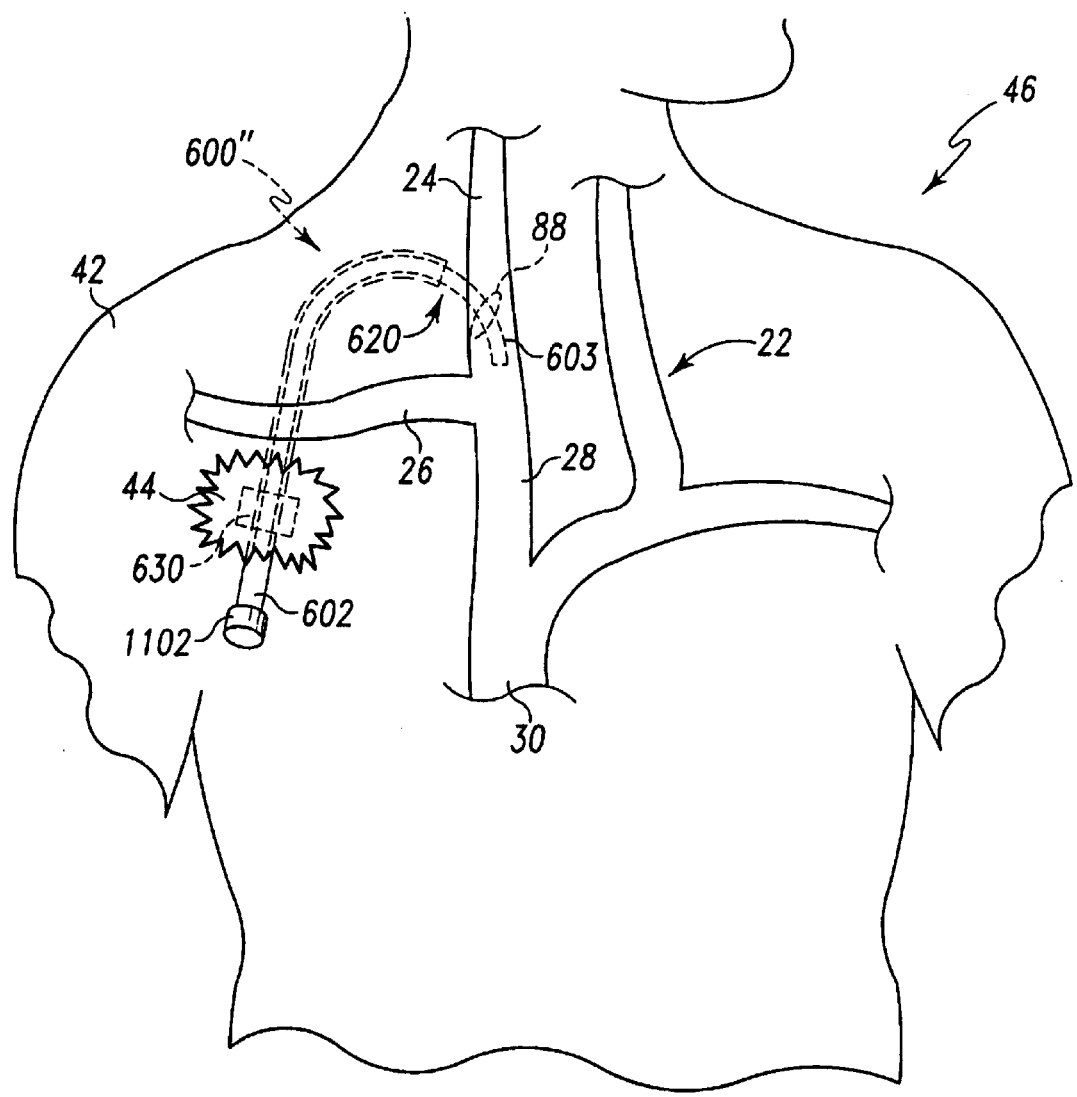
FIG. 38B is a view similar to FIG. 38A, but showing the dialysis catheter of the catheter system of FIG. 38A removed from the guide catheter and the dummy catheter of the catheter system of FIG. 38A positioned within the guide catheter.

Yet still another alternative configuration for the catheter system 600 is shown in FIGS. 38A and 38B. In particular, FIGS. 38A and 38B show yet another catheter system, indicated also as catheter system 600" for convenience of description, which incorporates features of the present invention therein. The catheter system 600" of FIGS. 38A and 38B is used in substantially the same manner as herein described with respect to the catheter system 600. Moreover, the catheter system 600" of FIGS. 38A and 38B is exactly the same in construction and configuration as the catheter system 600 shown in FIGS. 31–34, with the exception that the guide catheter 602 of the catheter system 600" is much shorter in length than the guide catheter 602 of the catheter system 600, while the original catheter 606 (and replacement catheter 610) of the catheter system 600" of FIGS. 38A and 38B is the same length as the original catheter 606 (and the replacement catheter 610) of the catheter system 600. (For example, compare FIGS. 38A and 38B with FIG. 34). In particular, the length of the guide catheter 602 of the catheter system 600" of FIGS. 38A and 38B is such that after it is placed in the body 46 as shown in FIGS. 38A and 38B, its distal guide orifice 620 is located entirely outside of the vascular system 22 in the subcutaneous tissue 44 preferably two centimeters proximal to the venotomy 88. Moreover, in this embodiment of the present invention shown in FIGS. 38A and 38B, the distance between the distal orifice 652 of the original catheter 606 (and the replacement catheter 610) and the distal guide orifice 620 of the guide catheter 602 is preferably approximately twenty-two centimeters. In contrast, in the embodiment shown in FIGS. 31–34, the distance between the distal orifice 652 of the original catheter 606 (and the replacement catheter 610) and the distal guide orifice 620 of the guide catheter 602 is preferably approximately three centimeters. The catheter system 600" of FIGS. 38A and 38B, which possesses such a relatively shorter guide catheter 602, is also configured so as to eliminate the presence of a long-term intravascular catheter structure within the right innominate vein 28 and the superior vena cava 30, and thereby achieve the corresponding benefits discussed above.

Figure 38C:
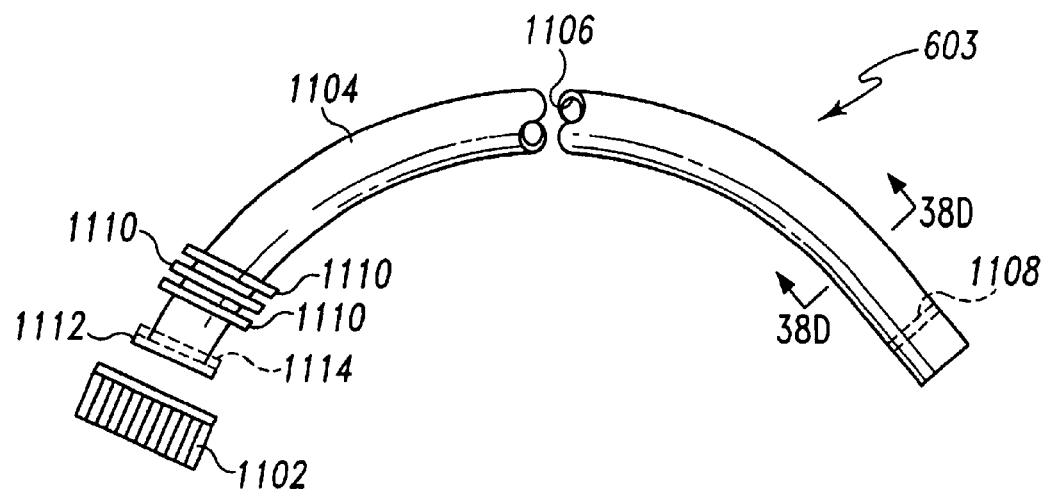
FIG. 38C is an enlarged side elevational view of the dummy catheter and cap of the catheter system of FIG. 38A.
Figure 38D:
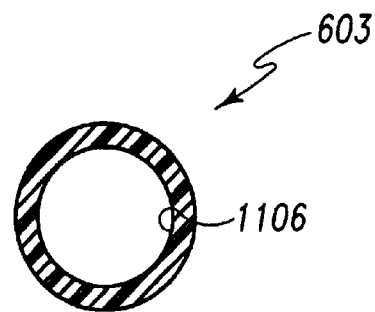
FIG. 38D is an enlarged cross sectional view taken along the line 38D—38D of FIG. 38C as viewed in the direction of the arrows.

The catheter system 600" of FIGS. 38A and 38B differs from the catheter system 600" of FIG. 38 in that it further includes a dummy catheter 603 as shown in FIGS. 38B, 38C, and 38D. The dummy catheter 603 is configured to occupy most of the space of the guide lumen of the guide catheter 602 as shown in FIG. 38B. The dummy catheter 603 includes an internally threaded cap 1102 similar to the cap shown in FIGS. 12 and 13. The dummy catheter 603 further includes a tubular body portion 1104 that defines a lumen 1106 that extends from the proximal end of the body portion 1104 to the distal end of the body portion. A valve 1108 is secured within the distal end portion of the body portion 1104 as shown in FIG. 38C. The dummy catheter 603 further includes a plurality of elastic seal members 1110 secured to the body portion 1104. Note that when the dummy catheter 603 is located within the guide catheter 602 as shown in FIG. 38B, the elastic seal members 1110 are urged against the inner sidewall of the guide catheter 602 so as to provide added security against fluid leakage into and out of the body 46 through the guide catheter 602. Also, when the dummy catheter 603 is located within the guide catheter 602 as shown in FIG. 38B, a lip 1112 of the body portion 1104 contacts the proximal end of the guide catheter 602 so as to create a leakproof seal therebetween. As the cap 1102 is screwed onto the proximal end of the guide catheter 602, the cap 1102 urges the lip 1112 into sealing contact with the proximal end of the guide catheter 602. A supplemental elastic sealing ring 1114 (shown in phantom in FIG. 38C) may be secured around the body portion 1104 just below the lip 1112 in order to enhance the integrity of the seal between the guide catheter 602 and the body portion 1104.

It should be appreciated that placement of the dummy catheter into the vascular system 22 between dialysis sessions helps ensure that quick access to the vascular system 22 is obtained when a replacement dialysis catheter is desired to be placed within the vascular system to carry out a new dialysis procedure. Note that since the body portion 1104 of the dummy catheter 603 possesses a lumen (i.e.

lumen 1106) which extends therethrough, a guide wire (not shown) may be used to exchange the dialysis catheter (e.g. dialysis catheter 606) for the dummy catheter 603 after completion of a dialysis session, and also exchange the dummy catheter 603 for a replacement dialysis catheter (e.g. replacement dialysis catheter 610) prior to commencement of a subsequent dialysis session. Catheter exchange with the aid of a guide wire is well know to one skilled in the art and need not be described in detail.

It should be noted that any of the guide catheters of the catheter systems 16, 200, 300, 400, 500, and 600' may be modified to include a guide catheter which is similar in construction, configuration, and use to the construction, configuration and use of the guide catheter 602 of the catheter system 600" described herein. In particular, any of the other embodiments of the catheter systems of the present invention set forth herein (e.g. catheter systems 16, 200, 300, 400, 500, 600') may be modified to incorporate a relatively short guide catheter similar to the guide catheter 602 of the catheter system 600" (shown in FIG. 38, and FIGS. 38A and 38B) whereby (i) the distance between its distal orifice of the original catheter (and the replacement catheter) and its distal guide orifice of the guide catheter is preferably approximately fifteen centimeters (or more in the embodiment shown in FIGS. 38A and 38B), and (ii) the length of such shorter guide catheter is such that after it is placed in the body 46, its distal guide orifice of the guide catheter is located in the right internal jugular vein 24 preferably approximately five centimeters distal to the venotomy 88 (or is located entirely outside of the vascular system 22 as shown in FIGS. 38A and 38B).

VI(a). First Manner of Using Catheter System 600

According to a first preferred manner of using the catheter system 600, the original catheter 606 is replaced with the replacement catheter 610 only after it becomes substantially inoperative due to partial or total occlusion of its lumen 650. Such a manner of using the catheter system 600 would be substantially similar to the manner of using the catheter system 16 which was discussed herein in section 1(a) entitled "First Manner of Using Catheter System 16".

VI(b). Second Manner of Using Catheter System 600

In accordance with a second preferred manner of using the catheter system 600, the original catheter 606 is a "single use" catheter. In other words, the original catheter 606 of the catheter system 600 is only used for a single TPN administration session, and thereafter discarded. Hence, the original catheter 606 would typically never be left in the vascular system 22 long enough to become substantially inoperative due to partial or total occlusion of its lumen 650. Such a manner of using the catheter system 600 would be substantially similar to the manner of using the catheter system 16 which was discussed herein in section 1(b) entitled "Second Manner of Using Catheter System 16".

Note that between TPN administration sessions, when the original catheter 606 (and the replacement catheter 610) is not located within the guide lumen 614 of the guide catheter 602, a first closure member 663, such as a cap, is secured to the guide catheter 602 so as to cover the proximal guide orifice 618. The closure member 663 is substantially identical in construction and function to the closure member 100 of the catheter system 16 shown in FIGS. 11–13. Optionally, a clamp (not shown) which is similar in construction and function to the clamp 101 of the catheter system 16 (see FIG. 11) may also be positioned on the guide catheter 602 near the proximal guide orifice 618 between TPN administration sessions.

When the patient desires to engage in another TPN administration session, the guide catheter 602 is prepped in a sterile manner such as by applying an antibacterial solution thereto. Thereafter, the closure member 663 would be unlocked from the guide catheter 602, and thereafter the replacement catheter 606 would be inserted into the guide lumen 614 and then locked to the guide catheter 602 as hereinabove described. Again, this manner of using the catheter system 600 would be substantially similar to the manner of using the catheter system 16 which was discussed herein in section 1(b) entitled "Second Manner of Using Catheter System 16".

Also, please note that according to the second manner of using the catheter system 600, the original catheter 606 and the replacement catheter 610 are only "single use" catheters. Accordingly, the physical structure of the catheters 606, 610 of the catheter system 600 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

VI(c). Third Manner of Using Catheter System 600

According to a third preferred manner of using the catheter system 600, the original catheter 606 is replaced with the replacement catheter 610 after any predetermined number of TPN administration sessions is performed. For example, such predetermined number may be (i) determined from experimental studies, (ii) determined based on patient history, or (iii) determined based on other criteria. Such a manner of using the catheter system 600 would be substantially similar to the manner of using the catheter system 16 which was discussed herein in section 1(c) entitled "Third Manner of Using Catheter System 16".

VII. Conclusion

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

For instance, while the above-described dual-lumen catheter systems (e.g. catheter systems 16, 200, 300, 400, and 500) were discussed as being effective to perform hemodialysis, such catheter systems can also be utilized to perform other medical procedures in which dual-lumen catheter access to the vascular system (e.g. the central venous system) is required. One example of such a medical procedure is plasmapheresis in which blood is withdrawn from the vascular system, components of the blood are separated outside of the body, and a portion of the blood components are then returned to the vascular system.

In addition, another medical procedure which may be performed using the above-described dual-lumen catheter systems is peritoneal dialysis. In particular, catheter occlusion may occur during peritoneal dialysis, and such occlusion may be eliminated in a manner similar to that described above with respect to the catheter systems 16, 200, 300, 400, and 500.

Moreover, while the above-described single-lumen catheter systems (e.g. catheter systems 600, 600', 600") were discussed as being effective to perform administration of total parenteral nutrition, such catheter systems can be utilized to perform other medical procedures in which single-lumen catheter access to the vascular system is required. Examples of other medical procedures in which single-lumen catheter access to the vascular system is required includes (i) chemotherapy or other long-term medicinal infusions, (ii) repetitive blood transfusions, and (iii) repetitive blood samplings.

Furthermore, each of the above-described catheter systems (e.g. catheter systems 16, 200, 300, 400, 500, 600, 600', 600") were described as having a tissue ingrowth member (e.g. tissue ingrowth members 38, 320, 416, 530, 630) which is configured to facilitate attachment of such catheter system to the subcutaneous tissue 44 of the body. While the provision of such a tissue ingrowth member to effect attachment of such catheter system to the body of a patient has many advantages, the present invention may utilize other mechanisms which can function to attach such catheter system to the body on a long-term or even a short-term basis and still benefit from various advantages of the other features of the present invention. An example of such an attachment mechanism is a plastic member having a hole or recess for receiving a catheter therein and further having one or more wing-like or flap-like extensions which may be sutured or taped to the skin of the patient 46. Additionally, it is possible that the above-described catheters systems of the present invention (e.g. catheter systems 16, 200, 300, 400, 500, 600, 600', 600") may not include any mechanism which specifically functions to attach the catheter systems to the body yet still benefit from some of the advantages of the other features of the present invention.

Additionally, while each of the closure members 100, 350, 352, 432, 563, 565, 663, and 678 is disclosed as being locked to a respective guide catheter or sideport by an arrangement which includes cooperating internal and external threads and has advantages thereby, such closure members 100, 350, 352, 432, 563, 565, 663, and 678 may be locked to the respective guide catheter or sideport by other locking arrangements such as a conventional tamper-proof (or childproof) arrangement typically used on pill containers that contain prescription medication which is dispensed by a pharmacy.

While the above-described catheter systems 16, 200, 300, 400, 500, 600, 600' and 600" were described as being placed in the body 46 utilizing the permanent catheterization technique and has many advantages thereby, such catheter systems 16, 200, 300, 400, 500, 600, 600' and 600" could be placed in the body 46 utilizing other techniques (e.g. the temporary catheterization technique) and still achieve some of the advantages of the present invention.

Also, while the above described inner catheters 48, 58, 303, 304, 305, 306, 404, 406, 506, 508, 510, 512, 606, 610, were shown as only having a single hole or orifice defined in its distal segment through which fluid may be advanced, it should be appreciated that the distal segment of any of such inner catheters may have two or more holes defined in its distal segment each through which fluid may be advanced. For example, the distal segment of any of such inner catheters may have a single distal end hole (such as the distal orifice 336 of FIG. 17) and four additional holes defined in the sidewall of the distal segment, wherein each of the four additional holes is spaced apart from the distal end hole in the proximal direction by a distance.

Figure 51:
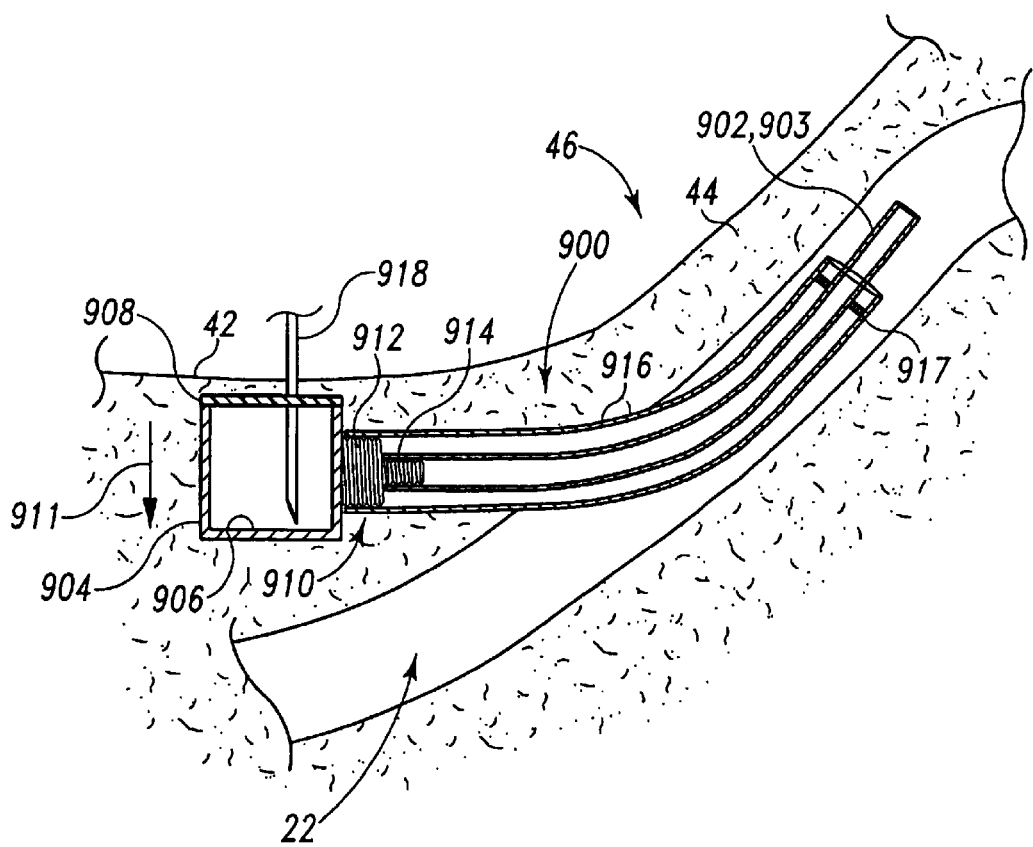
FIG. 51 is a side elevational view showing another catheter system that incorporates the features of the present invention therein.
Figure 52:
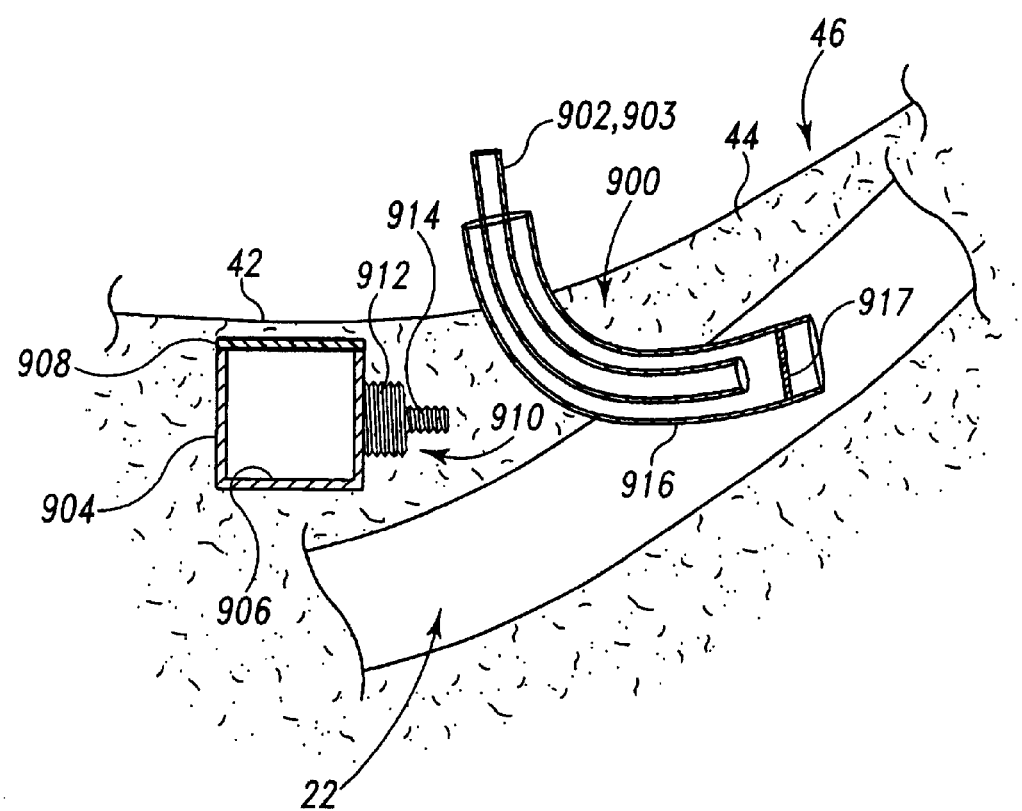
FIG. 52 is a view similar to FIG. 51, but showing replacement of the original inner catheter according to the method of the present invention.

Additionally, while the above-described catheter system 600 was described as being implanted in the body 46 so that a proximal portion of such respective catheter system is located external to the body 46 and the remainder of such respective catheter system is located within the body 46 (as shown in FIG. 34), such catheter system 600 could be implanted entirely within the body and still achieve some of the advantages of the present invention. More particularly, such respective catheter system 600 could be configured as a subcutaneous port catheter system 900 having an original inner catheter 902 (and a replacement inner catheter 903) as shown in FIGS. 51–52. The subcutaneous port catheter system 900 would be implanted entirely beneath the skin 42 of the body 46 within the subcutaneous tissue 44 (see FIG. 51). The subcutaneous port catheter system 900 further includes a reservoir 904 defining a chamber 906, and a septum 908 positioned over the chamber 906. The reservoir 904 includes an attachment cannula 910 which is in fluid communication with the chamber 906. The attachment cannula 910 includes an increased diameter portion 912 and a reduced diameter portion 914 each having a ribbed outer surface. The subcutaneous port catheter system 900 also includes a guide catheter 916 which is selectively attachable, via a friction fit, to the increased diameter portion 912. The guide catheter 916 may include a distal valve 917. Note that the original inner catheter 902 (and a replacement inner catheter 903) are selectively attachable, via a friction fit, to the reduced diameter portion 914. During use of the subcutaneous port catheter system 900, a proximal end of the original inner catheter 902 would be attached to the reduced diameter portion 914, while a proximal end of the guide catheter 916 would be attached to the increased diameter portion 912. Also, during use, a distal portion of each of the original inner catheter 902 and the guide catheter 916 would extend into the vascular system 22 (see FIG. 51) in the same manner as the manner in which catheter system 600 extends into the vascular system in FIG. 34. Further during use, a needle 918 would be advanced through the skin 42 and the subcutaneous tissue 44 and further through the septum 908 so as to position its distal end in the chamber 906. Thereafter, fluid may be infused into or blood may be withdrawn from the vascular system 22 with the subcutaneous port catheter system 900. The needle 918 may then be withdrawn from the chamber 906 and removed from the body 46. If at a later time the distal end portion of the original inner catheter 902 becomes totally or partially occluded due to blood clot buildup, a surgical incision could be made in the skin 42 and the subcutaneous tissue 44 so as to expose the subcutaneous port catheter system 900. Thereafter, proximal end of the guide catheter 916 can be detached from the increased diameter portion 912, and then the original inner catheter 902 can be detached from the reduced diameter portion 914. Subsequently, the original inner catheter 902 can removed from the inner lumen of the guide catheter 916. Thereafter, the replacement inner catheter 903 can be inserted into the inner lumen of the guide catheter 916. Then, the proximal end of the replacement inner catheter 903 can be attached, via a friction fit, to the reduced diameter portion 914, and then the proximal end of the guide catheter 916 can be reattached to the increased diameter portion 912 via friction fit. Of course, the incision can be closed thereafter using conventional surgical techniques such as suturing.

Obviously, the subcutaneous port catheter system 900 may be modified in a similar manner to the modifications discussed above with respect to the above-described single-lumen catheter system 600. For example, all the possible modifications and alternatives discussed above in the section entitled "VII. Conclusion" which relate to catheter system 600 are applicable to the catheter system 900.

In addition, the above-described dual-lumen catheter systems (e.g. catheter systems 16, 200, 300, 400, and 500) may be modified to incorporate any of the features of the subcutaneous port catheter system 900.

Moreover, it should be appreciated that the subcutaneous port catheter system 900 is preferably used in a manner similar to the "First Manner" or "Third Manner" of using the catheter system 600.

VIII. Catheter System 700

FIGS. 39-45 show yet another catheter system 700 which incorporates the features of the present invention therein. The catheter system 700 includes a guide catheter 702 and an original insert assembly 704.

The original insert assembly 704 includes a tube segment 705 through which fluid such as blood may be advanced. The original insert assembly 704 further includes a pusher 706 attached to the tube segment 705. The original insert assembly 704 further includes a closure member 710 such as a cap which is attached to the pusher 706.

Figure 44:
FIG. 44 is a perspective view of the tube segment of the original (or replacement) insert assembly of FIG. 41.

The pusher 706 is attached to a sidewall of the tube segment as shown in FIG. 44 so as not to interfere with fluid flow entering or exiting a proximal orifice 708 of the tube segment 705. The pusher 706 may be made of a plastic member having sufficient beam strength to advance the tube segment 705 from a position located outside of the guide catheter 702, through the guide catheter 702, and to its position shown in FIG. 39. Alternatively, the pusher 706 may be made from a metal wire such a guidewire which is commonly used to assist in the advancement of catheters within the vascular system of a patient. Of course, such metal wire would also need to possess sufficient beam strength to advance the tube segment 705 through the guide catheter 702 to its position shown in FIG. 39.

Figure 41:
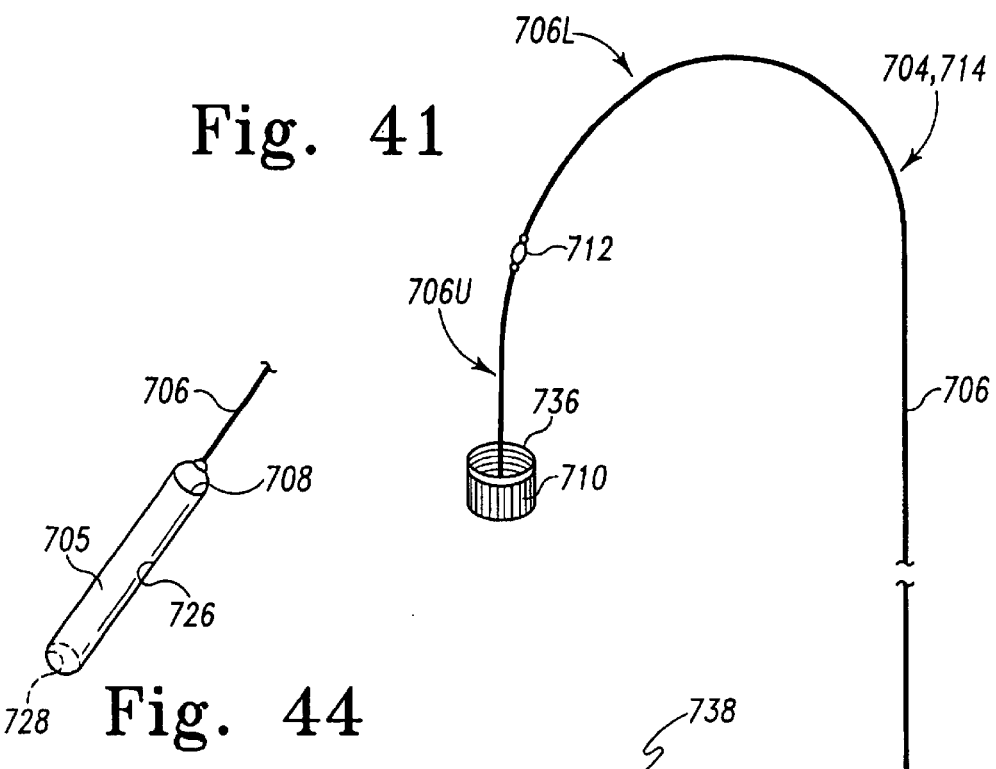
FIG. 41 is a perspective view of the original (or replacement) insert assembly of FIG. 40 entirely removed from the guide catheter.
Figure 42:
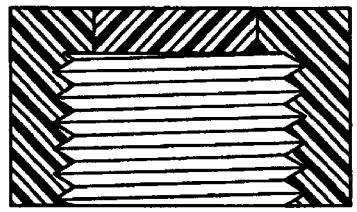
FIG. 42 is a cross-sectional view of the closure member of the original (or replacement) insert assembly of FIG. 41.
Figure 43:
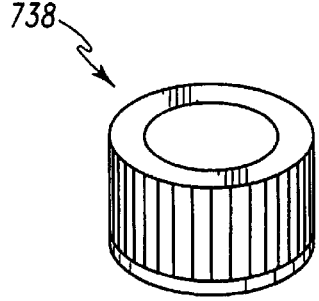
FIG. 43 is a perspective view of the closure member of the original (or replacement) insert assembly of FIG. 41.

The pusher 706 may include a swivel 712 interposed between an upper pusher portion 706U and a lower pusher portion 706L as shown in FIG. 41. The swivel 712 allows the upper pusher portion 706U to freely rotate relative to the lower pusher portion 706L. This feature allows the closure member 710 to be easily rotated in relation to the guide catheter 702 so as to couple the closure member 710 to the guide catheter 702 without causing the lower pusher portion 706L to be rotated in a similar manner. The swivel 712 may be located at any position along the length of the pusher 706.

Figure 39:
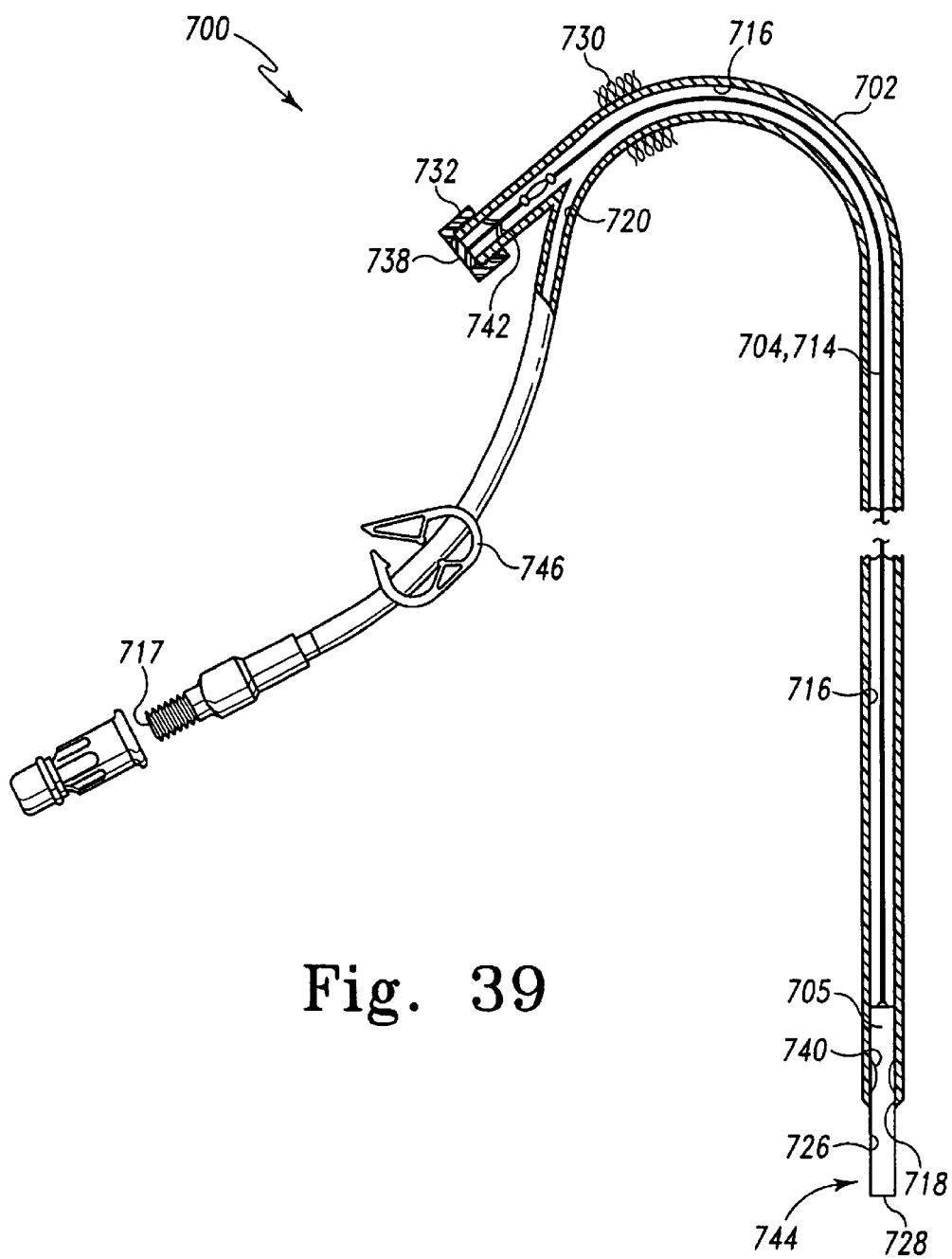
FIG. 39 is a view similar to FIG. 3, but showing another catheter system which incorporates the features of the present invention therein.
Figure 40:
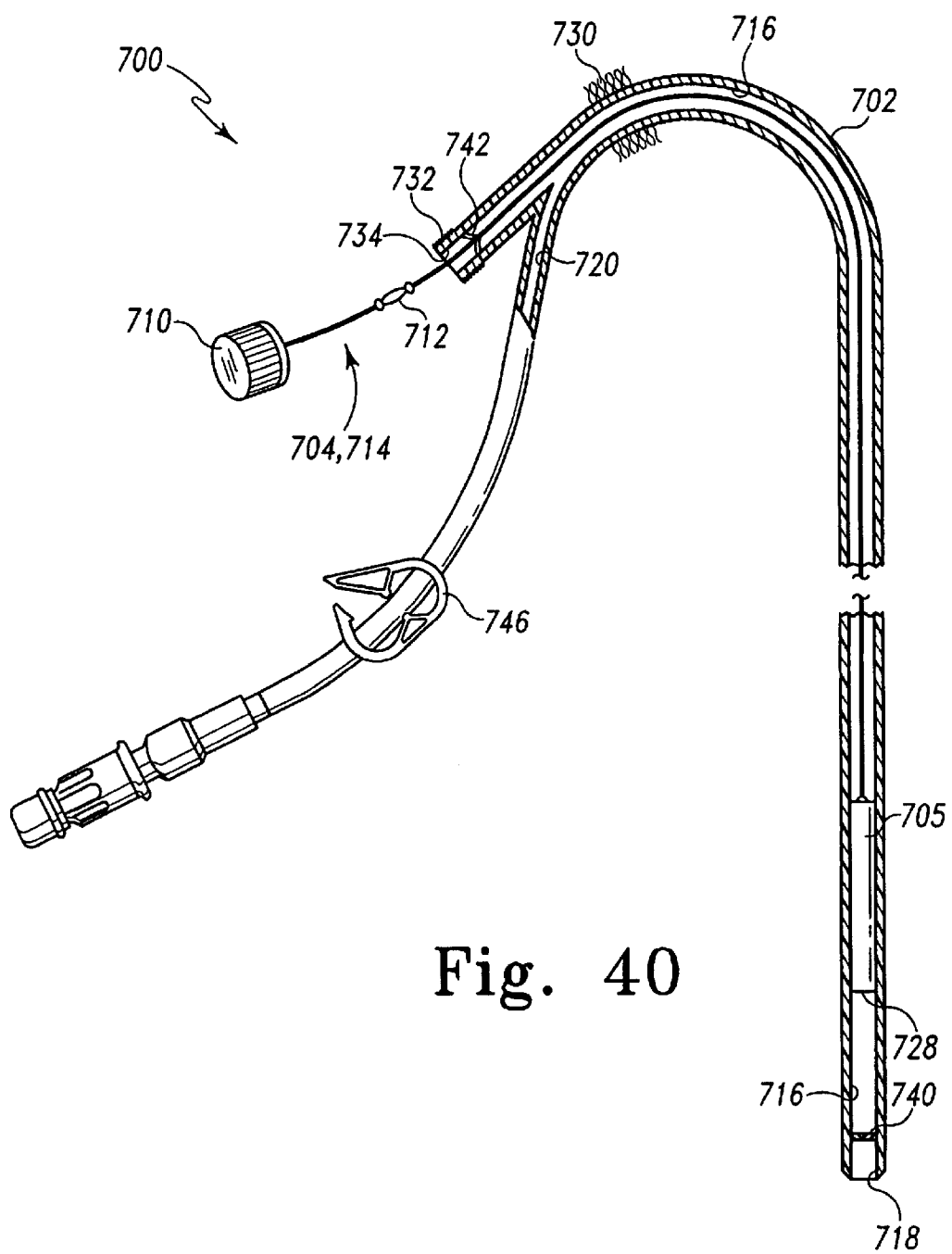
FIG. 40 is a view similar to FIG. 39, but showing the original (or replacement) insert assembly partially removed from the guide catheter.
Figure 45:
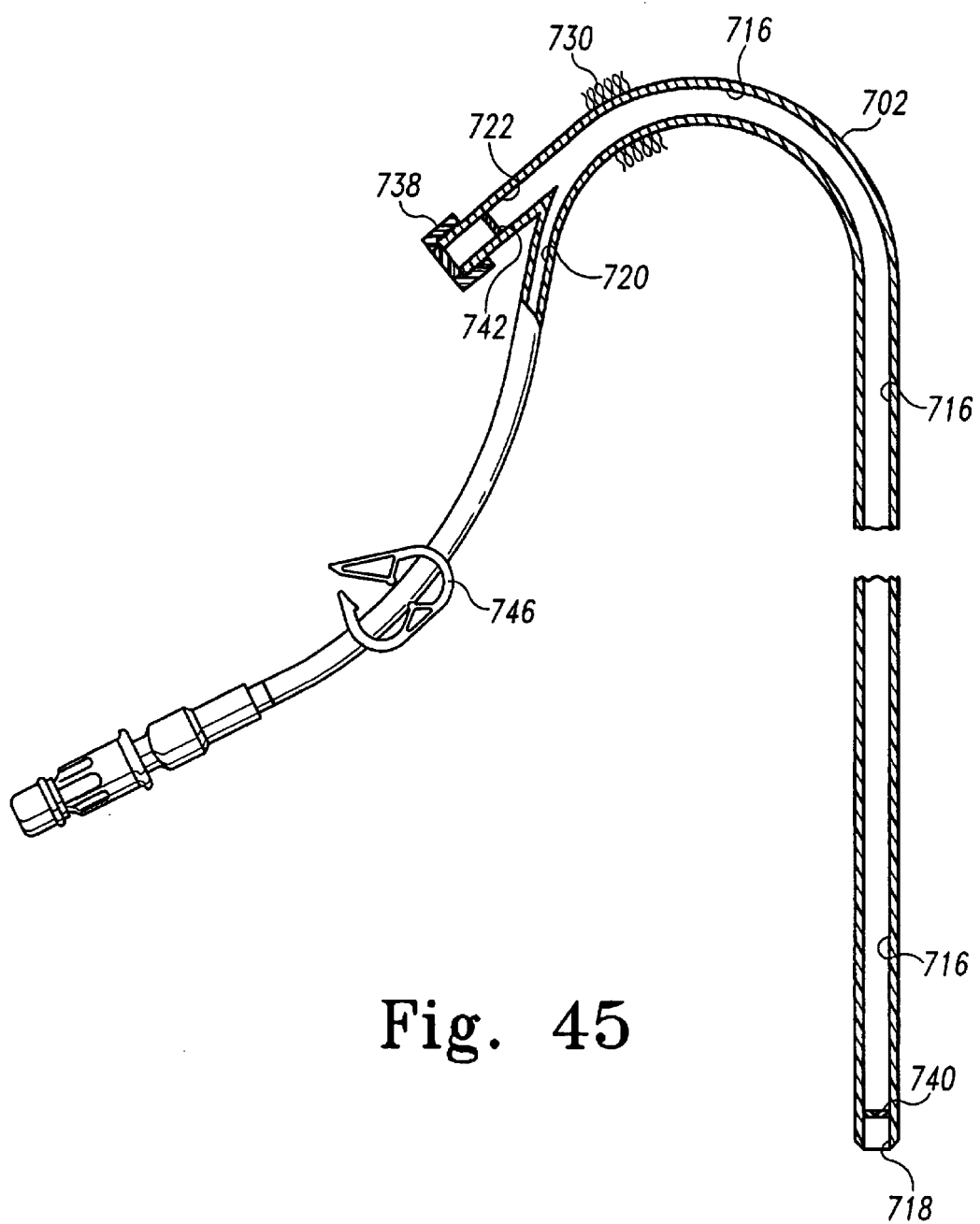
FIG. 45 is a partial cross-sectional view, partial elevational view of the guide catheter of the catheter system of FIG. 39.

The guide catheter 702 has a common lumen 716 which extends through a lower portion of the guide catheter 702 as shown in FIGS. 39, 40, and 45. The common lumen 716 defines a distal guide orifice 718. The guide catheter 702 further includes an upper main lumen 720 and a sideport lumen 722 as shown in FIGS. 39, 40, and 45.

The catheter system 700 further includes a replacement insert assembly 714 as will be discussed below. The original insert assembly 704 is able to be positioned within the sideport lumen 722 and the common lumen 716 as shown in FIGS. 39 and 40 of the guide catheter 702. Similarly, the replacement insert assembly 714 is able to be positioned within the sideport lumen 722 and the common lumen 716 as shown in FIGS. 39 and 40 of the guide catheter 702. Note that the original insert assembly 704 possesses the same physical construction and configuration as the replacement insert assembly 714. Thus, for convenience of description, FIGS. 39, 40, and 41 show reference numerals 704 and 714 identifying the same catheter. However, the original insert assembly 704 will be located within the guide catheter 702 during a first period of time, while the replacement insert assembly 714 will be located within the guide catheter 702 during a second period of time which is after the first period of time.

It should be appreciated that when the original insert assembly 704 is positioned within the sideport lumen 722 and the common lumen 716 of the guide catheter 702 as shown in FIG. 39, fluid may be advanced through a flow path which includes (i) a proximal orifice 717 of the branch of the guide catheter 702 that defines the upper main lumen 720, (ii) the upper main lumen 720, (iii) the common lumen 716, (iv) the proximal orifice 708 of the tube segment 705, (v) a tube lumen 726 of the tube segment 705, and (vi) a distal orifice 728 of the tube segment 705.

According to one preferred manner of using the catheter system 700 during a medical procedure, such as a TPN administration session, the original catheter 704 is positioned within the guide catheter 702 as shown in FIG. 39 for a first period of time during which TPN is infused therethrough. After the first period of time, the fluid flow through the catheter system 700 may become partially or even totally inhibited due to, for example, blood clot build-up at or near the distal orifice 728 defined by the tube lumen 726. In order to remedy this problem, the original insert assembly 704 is withdrawn from the guide catheter 702, and thereafter, the replacement insert assembly 714 is positioned within the guide catheter 702 as shown in FIG. 39 for a subsequent second period of time during which TPN is again infused therethrough.

Referring again to FIGS. 39, 40, and 45, the guide catheter 702 has a tissue ingrowth member 730 secured to an outer surface thereof. Tissue ingrowth member 730 is substantially identical to tissue ingrowth member 38 described hereinabove with regard to the catheter system 16.

As shown in FIGS. 39 and 40, the guide catheter 702 includes a set of external threads 732 defined on an outer surface thereof near a proximal orifice 734 of the branch of the guide catheter 702 which defines the sideport lumen 722. The set of external threads 732 cooperates with a set of internal threads 736 defined on the closure member 710. Also, the set of external threads 732 cooperates with an internally threaded cap 738 which may be coupled to the guide catheter 702 when neither insert assembly 704, 714 is coupled to the guide catheter 702 such as between TPN administration sessions.

While the original insert assembly 704 and the replacement insert assembly 714 is described as being locked to the guide catheter 702 using a locking arrangement which utilizes cooperating internal and external threads, and has substantial benefits thereby, numerous other arrangements may alternatively be incorporated into the catheter system 700 to function to lock the original insert assembly 704 and the replacement insert assembly 714 to the guide catheter 702 and still achieve many of the advantages of the present invention. For example, the detent and groove type locking arrangement (not shown) or the leg and guide channel type locking arrangement (not shown) which were described above in regard to catheter system 16 may be utilized to lock the original insert assembly 704 and the replacement insert assembly 714 to the guide catheter 702.

The guide catheter 702 further includes a distal blood flow valve 740 positioned within the common lumen 716, and a proximal blood flow valve 742 positioned within the sideport lumen 722 as shown in FIGS. 39, 40, and 45. The blood flow valves 740 and 742 are substantially identical to the blood flow valves 62 and 70 which were described hereinabove with regard to the catheter system 16.

Referring again to FIGS. 41 and 44, the tube segment 705 of the original insert assembly 704 (and the replacement insert assembly 714) defines the tube lumen 726 through which fluid is advanced. The tube lumen 726 defines the proximal orifice 708 and the distal orifice 728. The distal orifice 728 is defined in a distal portion 744 of the tube segment 705.

A clamp 746 is positioned on the guide catheter 702 which functions to prevent fluid flow through the upper main lumen 720 when desired. The clamp 746 is substantially identical in construction and function to the clamps 82, 84 discussed hereinabove with regard to the catheter system 16.

The original insert assembly 704 (and the replacement insert assembly 714) may be positioned within the guide catheter 702 as shown in FIG. 39. When the original insert assembly 704 (or alternatively the replacement insert assembly 714) is positioned within the guide catheter 702 as shown in FIG. 39, the original insert assembly 704 (or alternatively the replacement insert assembly 714) is said to be positioned in an "inserted position." When the original insert assembly 704 (or alternatively the replacement insert assembly 714) is entirely removed from the guide catheter 702 as shown in FIG. 41, the original insert assembly 704 (or alternatively the replacement insert assembly 714) is said to be positioned in a "removed position."

When the original insert assembly 704 (and the replacement insert assembly 714) is positioned in the inserted position, the distal portion 744 of the original insert assembly 704 (and the replacement insert assembly 714) extends out of the distal guide orifice 718 of the guide catheter 702 as shown in FIG. 39. Accordingly, the distal orifice 728 is positioned outside of the common lumen 716 when the original insert assembly 704 (and the replacement insert assembly 714) is located in its inserted position.

Moreover, when the original insert assembly 704 (and the replacement insert assembly 714) is located in the inserted position as shown in FIG. 39, the internally threaded closure member 710 is positioned adjacent to the set of external threads 732 such that the closure member 710 can be rotated relative to guide catheter 702 so as to lock the original insert assembly 704 (and the replacement insert assembly 714) to the guide catheter 702.

The guide catheter 702 is placed within the body 46 in substantially the same manner as was described hereinabove with respect to the placement of the guide catheter 32 of the catheter system 16 within the body 46 (i.e. by the tunneled catheter technique). Once the guide catheter 702 is placed in the body 46 as described above, the original insert assembly 704 is advanced through the sideport lumen 722 and the common lumen 716 of the guide catheter 702 so that the distal orifice 728 is advanced out of the distal guide orifice 718 and positioned within the superior vena cava 30 of the body 46. (In other words, the original insert assembly 704 is advanced to its inserted position.) The original insert assembly 704 is then locked to the guide catheter 702 in the manner previously described hereinabove.

VII(a). First Manner of Using Catheter System 700

According to a first preferred manner of using the catheter system 700, the original insert assembly 704 is replaced with the replacement insert assembly 714 only after the tube segment 705 becomes substantially inoperative due to partial or total occlusion of its tube lumen 726 as a result of, for example, blood clot buildup at, near, or around the distal orifice 728. Such a manner of using the catheter system 700 would be substantially similar to the manner of using the catheter system 16 which was discussed herein in section 1(a) entitled "First Manner of Using Catheter System 16".

VIII(b). Second Manner of Using Catheter System 700

In accordance with a second preferred manner of using the catheter system 700, the original insert assembly 704 is a "single use" device. In other words, the original insert assembly 704 of the catheter system 700 is only used for a single TPN administration session, and thereafter discarded. Hence, the original insert assembly 704 would typically never be left in the vascular system 22 long enough to become substantially inoperative due to partial or total occlusion of its tube lumen 726 as a result of, for example, blood clot build-up at, near or around the distal orifice 728. Such a manner of using the catheter system 700 would be substantially similar to the manner of using the catheter system 16 which was discussed herein in section 1(b) entitled "Second Manner of Using Catheter System 16".

Note that between TPN administration sessions, when the original insert assembly 704 (or the replacement insert assembly 714) is not located within the guide catheter 702, the closure member 738, which may be a cap, is secured to the guide catheter 702 so as to cover the proximal orifice 734 of the sideport lumen 722. The closure member 738 is substantially identical in construction and function to the closure member 100 of the catheter system 16 shown in FIGS. 11–13. Optionally and/or additionally, a clamp (not shown) which is similar in construction and function to the clamp 101 of the catheter system 16 (see FIG. 11) may be positioned on the branch of the guide catheter 702 near the proximal orifice 734 between TPN administration sessions.

When the patient desires to be engage in another TPN administration session, the guide catheter 702 is prepped in a sterile manner such as by applying an anti-bacterial solution thereto. Thereafter, the closure member 738 would be unlocked from the guide catheter 702, and thereafter the replacement insert assembly 714 would be inserted into the guide catheter 702 and then locked to the guide catheter 702 as hereinabove described. Again, this manner of using the catheter system 700 would be substantially similar to the manner of using the catheter system 16 which was discussed herein in section 1(b) entitled "Second Manner of Using Catheter System 16".

Also, please note that according to the second manner of using the catheter system 700, the original insert assembly 704 and the replacement insert assembly 714 are only a "single use" device. Accordingly, the physical structure of the tube segment 705 may be substantially the same or similar to the physical structure of a conventional short-term catheter for the same reasons hereinabove discussed in regard to the dialysis catheter 48 of the catheter system 16 in section 1(b) entitled "Second Manner of Using Catheter System 16".

VIII(c). Third Manner of Using Catheter System 700

According to a third preferred manner of using the catheter system 700, the original insert assembly 704 is replaced with the replacement insert assembly 714 after any predetermined number of TPN administration sessions is performed. For example, such predetermined number may be (i) determined from experimental studies, (ii) determined based on patient history, or (iii) determined based on other criteria. Such a manner of using the catheter system 700 would be substantially similar to the manner of using the catheter system 16 which was discussed herein in section 1(c) entitled "Third Manner of Using Catheter System 16".

VIII(d). Further Discussion Regarding Catheter System 700

The catheter system 700 may be modified in a similar manner to the modifications discussed above with respect to the catheter system 600. In particular, the modifications and alternatives of the catheter system 600 discussed above with respect to the catheter systems 600' and 600" are applicable to the catheter system 700. Moreover, all the possible modifications and alternatives discussed above in the section entitled "VII. Conclusion" which relate to catheter system 600, 600', and 600" are applicable to the catheter system 700.

In addition, certain of the above-described dual-lumen catheter systems (e.g. catheter systems 16, 200, 300, 400, and 500) may be modified to incorporate the features of the catheter system 700. For example, the catheter system 400 may be modified to utilize insert assemblies similar to insert assemblies 704, 714 instead of utilizing catheters 404, 406.

Of course, the guide catheter 402 would need to be modified to include a sideport lumen which would extend from the branch of the guide catheter 402 on which external threads 418 are defined.

It should be appreciated that according to the "First Manner" of using catheter systems 16, 200, 300, 400, 500, 600, 600', 600", and 700 set forth at different locations above, a common theme is to replace some type of temporary, advancable conduit which is supported by a guide catheter during a medial procedure after the temporary, advancable conduit becomes partially or totally inoperative due to partial or total occlusion of its lumen as a result of, for example, blood clot build-up at, near, or around the distal orifice of the conduit. For example, in the case of catheter system 16 of FIGS. 1–13, the temporary, advancable conduit is catheter 48, while in the case of catheter system 700 of FIGS. 39–45, the temporary, advancable conduit is tube segment 705. In both of these cases, replacement of the temporary, advancable conduit 48, 705 effectively and conveniently eliminates the partial or total occlusion of the fluid path of the respective catheter system and causes such fluid path to be reopened so that such catheter system becomes functional once again.

Additionally, it should be appreciated that according to the "Second Manner" and "Third Manner" of using catheter systems 16, 200, 300, 400, 500, 600, 600', 600", and 700 set forth at different locations above, a common theme is to replace some type of temporary, advancable conduit which is supported by a guide catheter during a medical procedure before the temporary, advancable conduit becomes partially or totally inoperative due to partial or total occlusion of its lumen as a result of, for example, blood clot build-up at, near, or around the distal orifice of the conduit. For example, in the case of catheter system 16 of FIGS. 1–13, the temporary, advancable conduit is catheter 48, and in the case of catheter system 700 of FIGS. 39–45, the temporary, advancable conduit is tube segment 705. In both of these cases, replacement of the temporary, advancable conduit 48, 705 effectively and conveniently prevents the fluid path of the respective catheter system from becoming partially or totally occluded.

In each of the catheter systems 16, 200, 300, 400, 500, 600, 600', 600", and 700, the distal portion of the temporary, advancable conduit possesses the distal opening (or orifice) through which fluid enters or exits the respective catheter system and which is necessarily located within the patient's vascular system for at least a period of time in which it is in contact with the patient's blood. According to each of the "First Manner", "Second Manner" and "Third Manner" of using the catheter systems 16, 200, 300, 400, 500, 600, 600', 600", and 700, strategic replacement or removal of this particular part of the respective catheter system (i.e. the distal portion of the temporary, advancable conduit which possesses the distal opening (or orifice) through which fluid enters or exits the respective catheter system and which is necessarily located within the patient's vascular system for at least a period of time in which it is in contact with the patient's blood) enables the catheter system to either (i) become operative once again after a period of being inoperative, or (ii) never become inoperative due to partial or total occlusion of this distal portion of the catheter system as a result of, for example, blood clot build-up at, near, or around its distal orifice.

IX. Catheter System 800

Another catheter system 800 which incorporates the features of the present invention therein is shown in FIGS. 46, 46A–B, 47, 47A, 48, 49, 49A–C, 50, and 50A–D. The catheter system 800 includes a guide catheter 32 (see FIG. 46), an original dialysis catheter 48, and a replacement dialysis catheter 58 (see FIG. 47). The catheter system 800 is somewhat similar to the catheter system 16. Thus, the same reference numerals are used in FIGS. 46, 46A–B, 47, 47A, 48, 49, 49AC, 50, and 50A–D to designate common components which were previously discussed with regard to FIGS. 1–13. Moreover, the description of the components of the catheter system 800 which are common to the catheter system 16 will not be undertaken since they are designated with common reference numerals and such components have been previously described hereinabove. In addition, the guide catheter 32 of the catheter system 800 is placed within the body 46 in substantially the same manner as was described hereinabove with respect to the placement of the guide catheter 32 of the catheter system 16 within the body 46 (i.e. by the tunneled catheter technique).

Figures 46, 46A:
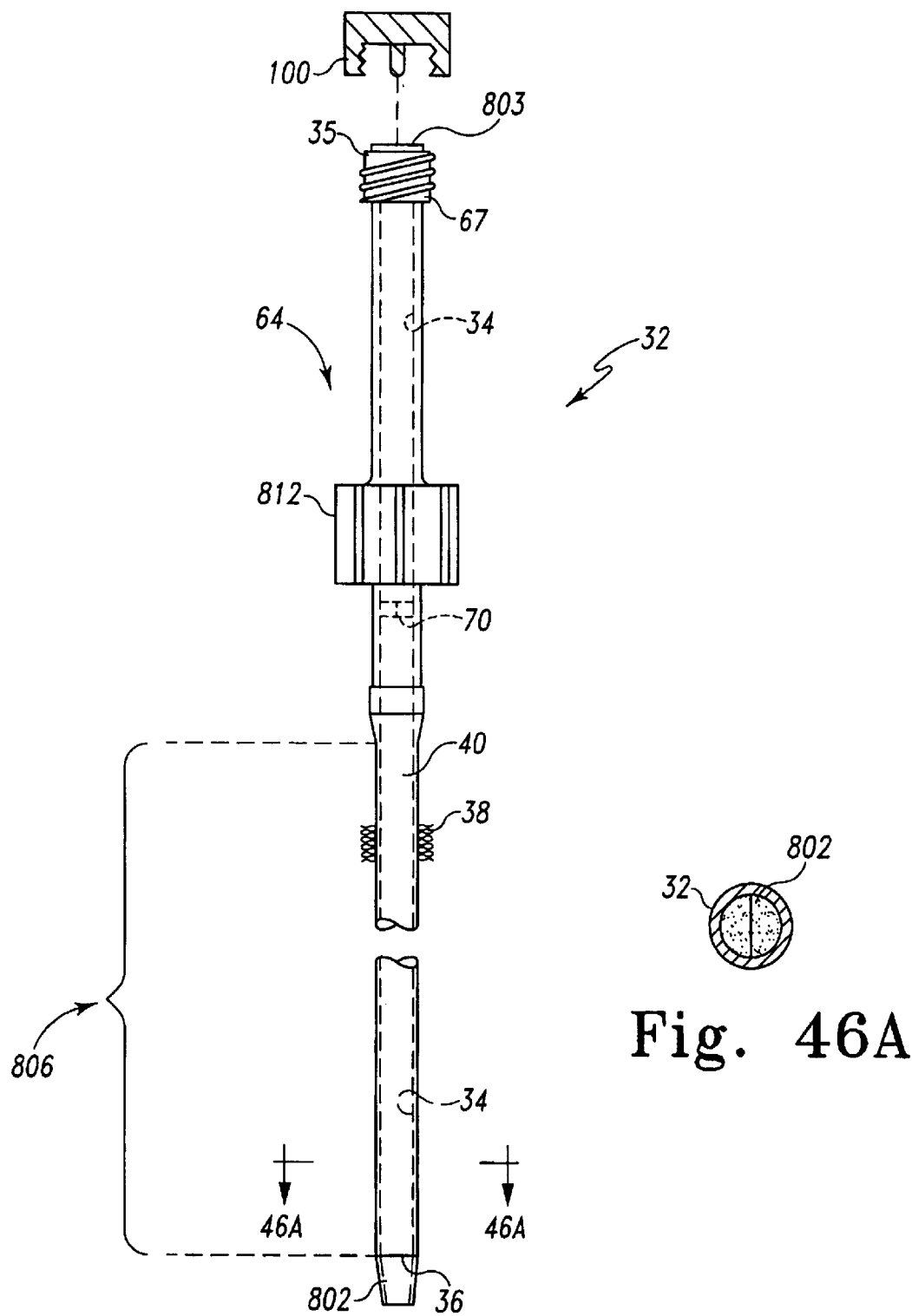
FIG. 46 is an enlarged side elevational view of the guide catheter of the long-term dialysis catheter system shown in FIG. 48.
FIG. 46A is an enlarged cross sectional view of the guide catheter taken along the line 46A—46A of FIG. 46 as viewed in the direction of the arrows.

However, the catheter system 800 differs from the catheter system 16 in that the guide catheter 32 of the catheter system 800 does not possess a distal blood flow valve positioned within the guide lumen 34. Rather, the guide catheter 32 of the catheter system 800 includes a duckbill valve 802 positioned external to the guide lumen 34 just below the distal guide orifice 36 as shown in FIG. 46. Further, an O-Ring seal 803 may be positioned within the guide lumen 34 of the guide catheter 32 at the proximal guide orifice 35 as shown in FIG. 46 so as to facilitate fluid tight coupling between the guide catheter 32 and the original dialysis catheter 48 (and the replacement dialysis catheter 58).

Figure 46B:
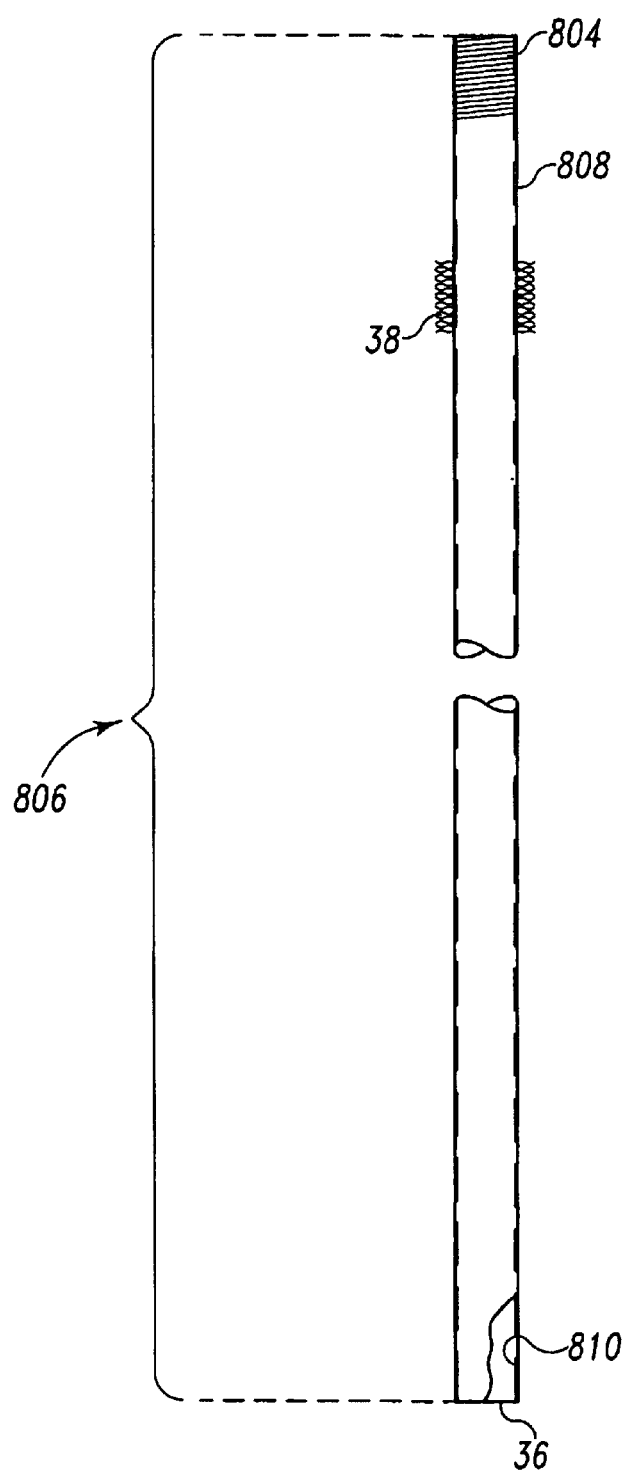
FIG. 46B is an enlarged side elevational view of a portion of the guide catheter of FIG. 46.

Another difference between the catheter system 800 and the catheter system 16 is that the guide catheter 32 of the catheter system 800 includes a stainless steel wire coil 804 which is cylindrically wound and extends the entire length of a segment 806 of the guide catheter 32 as shown in FIGS. 46 and 46B. Note that for clarity of description only a proximal portion of the segment 806 is shown possessing the wire coil 804. Further, the entire outer surface 40 of the segment 806 of the guide catheter 32 has positioned thereon a nylon material 808 such as PEBAX. PEBAX is a tradename, commonly known to one skilled in the art, for a type of nylon polymer which is commonly used in the medical device industry for the manufacture of catheters. Moreover, the inner surface of the guide catheter 32 of the catheter system 800 which defines the guide lumen 34 may have positioned thereon a Teflon coating 810. The Teflon coating 810 may facilitate sliding of the original dialysis catheter 48 (and a replacement dialysis catheter 58) relative to the guide catheter 32 when such dialysis catheter 48, 58 is positioned within the guide catheter 32.

Alternatively, instead of the wire coil 804 being made of stainless steel, the wire coil 804 may be made from another metallic material such as NITINOL. NITINOL is a tradename, commonly known to one skilled in the art, for a type of metallic material that is commonly used in the medical device industry in the manufacture of medical devices. The thickness (i.e. the outer diameter) of the strand of wire that makes up the wire coil 804 may be uniform as it extends from the proximal end of the segment 806 to the distal end of the segment 806. Alternatively, certain portion(s) of the strand of wire which makes up the wire coil 804 may possess a first larger thickness while other portion(s) may possesses a second smaller thickness. For example, the strand of wire that makes up the wire coil 804 which is required to be bent into a U-shaped orientation when the guide catheter 32 of the catheter system 16 is implanted in the patient's body 46 (see e.g. FIG. 7) may possess the first larger thickness, while the strand of wire that makes up the wire coil 804 which is linearly oriented on each side of the U-shaped portion may possess the second smaller thickness. This variation in the thickness of the strand of wire that makes up the wire coil 804 may reduce the likelihood of kinking or other deformation of the guide catheter 32 during implantation and use of the guide catheter 32. Also, it should be noted that the more tightly the strand of wire which makes up the wire coil 804 is wound (i.e. the more turns per linear inch), the less likely the guide catheter 32 will kink or otherwise deform during implantation and use of the guide catheter 32.

Still another difference between the catheter system 800 and the catheter system 16 is that the first locking mechanism 64 and the second locking mechanism 66 of the catheter system 800 have a somewhat different physical configuration when compared to the first locking mechanism 64 and the second locking mechanism 66 of the catheter system 16. In particular, FIGS. 46, 46A–B, 47, 47A, and 48 show the physical configuration of the first locking mechanism 64 and the second locking mechanism 66. One point of distinction is that both locking mechanisms 64, 66 of the catheter system 800 possess finger grips. More specifically, the first locking mechanism 64 possesses a first finger grip 812, while the second locking mechanism 66 possesses a second finger grip 814. These grips form the basis of a supplemental locking system 816 and facilitate user coupling of the dialysis catheter 48, 58 to the guide catheter 32.

In particular, each of the finger grips 812, 814 have a plurality of grooves 818 defined therein (see FIG. 49). The supplemental locking system 816 includes a locking clip 820 having a pair of nubs 822 as shown in FIGS. 49A, 49B, and 49C. In order to further lock the original dialysis catheter 48 (and the replacement dialysis catheter 58) to the guide catheter 32, the locking clip 820 is applied over the finger grips 812, 814 when the grooves 818 of the first finger grip 812 are aligned with the grooves 818 of the second finger grip 814 as shown in FIG. 49. When so aligned, the nubs 822 are received into the grooves 818 of finger grips 812, 814 as shown in FIG. 49C so as to prevent relative rotation and thus separation of the original dialysis catheter 48 (and the replacement dialysis catheter 58) from the guide catheter 32.

Another supplemental locking system 824 is shown in FIGS. 50, 50A, 50B, 50C, and 50D. The supplemental locking system 824 includes a slider 826 which is securely positioned within a first recess 828 defined in the first finger grip 812 and a second recess 830 defined in the second finger grip 814. When the slider 826 is moved to its leftmost position in the direction of arrow 832, the original dialysis catheter 48 (and the replacement dialysis catheter 58) can be rotated in relation to the guide catheter 32 so as to separate the dialysis catheter 48, 58 from the guide catheter 32. When the slider 826 is located in its position as shown in FIG. 50, the slider 826 prevents relative rotation and thus separation of the original dialysis catheter 48 (and the replacement dialysis catheter 58) from the guide catheter 32.

Figures 47, 47A:
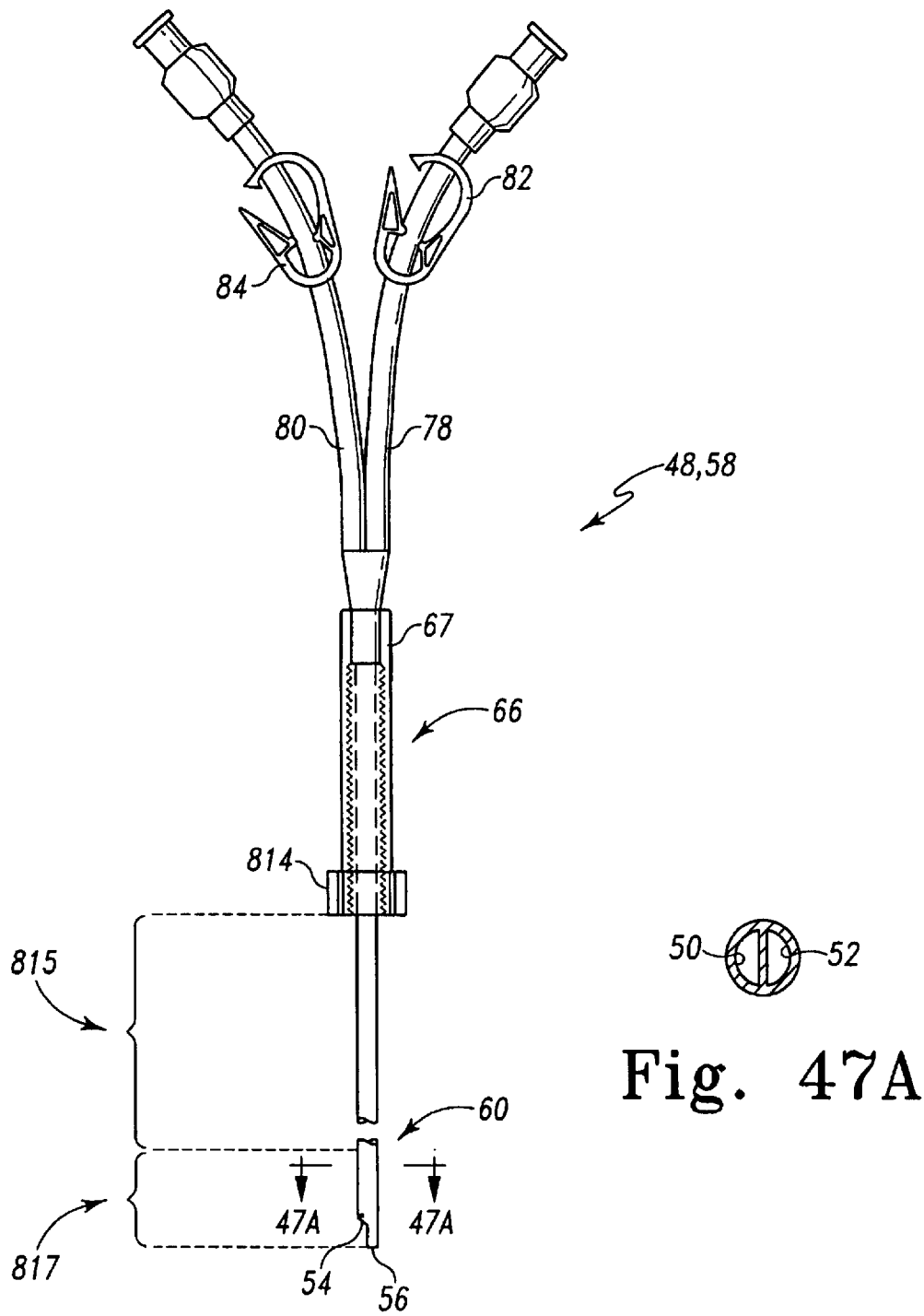
FIG. 47 is an enlarged side elevational view of the original catheter (and replacement catheter) of the long-term dialysis catheter system shown in FIG. 48.
FIG. 47A is an enlarged cross sectional view of the guide catheter taken along the line 47A—47A of FIG. 47 as viewed in the direction of the arrows.
Figure 48:
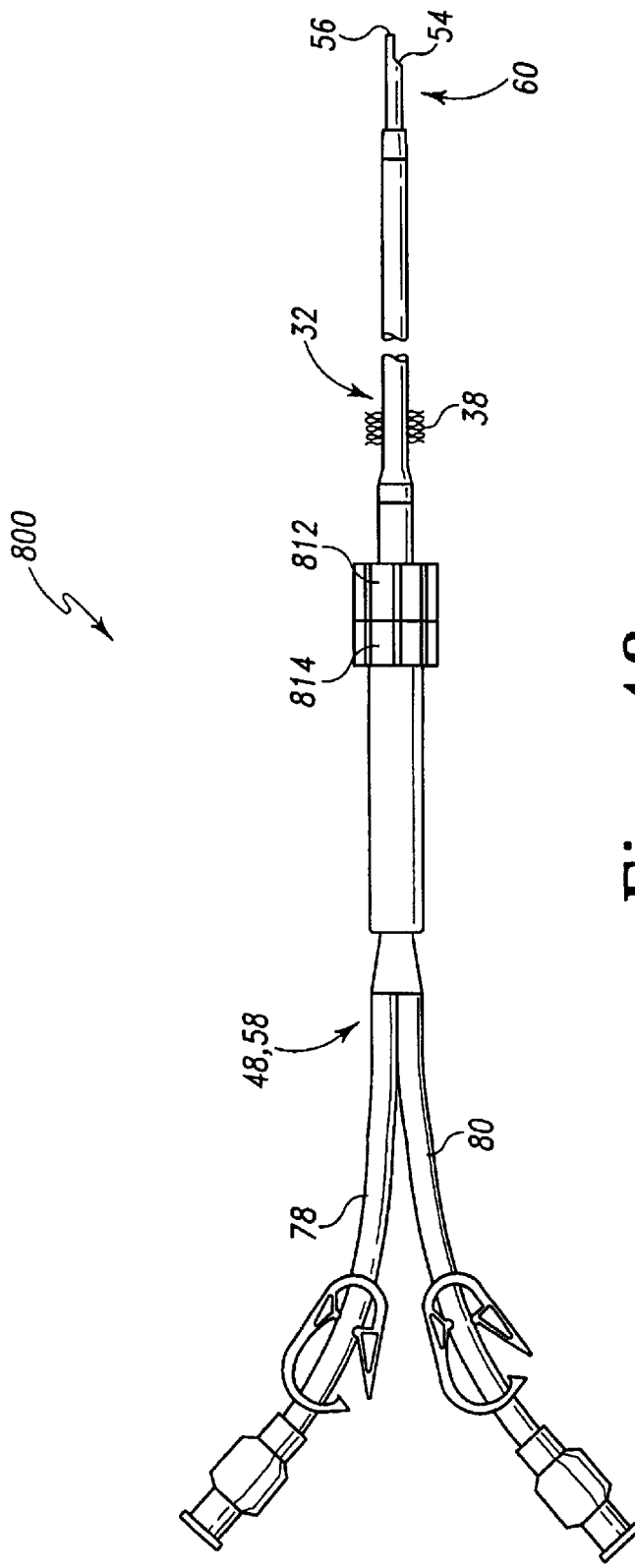
FIG. 48 is a view similar to FIG. 3, but showing another catheter system which incorporates the features of the present invention therein.

Yet another distinction between the catheter system 800 and the catheter system 16 is that the original dialysis catheter 48 (and the replacement dialysis catheter 58) includes a first segment 815 which possesses a first degree of hardness (having a first durometer rating), while a second segment 817 possesses a second degree of hardness (having a second durometer rating) as shown in FIG. 47. Providing the first segment 815 with relatively increased hardness may facilitate the slidability of the original dialysis catheter 48 (and the replacement dialysis catheter 58) in relation to the guide catheter 32. The difference in the degree of hardness between the first segment 815 and the second segment 817 may be created by manufacturing the first segment 815 with a first material possessing a first resin-to-nylon content ratio, while manufacturing the second segment 815 with a second material possessing a second resin-to-nylon content ratio which is different from the first resin-to-nylon content ratio. Note that the degree of hardness of a catheter depends on the percentage of resin used in comparison to the percentage of nylon used in the manufacturing process of the catheter. Resin is a filler material. The more resin used, the softer the catheter. The more nylon used, the harder the catheter. A catheter can be made of two different segments having difference degrees of hardness by thermally fusing the two catheter segments together at a transition area. This transition area may be located at any position along the length of the catheter. With regard to catheter system 800, the first segment 815 of the working catheter 48, 58 could be configured to possess a higher degree of hardness in order to provide better slidability of the working catheter 48, 58 in relation to the guide catheter 32. This would make the distal end segment of the working catheter 48, 58 a softer configuration in order to minimize trauma to the vascular system in which it is used. For example, the distal end segment of the working catheter 48, 58 which is advanced out of the distal guide orifice 36 of the guide catheter 32 according to one preferred method of the present invention would possess a relatively soft configuration in order to minimize trauma to vascular system.

Alternatively, the original dialysis catheter 48 (and the replacement dialysis catheter 58) of the catheter system 800 may be manufactured such that its first segment 815 and its second segment 817 possess an identical degree of hardness (or identical durometer rating).

Obviously, the catheter system 800 may be modified in a similar manner to the modifications discussed above with respect to the above-described dual-lumen catheter systems (e.g. catheter systems 16, 200, 300, 400, and 500) For example, all the possible modifications and alternatives discussed above in the section entitled "VII. Conclusion" which relate to catheter system 16, 200, 300, 400, and 500 are applicable to the catheter system 800.

In addition, the above-described dual-lumen catheter systems (e.g. catheter systems 16, 200, 300, 400, and 500) and the single lumen catheter systems (e.g. catheter systems 600, 600', 600'', and 700) may be modified to incorporate any of the features of the catheter system 800.

Alternative Manner of Using Catheter System(s)

An alternative manner of using the above-described catheter systems is set forth below. For efficiency of description, the alternative manner will only be described with respect to the catheter system 16. However, it should be appreciated that any of the other catheter systems described herein (e.g. catheter systems 200, 300, 400, 500, 600, 600', 600'', 700, and 800) may be used in this alternative manner.

Figure 53:
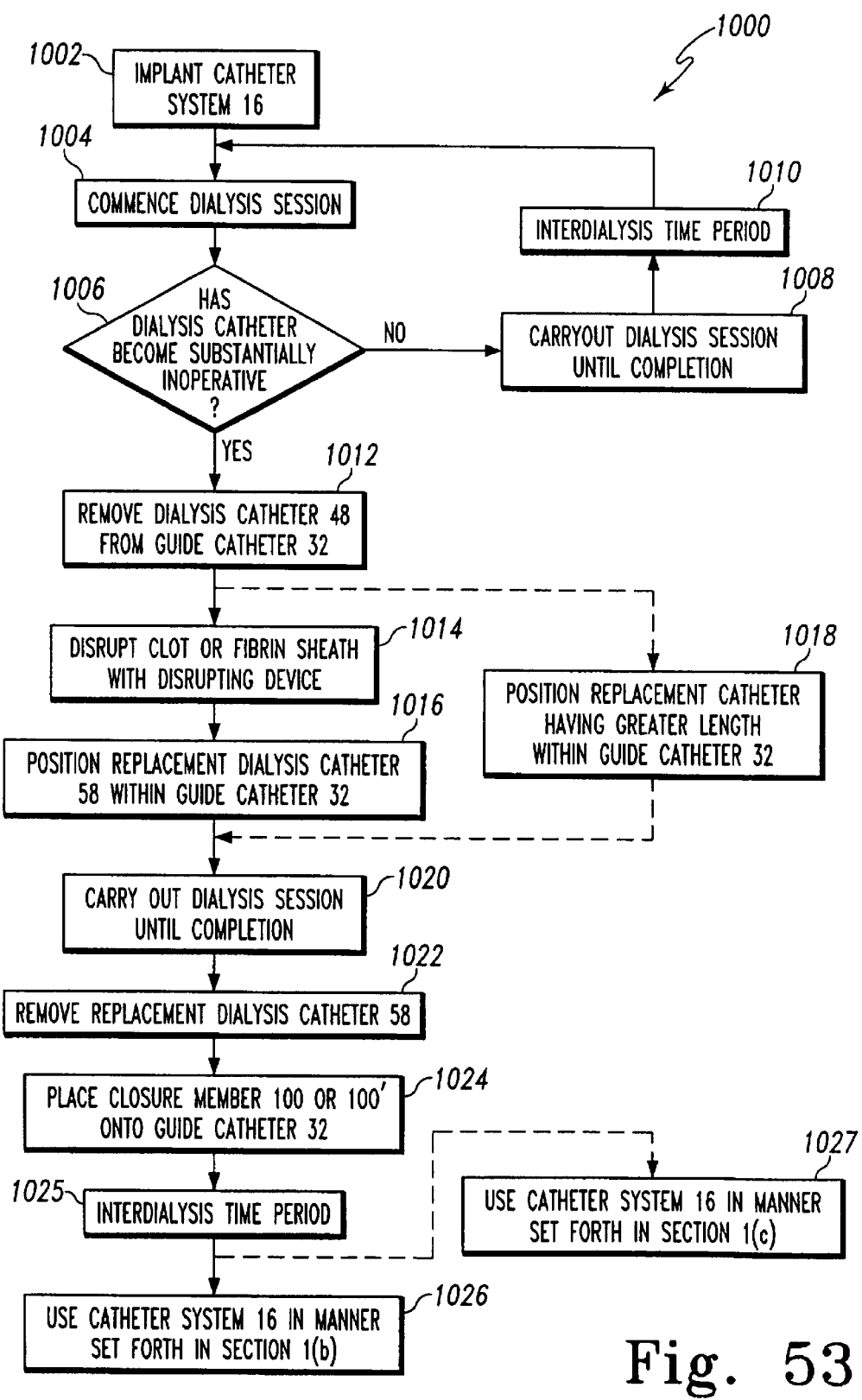
FIG. 53 is a flow chart setting forth an alternative manner of using catheter system 16 in accordance with the present invention.

The alternative manner of using the catheter system 16 is set forth in the flow chart 1000 shown in FIG. 53. Initially, at step 1002, the catheter system 16 is implanted in the patient's body 46. As described above, the catheter system 16 is implanted in the body 46 by placing the guide catheter 32 in the body 46 using the tunneled catheter technique, and then placing the dialysis catheter 48 within the guide catheter 32.

Thereafter, a dialysis session is commenced at step 1004. If the dialysis catheter 48 has not become substantially inoperative due to partial or total occlusion of either or both of its lumens 50, 52 due to blood clot or fibrin sheath buildup or similar detrimental condition (see step 1006), then the dialysis session is carried out until completion at step 1008. After completion of the dialysis session, the patient is able to carry on about his/her business during an interdialysis time period at step 1010. The interdialysis time period is a time period after completion of one dialysis session and before commencement of a subsequent dialysis session.

However, if at step 1006 the dialysis catheter 48 has become substantially inoperative due to partial or total occlusion of either or both of its lumens 50, 52 due to blood clot or fibrin sheath buildup or similar condition, the dialysis catheter 48 is replaced with the replacement dialysis catheter 58. In particular, the dialysis catheter 48 is unlocked from the guide catheter 32 and withdrawn from the guide lumen 34 at step 1012. Then, at step 1014, a clot or fibrin sheath disrupting device (not shown), such as a pig-tailed catheter, a fogarty balloon catheter, or an angioplasty balloon catheter, may be advanced within the guide catheter 32 so that a portion thereof extends out a distal end of the guide catheter 32. The clot or fibrin sheath disrupting device is then manipulated or otherwise deployed so as to break off any clot or fibrin sheath which is attached to the distal end portion of the guide catheter 32. Thereafter, at step 1016, the dialysis catheter 58 is positioned within the guide lumen 34 of the guide catheter 32, and locked to the guide catheter 32.

Alternatively, instead of performing steps 1014 and 1016, another dialysis catheter (not shown) that is substantially the same as the dialysis catheter 58 but which has a greater length (e.g. a length of about 4.0 cm greater than the length of the dialysis catheter 58) is positioned within the guide lumen 34 of the guide catheter 32, and locked to the guide catheter 32 (see alternate step 1018). Placing such a greater length dialysis catheter in the guide catheter 32 would cause its distal end to extend beyond any clot or fibrin sheath attached to the distal end portion of the guide catheter 32 thereby removing the likelihood that any of such clot or fibrin sheath would interfere with proper functioning of such increased length dialysis catheter.

Thereafter, the dialysis session is carried out to completion at step 1020 whereby blood is withdrawn from the patient's body 46, dialyzed, and then the dialyzed blood is returned to the patient's body 46. After completion of the dialysis session, the replacement catheter 58 is removed from the guide catheter 32 at step 1022, and the closure member 100 is secured to the guide catheter 32 so as to cover its proximal guide orifice 35 (see FIG. 11-13) at step 1024. Then, the patient is able to carry on about his/her business during an interdialysis time period at step 1025. Thereafter, at step 1026, the catheter system is used in the manner described hereinabove in section 1(b) entitled "Second Manner of Using Catheter System 16". Alternatively, at step 1027, instead of using the catheter system in the manner hereinabove described in section 1(b), the catheter system may be used in the manner hereinabove described in section 1(c) entitled "Third Manner of Using Catheter System 16".

Figure 54:
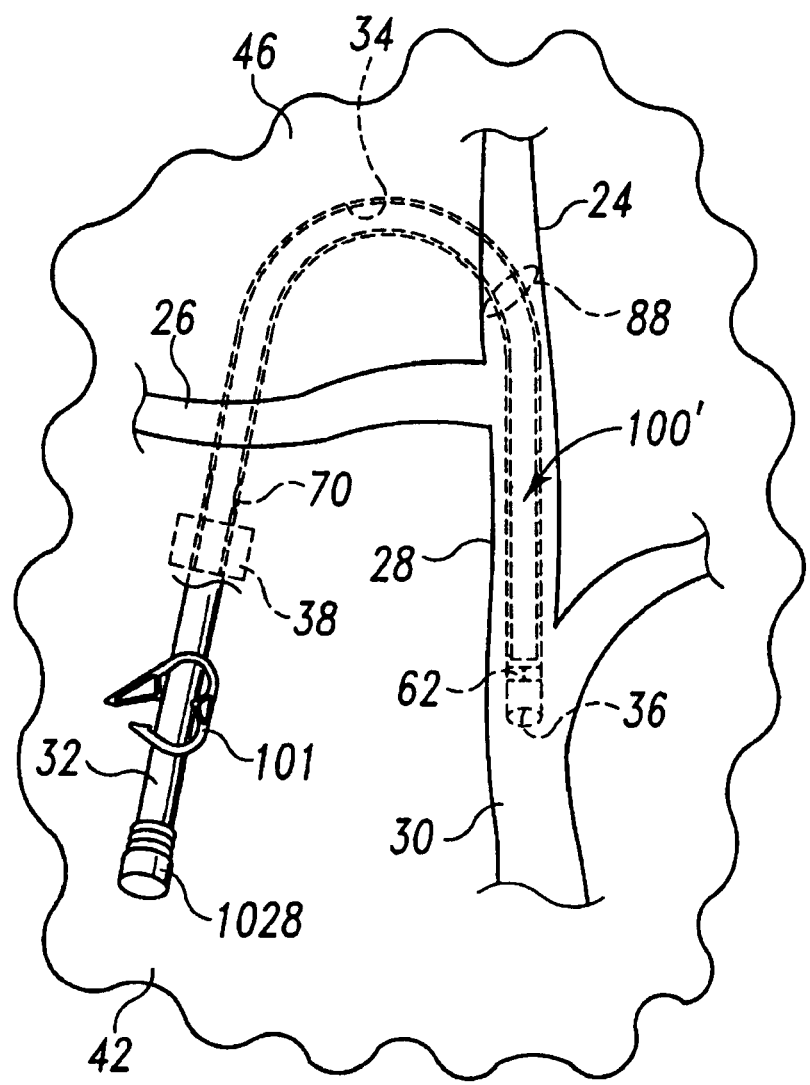
FIG. 54 is a view similar to FIG. 11, but showing another closure member located in the guide catheter and used in accordance with the alternative manner set forth in the flow chart of FIG. 53.
Figure 55:
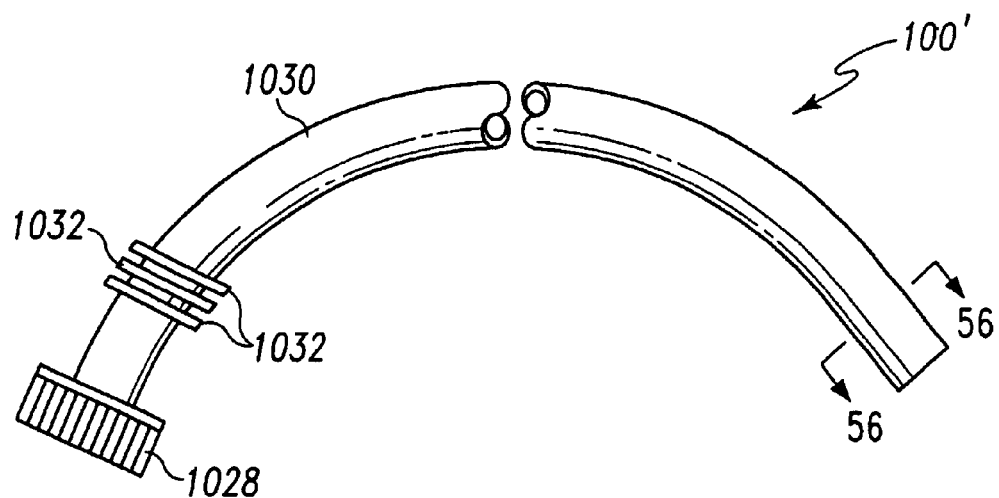
FIG. 55 is side elevational view of the closure member of FIG. 54.
Figure 56:
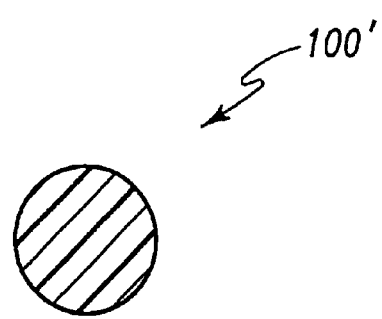
FIG. 56 is a cross sectional view taken along the line 56—56 of FIG. 55 as viewed in the direction of the arrows.

One example of the closure member 100 was disclosed as being a cap (see e.g. 11–13). Alternatively, another example of the closure member 100 which is suitable for use in the present invention is a mandrel assembly 100' that occupies most of the space of the guide lumen 34 which is located proximal to the distal valve 62 as shown in FIGS. 54–56. The mandrel assembly 100' includes an internally threaded cap portion 1028 similar to the cap shown in FIGS. 12 and 13. This closure member 100' further includes a body portion 1030 which consists of a solid member such as a block of plastic material which is suitable for placement in the vascular system. For example, the body portion 1030 may be made of a solid piece of polyethylene or polyurethane. Alternatively, the body portion 1030 may be a hollow member having a closed off end portion (i.e. an end portion that does not possess a distal opening) as shown in FIG. 56. The body portion 1030 is rotatably secured to the cap portion 1028 by a swivel (not shown) that is similar to the swivel 712 of the catheter system 700. The mandrel assembly 100' further includes a plurality of elastic seal members 1032 secured to the body portion 1030. Note that when the mandrel assembly 100' is located within the guide catheter 32 as shown in FIG. 54, the elastic seal members 1032 are urged against the inner sidewall of the guide catheter 32 so as to provide added security against the leakage of blood out of the vascular system through the guide lumen 34 and/or leakage of air into the vascular system through the guide lumen 34.

Figure 57:
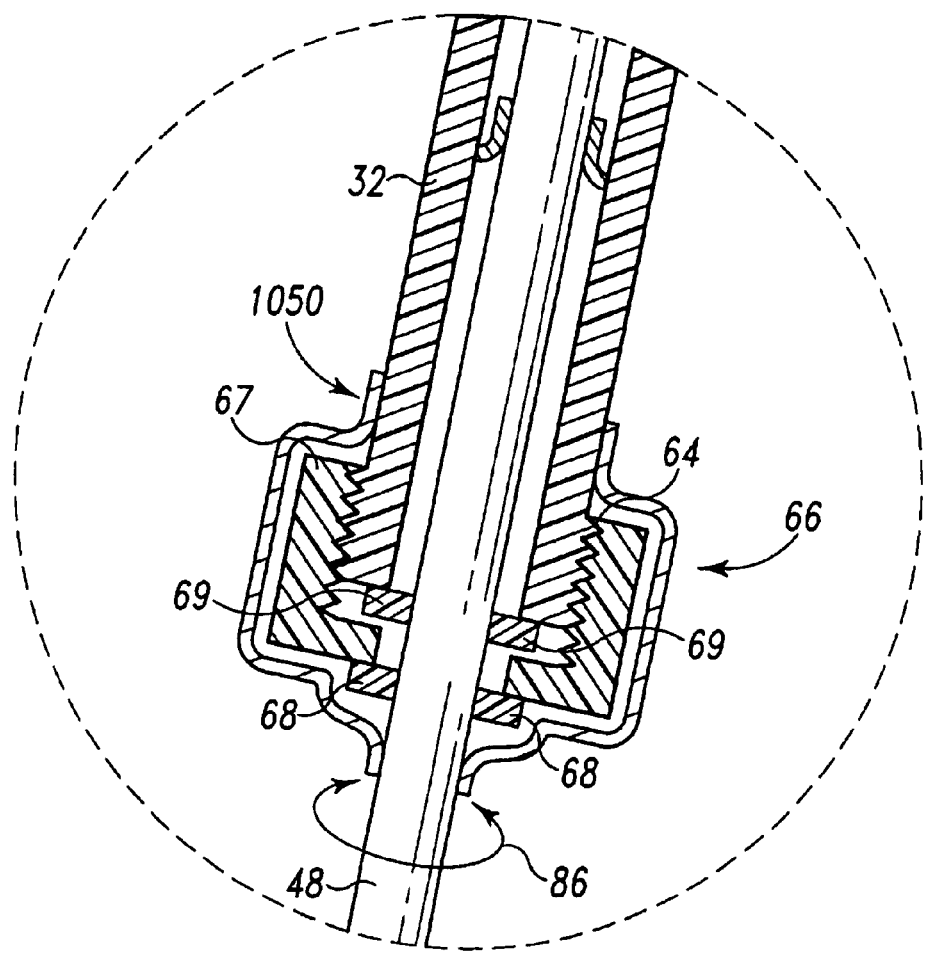
FIG. 57 is a view similar to FIG. 6, but showing a safety mechanism secured around the locking mechanism of the catheter system in accordance with another aspect of the present invention.

It should be appreciated that as an alternative arrangement, the catheter system 16 may include a safety mechanism 1050 as shown in FIG. 57 that is configured to inhibit unlocking of the dialysis catheter 48 from the guide catheter 32 without destruction of the safety mechanism. The safety mechanism 1050 is a piece of plastic material that completely surrounds the locking mechanism 64, 66 (see FIG. 57) around its entire 360 degree periphery, and also above it proximally and below it distally. The plastic material may be shrink wrapped to such configuration around the locking mechanism by heating. Alternatively, the safety mechanism 1050 may be any other type of device which inhibits unlocking of the dialysis catheter 48 from the guide catheter 32 without destruction of the safety mechanism. For example, the safety mechanism 1050 may be a piece of hard plastic (that is not shrink wrapped) which is configured to contain the locking mechanism 64, 66 therein.

Inclusion of the safety mechanism 1050 is particularly beneficial when the catheter system 16 is used in the alternative manner set forth in the flow chart 1000 shown in FIG. 53. Indeed, the safety mechanism 1050 may be left in place on the catheter system 16 for the entire useful life of the catheter system when the catheter system 16 is implanted in a patient whose particular blood characteristics do not cause the dialysis catheter 48 to dysfunction due to blood clot or fibrin sheath buildup on the distal end portion of the dialysis catheter 48. For example, when the catheter system 16 is implanted in a new patient who has never before used a central venous catheter, there exists a possibility that the new patient's blood characteristics are such that dysfunction of the catheter system 16 will not occur while the catheter system 16 is implanted in such new patient (e.g. during the maturation of an arteriovenous fistula). Accordingly, it is possible that such new patient may never need to replace the original dialysis catheter 48 with a replacement dialysis catheter 58. The safety mechanism 1050 provides an added degree of security in this situation by securely stowing the locking mechanism 64, 66 under the safety mechanism 1050. However, if dysfunction of the dialysis catheter 48 does occur, the safety mechanism 1050 may simply be cut off or otherwise destroyed thereby exposing the locking mechanism 64, 66 to enable a user to replace the original dialysis catheter 48 with a replacement dialysis catheter 58.

Hybrid Removable/Retractable Catheter System 1200

Figure 58:
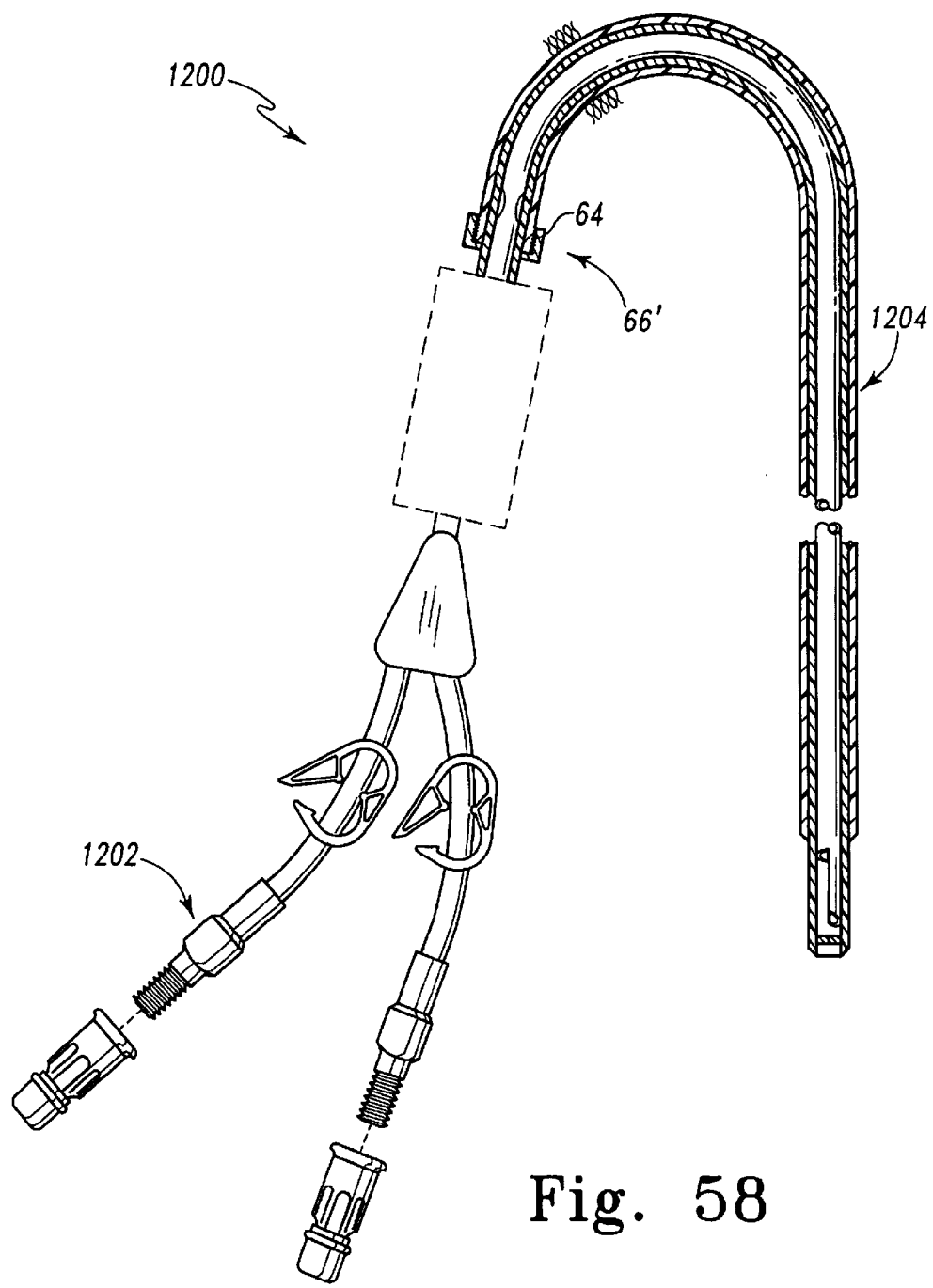
FIG. 58 is a side elevational view of another catheter system that incorporates the features of the present invention therein.

Another catheter system 1200 that incorporates the features of the present invention therein is shown in FIG. 58. The catheter system 1200, which may be referred to a hybrid catheter system, includes an inner retractable catheter system 1202 and an outer guide catheter 1204. The inner catheter system 1202 is constructed and used in the same manner as the catheter system 12 that is disclosed in U.S. Pat. No. 6,190,371 issued to Maginot et al., except for two differences. The entire disclosure of U.S. Pat. No. 6,190,371 is hereby incorporation by reference. The first difference is that the tissue ingrowth member 43 disclosed in the '371 patent would not be included on the retractable inner catheter system 1202. The second difference is that the inner retractable catheter system 1202 has a locking mechanism 66' which is substantially identical in construction and use as the second locking mechanism 66 of the catheter system 16 described hereinabove (see e.g. FIG. 6).

The outer guide catheter 1204 is constructed and used in the same manner as the guide catheter 32 described hereinabove (e.g. see FIG. 4A) except for one difference. The one difference is that the outer guide catheter 1204 possesses a larger inner diameter to accommodate the positioning of the inner retractable catheter system 1202 therein as shown in FIG. 58.

The hybrid catheter system 1200 is implanted and used in the same manner as described with respect to the implantation and use of the catheter system 12 that is disclosed in U.S. Pat. No. 6,190,371. However, if for any reason the inner retractable catheter system 1202 becomes dysfunctional, the inner retractable catheter system 1202 could be replaced with a new inner retractable catheter system that is identical in construction and function to the inner retractable catheter system 1202. The inner retractable catheter system 1202 may be replaced in the same manner as described above with respect to the replacement of the dialysis catheter 48 with the replacement dialysis catheter 58.

Obviously, the catheter system 1200 may be modified in a similar manner to the modifications discussed above with respect to all of the above-described catheter systems. Moreover, all of the above-described catheter systems may be modified to incorporate any of the features of the catheter system 1200.

There is a plurality of advantages of the present invention arising from the various features of each of the catheter systems described herein. It will be noted that alternative embodiments of each of the catheter systems of the present invention may not include all of the features described yet still benefit from at least some of the advantages of such features. Those of ordinary skill in the art may readily devise their own implementations of each of the catheter systems that incorporate one or more of the features of the present invention and fall within the spirit and scope of the present invention as defined by the appended claims.

What is claimed is:

1. A subcutaneous port catheter system, comprising:
   a reservoir defining a chamber therein;
   a guide catheter having a guide lumen and a distal guide orifice; and
   an inner catheter positioned within said guide lumen and extending through said distal guide orifice,
   wherein said reservoir has a first coupling configured to removably connect said guide catheter to said reservoir, and
   wherein said reservoir further has a second coupling configured to removably connect said inner catheter to said reservoir.

2. The subcutaneous port catheter system of claim 1, wherein said reservoir includes a septum configured to be traversed by a needle.

3. The subcutaneous port catheter system of claim 1, wherein said guide catheter includes a valve positioned adjacent to said distal guide orifice.

4. The subcutaneous port catheter system of claim 1, wherein said reservoir is fluid communication with said inner catheter.

5. The subcutaneous port catheter system of claim 1,
   said first coupling is configured to form a first friction fit connection between said guide catheter to said reservoir, and
   said second coupling is configured to form a second friction fit connection between said inner catheter to said reservoir.

6. The subcutaneous port catheter system of claim 1, wherein said proximal end of said guide catheter is spaced apart from said proximal end of said inner catheter when both said guide catheter and said inner catheter are connected to said reservoir.

7. A subcutaneous port catheter system, comprising:
   a reservoir defining a chamber therein;
   a guide catheter attached to said reservoir, said guide catheter having a guide lumen and a distal guide orifice; and
   an inner catheter attached to said reservoir, said inner catheter being positioned within said guide lumen and extending through said distal guide orifice,
   wherein said reservoir includes an attachment cannula which is in fluid communication with said chamber,
   wherein said attachment cannula includes an increased diameter portion and a reduced diameter portion,
   wherein said guide catheter is attached to said increased diameter portion, and
   wherein said inner catheter is attached to said reduced diameter portion.

8. The subcutaneous port catheter system of claim 7, wherein said reservoir includes a septum configured to be traversed by a needle.

9. The subcutaneous port catheter system of claim 7, wherein said guide catheter includes a valve positioned adjacent to said distal guide orifice.

10. The subcutaneous port catheter system of claim 7, wherein:
    each of said increased diameter portion and said reduced diameter portion possesses a ribbed outer surface,
    said guide catheter is removably attached to said ribbed outer surface of said increased diameter portion in a friction fit manner, and
    said inner catheter is removably attached to said ribbed outer surface of said reduced diameter portion in a friction fit manner.

11. The subcutaneous port catheter system of claim 7, wherein:
    said reservoir is fluid communication with said inner catheter.

12. A subcutaneous port catheter system, comprising:
    a reservoir having a septum and defining a chamber;
    an inner catheter which is in fluid communication with said chamber; and
    a guide catheter having a guide lumen, said inner catheter being at least partially positioned within said guide lumens,
    wherein said reservoir has a first coupling configured to removably connect said guide catheter to said reservoir, and
    wherein said reservoir further has a second coupling configured to removably connect said inner catheter to said reservoir.

13. The subcutaneous port catheter system of claim 12, wherein:
    said guide catheter has a distal guide orifice, and
    said inner catheter extends through said distal guide orifice.

14. The subcutaneous port catheter system of claim 13, said inner catheter has a distal opening, and
said distal opening is positioned outside of said guide catheter.

15. The subcutaneous port catheter system of claim 12, wherein said guide catheter includes a valve positioned adjacent to said distal guide orifice.

16. The subcutaneous port catheter system of claim 12, wherein:
said first coupling is configured to form a first friction fit connection between said guide catheter to said reservoir, and
said second coupling is configured to form a second friction fit connection between said inner catheter to said reservoir.

17. The subcutaneous port catheter system of claim 12, wherein said proximal end of said guide catheter is spaced apart from said proximal end of said inner catheter when both said guide catheter and said inner catheter are connected to said reservoir.

18. A subcutaneous port catheter system, comprising:
a reservoir having a septum and defining a chamber;
an inner catheter which is in fluid communication with said chamber; and
a guide catheter having a guide lumen, said inner catheter being at least partially positioned within said guide lumen,
wherein said reservoir includes an attachment cannula which is in fluid communication with said chamber,
wherein said attachment cannula includes an increased diameter portion and a reduced diameter portion,
wherein said guide catheter is attached to said increased diameter portion, and
wherein said inner catheter is attached to said reduced diameter portion.

19. The subcutaneous port catheter system of claim 18, wherein:
said guide catheter has a distal guide orifice, and
said inner catheter extends through said distal guide orifice.

20. The subcutaneous port catheter system of claim 19, wherein:
said inner catheter has a distal opening, and
said distal opening is positioned outside of said guide catheter.

21. The subcutaneous port catheter system of claim 18, wherein said guide catheter includes a valve positioned adjacent to said distal guide orifice.

22. The subcutaneous port catheter system of claim 18, wherein:
each of said increased diameter portion and said reduced diameter portion possesses a ribbed outer surface,
said guide catheter is removably attached to said ribbed outer surface of said increased diameter portion in a friction fit manner, and
said inner catheter is removably attached to said ribbed outer surface of said reduced diameter portion in a friction fit manner.

* * * * *